United States Patent
Johns et al.

(10) Patent No.: US 7,262,052 B1
(45) Date of Patent: Aug. 28, 2007

(54) α-2/δ GENE

(75) Inventors: Margaret Ann Johns, Ann Arbor, MI (US); Brian Moldover, Ann Arbor, MI (US); James David Offord, Ann Arbor, MI (US)

(73) Assignee: Warner Lambert Company, Ann Arbor, MI (US)

( * ) Notice: Subject to any disclaimer, the term of this patent is extended or adjusted under 35 U.S.C. 154(b) by 0 days.

(21) Appl. No.: 09/787,657

(22) PCT Filed: Oct. 7, 1999

(86) PCT No.: PCT/US99/23519

§ 371 (c)(1),
(2), (4) Date: Mar. 20, 2001

(87) PCT Pub. No.: WO00/20450

PCT Pub. Date: Apr. 13, 2000

(51) Int. Cl.
C07H 21/04 (2006.01)
C12N 15/63 (2006.01)
C12N 5/16 (2006.01)

(52) U.S. Cl. ............ 435/325; 530/412; 536/23.5
(58) Field of Classification Search ........... 536/23.5; 435/6, 975
See application file for complete search history.

(56) References Cited

FOREIGN PATENT DOCUMENTS

| WO | 9504822 | 2/1995 |
|---|---|---|
| WO | 9811131 | 3/1998 |
| WO | 0012711 | 3/2000 |

OTHER PUBLICATIONS

Myers, R.M. GenBank Accession No. G36524, Dec. 31, 1997.*
Soares et al. GenBank Accession No. AA815447, Feb. 13, 1998.*
Database EMBL 'Online!, AC AA190607, Hillier et al., 1997.
Database EMBL 'Online!, AC Z44942, Auffray et al., 1994.
Database EMBL 'Online!, AC R20288, Hillier et al., 1995.
Database EMBL 'Online!, AC AA459684, Hillier et al., 1994.
Database EMBL 'Online!, AC AC005343, Muzny et al., 1998.
Database EMBL 'Online!, AC AA719773, Hillier et al., 1998.
Database EMBL 'Online!, AC AA001473, Hillier et al., 1996.
Database EMBL 'Online!, AC Z75742, Wilkinson et al., 1996.
Database EMBL 'Online!, AC AB011130, Ohara et al., 1998.
Gee et al., "The Novel Anticonvulsant Drug, Gabapentin (Neurontin), Binds to the α2δ Subunit of a Calcium Channel", *The Journal of Biological Chemistry*, vol. 271, No. 1, 1996, pp. 5768-5776.
Brown and Gee, "Cloning and Deletion Mutagenesis of the α2δ Calcium Channel Subunit from Porcine Cerebral Cortex", *The Journal of Biological Chemistry*, vol. 273, No. 39, 1998, pp. 24458-25465.
Klugbauer et al., "Molecular Diversity of the Calcium Channel α2δ Subunit", *The Journal of Neuroscience*, vol. 19, No. 2, 1999, pp. 654-691.
Williams et al., "Structure and Functional Expression of $\alpha^1$, $\alpha^2$, and β Subunits of a Novel Human Neuronal Calcium Channel Subtype", *Neuron*, vol. 8, 1992, pp. 71-84.
Walker and De Waard, "Subunit interaction sites in voltage-dependent $Ca^{2+}$ channels: role in channel function", *Trends in Neurosciences*, vol. 21, No. 4, 1998, pp. 148-154.

* cited by examiner

*Primary Examiner*—Janet L. Andres
*Assistant Examiner*—Stephen Gucker
(74) *Attorney, Agent, or Firm*—Philip B. Polster, II; Mehdi Ganueizadeh

(57) ABSTRACT

The present invention relates to three novel genes and polypeptides derived therefrom encoding "α2δ-C" and/or "α2δ-D" proteins which exist as a subunit in many calcium channels. The invention also describes methods for using the novel gene and polypeptides in the detection of genetic deletions of the gene, subcellular localization of the polypeptide, binding assays in connection with chemical databases, gene therapy.

9 Claims, 4 Drawing Sheets

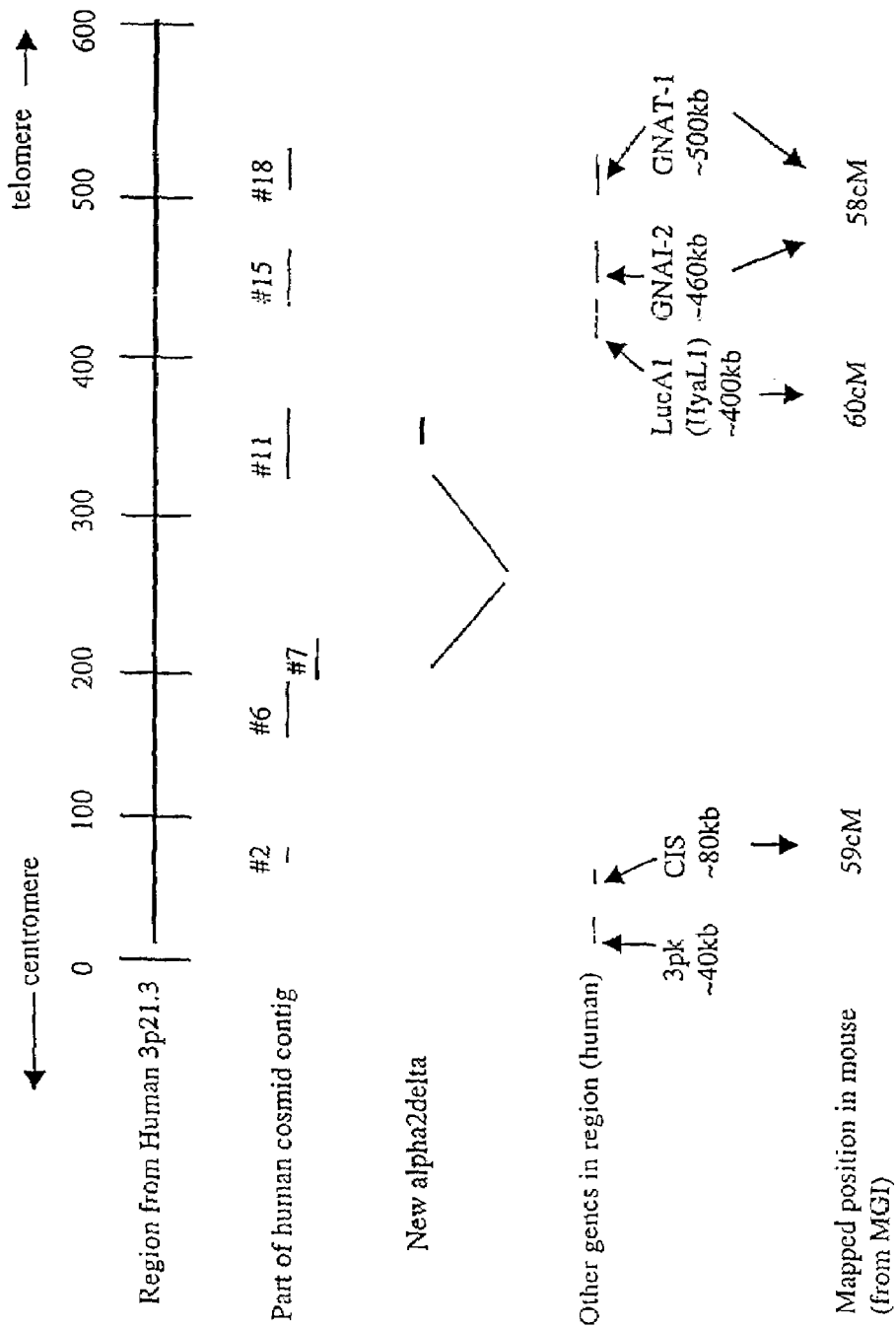
FIGURE #1

FIGURE #2
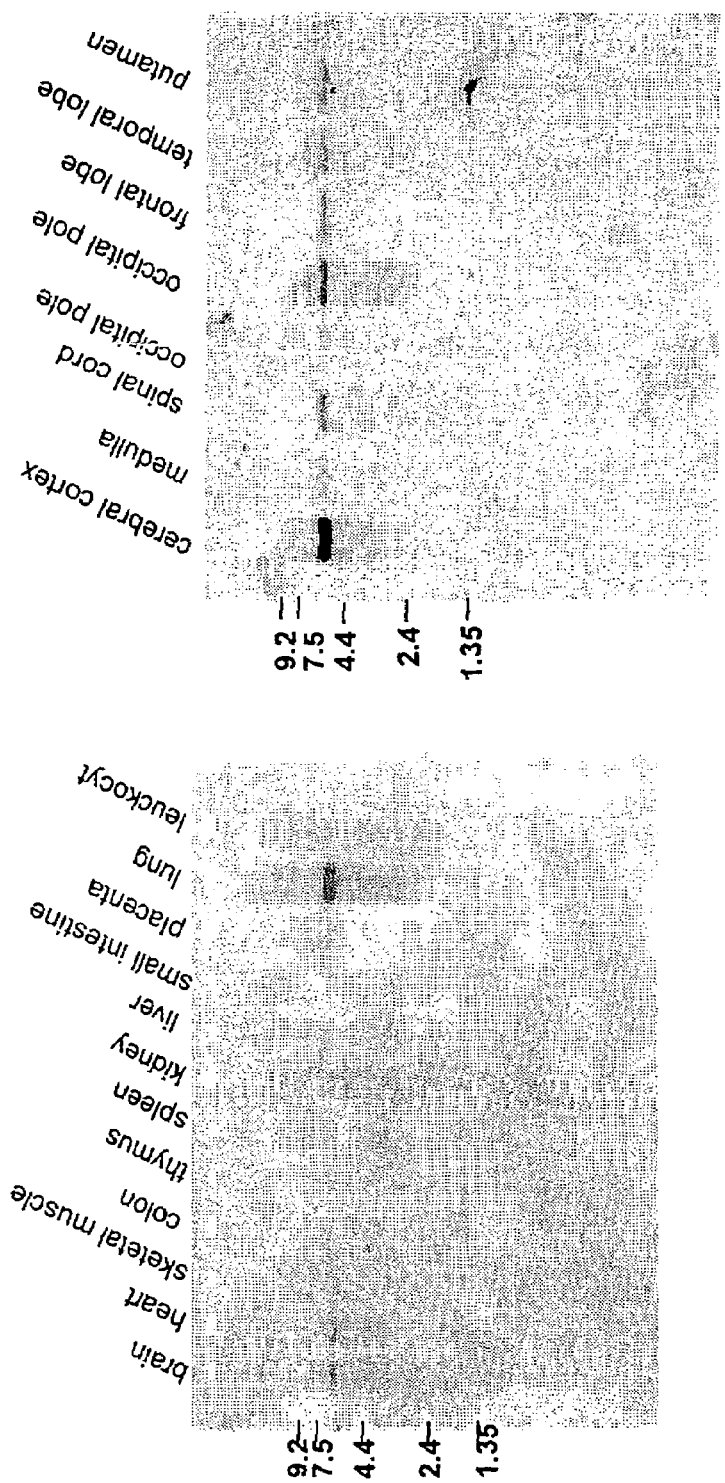

FIGURE #3
Figure 3. [³H] Gabapentin binding activity by human α2δ2 in transiently transfected Cos 7 cells
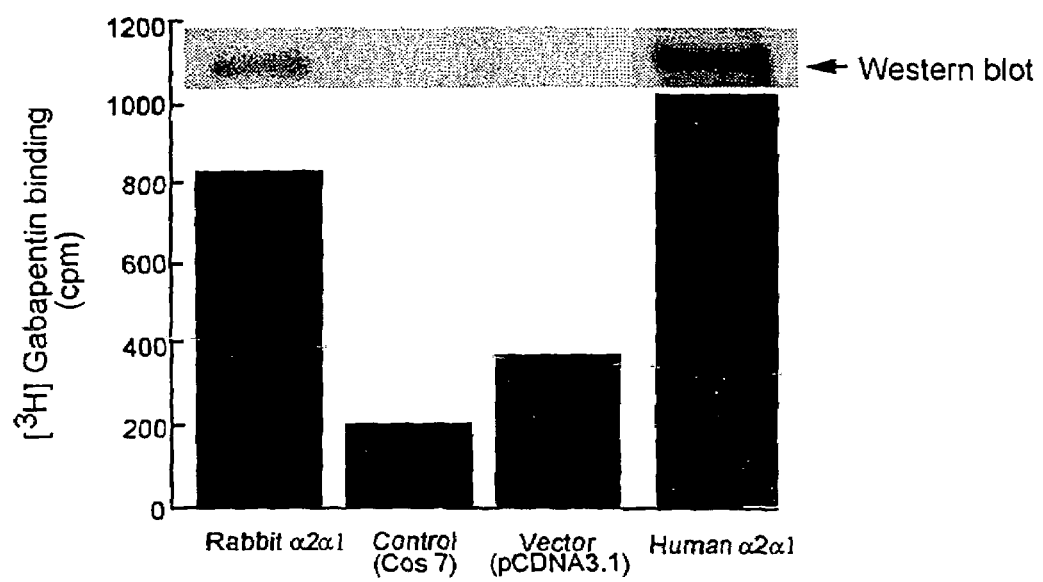

FIGURE #4
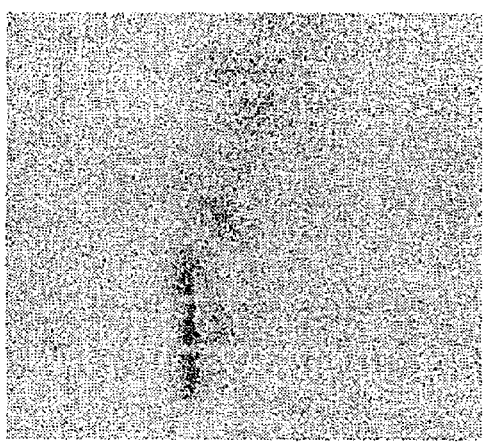
Lane 1-Brain RNA
Lane 2-Kidney RNA
Lane 3-Testis RNA
Lane 4-Lung RNA
Lane 5-Heart RNA
Lane 6-Placenta RNA
Lane 7-Liver RNA

SEQUENCE LISTING

```
<160> NUMBER OF SEQ ID NOS: 49

<210> SEQ ID NO 1
<211> LENGTH: 5482
<212> TYPE: DNA
<213> ORGANISM: Homo sapiens

<400> SEQUENCE: 1
cgggcagcgc agcccgcaga ggcgctgcgg cccgtgcagc cccggaggcc cctcgcggag      60
aaggcggcgg cggaggagag gccgagttac cgcccgccgc ccgcgccccc ccaaccccgc     120
cgccgccgcc gccgccgcca ctgccccccc tccccgcggc gccgcatctt gaatggaaac     180
atggcggtgc cggctcggac ctgcggcgcc tctcggcccg gccagcgcg gactgcgcgc      240 ccctggcccg gctgcggccc ccaccctggc cccggcaccc ggcgcccgac gtccgggccc     300
ccgcgcccgc tgtggctgct gctgccgctt ctaccgctgc tcgccgcccc cggcgcctct     360
gcctacagct tcccccagca gcacacgatg cagcactggg cccggcgtct ggagcaggag     420
gtcgacggcg tgatgcggat ttttggaggc gtccagcagc tccgtgagat ttacaaggac     480
aaccggaacc tgttcgaggt acaggagaat gagcctcaga agttggtgga gaaggtggca     540
ggggacattg agagccttct ggacaggaag gtgcaggccc tgaagagact ggctgatgct     600
gcagagaact tccagaaagc acaccgctgg caggacaaca tcaaggagga agacatcgtg     660
tactatgacg ccaaggctga cgctgagctg gacgaccctg agagtgagga tgtggaaagg     720
gggtctaagg ccagcaccct aaggctggac ttcatcgagg acccaaactt caagaacaag     780
gtcaactatt catacgcggc tgtacagatc cctacggaca tctacaaagg ctccactgtc     840
atcctcaatg agctcaactg gacagaggcc ctggagaatg tgttcatgga aaaccgcaga     900
caagacccca cactgctgtg gcaggtcttc ggcagcgcca caggagtcac tcgctactac     960
ccggccaccc cgtggcgagc ccccaagaag atcgacctgt acgatgtccg aaggagaccc    1020
tggtatatcc agggggcctc gtcacccaaa gacatggtca tcatcgtgga tgtgagtggc    1080
agtgtgagcg gcctgaccct gaagctgatg aagacatctg tctgcgagat gctggacacg    1140
ctgtctgatg atgactatgt gaatgtggcc tcgttcaacg agaaggcaca gcctgtgtca    1200
tgcttcacac acctggtgca ggccaatgtg cgcaacaaga aggtgttcaa ggaagctgtg    1260
cagggcatgg tggccaaggg caccacaggc tacaaggccg gctttgagta tgcctttgac    1320
cagctgcaga actccaacat cactcgggcc aactgcaaca agatgatcat gatgttcacg    1380
gatggtggtg aggaccgcgt gcaggacgtc tttgagaagt acaattggcc aaaccggacg    1440
```

-continued

```
gtgcgcgtgt ttactttctc cgtggggcag cataactatg acgtcacacc gctgcagtgg    1500
atggcctgtg ccaacaaagg ctactatttt gagatccctt ccatcggagc catccgcatc    1560
aacacacagg aatatctaga tgtgttgggc aggcccatgg tgctggcagg caaggaggcc    1620
aagcaggttc agtggaccaa cgtgtatgag gatgcactgg gactggggtt ggtggtaaca    1680
gggaccctcc ctgttttcaa cctgacacag gatggccctg ggaaaagaa gaaccagctg    1740 atcctgggcg tgatgggcat tgacgtggct ctgaatgaca tcaagaggct gaccccaac    1800 tacacgcttg gagccaacgg ctatgtgttt gccattgacc tgaacggcta cgtgttgctg    1860 cacccccaatc tcaagcccca gaccaccaac ttccgggagc tgtgactct ggacttcctg    1920 gatgcggagc tagaggatga gaacaaggaa gagatccgtc ggagcatgat tgatggcaac    1980
aagggccaca agcagatcag aacgttggtc aagtccctgg atgagaggta catagatgag    2040
gtgacacgga actacacctg ggtgcctata aggagcacta actacagcct ggggctggtg    2100
ctcccaccct acagcacctt ctacctccaa gccaatctca gtgaccagat cctgcaggtc    2160 aagtatttg agttcctgct ccccagcagc tttgagtctg aaggacacgt tttcattgct    2220
cccagagagt actgcaagga cctgaatgcc tcagacaaca caccgagtt cctgaaaaac    2280 tttattgagc tcatggagaa agtgactcca gactccaagc agtgcaacaa cttccttctg    2340
cacaacctga tcttggacac gggcatcacg cagcagctgg tagagcgtgt gtggagggac    2400
caggatctca acacgtacag cctactggcc gtgttcgctg ccacagacgg tggcatcacc    2460
cgagtcttcc ccaacaaggc agctgaggac tggacagaga ccctgagcc cttcaatgcc    2520 agcttctacc gccgcagcct ggataaccac ggttatgtct tcaagcccc acaccaggat    2580 gccctgttaa ggccgctgga gctggagaat gacactgtgg gcatcctcgt cagcacagct    2640
gtggagctca gcctaggcag gcgcacactg aggccagcag tggtgggcgt caagctggac    2700
ctagaggctt gggctgagaa gttcaaggtg ctagccagca accgtaccca ccaagaccag    2760
cctcagaagt gcggccccaa cagccactgt gagatggact gcgaggttaa caatgaggac    2820
ttactctgtg tcctcattga tgatggagga ttcctggtgc tgtcaaacca gaaccatcag    2880
tgggaccagg tgggcaggtt cttcagtgag gtggatgcca acctgatgct ggcactctac    2940
aataactcct tctacacccg caaggagtcc tatgactatc aggcagcctg tgcccctcag    3000 cccccctggca acctgggtgc tgcacccgg ggtgtctttg tgcccaccgt tgcagatttc    3060
cttaacctgg cctggtggac ctctgctgcc gcctggtccc tgttccagca gcttctctac    3120
ggcctcatct accacagctg gttccaagca gaccccgcgg aggccgaggg gagccccgag    3180
acgcgcgaga gcagctgcgt catgaaacag acccagtact acttcggctc ggtaaacgcc    3240
tcctacaacg ccatcatcga ctgcggaaac tgctccaggc tgttccacgc gcagagactg    3300
accaacacca atcttctctt tgtggtggcc gagaagccgc tgtgcagcca gtgcgaggct    3360
ggccggctgc tgcagaagga gacgcactgc ccagcggacg gccgagca gtgtgagcta    3420 gtgcagagac cgcgataccg gagaggcccg cacatctgct tcgactacaa cgcgacagaa    3480
gatacctcag actgtggccg cggggcctcc ttccgccgt cgctgggcgt cctggtctcc    3540
ctgcaactgc tgctcctcct gggcctgccg cccggccgc agcctcaagt cctcgtccac    3600
gcctctcgcc gcctctgagc accctgcccc accccacctc cactcccacc tcacccggcc    3660
tcttcgcctt tcccacccctc ctgccccaca ctccccgcct tagagcctcg tccctccctc    3720
actgaaggac ctgagctggc caggccctga gagtctggtc tgcgccttgg gatggggagt    3780
cccaaagcgg gacgccgcag gtgtttggca cccaaatcac atctcacctc cgaactgttc    3840
```

-continued

```
aagtgtcccc agaccttct tgcctgctgg gctccccca gtgggatggg acagggaggc    3900
cacacgcact ggtgccaaaa ccaggcctct gctgccgccc ttcctggagg ctgcctatgt    3960
tgggggggac cctgcctcag ctgacccggc ctctctgccc cacccaagcc caaacttggt    4020
ttctgtgaga atagtggagg aaggtgagat ggccagtttg aagcctgtgc ctcccagctt    4080
aaatcctagc aggagagagg ctctggggca gcccccatgg gctcctgccc ctttcaggcc    4140
tacagccaca tccccaagcc caccaggtgt caggatagtc acagtgatac cagttcagac    4200
actaccccat atacacctgg aacattgagg atggaaactg gactcacatt cgacataccc    4260
cactgggcac acgcacaaac acacacacta tggggtgggg tgggtgtagg ggcttacaaa    4320
gccttacaca gggcgagggg ttggtgggag ggttggcacc tgcacactcc atctcctgct    4380
caccacctgc ctctaatctg agctgcagcc tggctggtcc tcccatttct aaagctgaat    4440
gtcaaacagt gccaaatgct ggggcagggg gtgaagaacc ctctgtccca ccctagcca    4500 ccagtgtcct ccaagtgccc cctcacctct ccaggtgctc attgtaacca tttctcacta    4560
gtgtcaggcc cccagtggga ccacatgcca ctgcctgcac cttctcggcag aggaaccccc    4620 accagacatc acctttgcc ttagcagggg tgactttgtc tctcctggct gggccatcct    4680
tccgccaatc tggcccttac acactcaggc ctgtgcccac tccctatctc cttcccaccc    4740
ctacacacac actccctgct tgcaggaggc caaactgtcc ctcccttgct gaacacacac    4800
acacacacac acacacaggt ggggactggg cacagctctt cacaccattc attctggtca    4860
tttcccccaa aggcatccca gcctggggc cagtggggaa ctgagggcaa ggggatatag    4920
tgatggggct cagatggact gggaggaggg ggagggtgat gcattaatta atggcttcgt    4980
taattaatgt catgttgctt gtcgctttct cagtgtgtgt gtgtggtcca tgcccactgc    5040
tggtgccagg gtgggtgtcc atgtgcaccc ggcctggatg ccagctgtgt ccttcggggg    5100
cgtgcgtgta actgtagtgt agtcaggtgc tcaatggaga atataaacat atacagaaaa    5160
atatatattt taagtttaaa aaacagaaaa acagacaaaa caatccccat caggtagctg    5220
tctaaccccc agctgggtct aatccttctc attacccacc cgacctggct gccctcacc    5280 ttgggctggg ggactggggg gccatttcct tttctctgcc cttttttgt tgttctattt    5340 tgtacagaca agttggaaaa acaacagcga caaaaaagtc aagaaacttt gtaaaatatc    5400
gtgtgtgtga ttccttgtaa aatatttca aatggtttat tacagaagat cagttattaa    5460
ataatgttca tattttcact tc                                            5482
```

<210> SEQ ID NO 2
<211> LENGTH: 1145
<212> TYPE: PRT
<213> ORGANISM: Homo sapiens

<400> SEQUENCE: 2

```
Met Ala Val Pro Ala Arg Thr Cys Gly Ala Ser Arg Pro Gly Pro Ala
  1               5                  10                  15

Arg Thr Ala Arg Pro Trp Pro Gly Cys Gly Pro His Pro Gly Pro Gly
             20                  25                  30

Thr Arg Arg Pro Thr Ser Gly Pro Pro Arg Pro Leu Trp Leu Leu Leu
         35                  40                  45

Pro Leu Leu Pro Leu Leu Ala Ala Pro Gly Ala Ser Ala Tyr Ser Phe
     50                  55                  60

Pro Gln Gln His Thr Met Gln His Trp Ala Arg Arg Leu Glu Gln Glu
 65                  70                  75                  80
```

```
Val Asp Gly Val Met Arg Ile Phe Gly Val Gln Gln Leu Arg Glu
                85                  90                  95

Ile Tyr Lys Asp Asn Arg Asn Leu Phe Glu Val Gln Glu Asn Glu Pro
            100                 105                 110

Gln Lys Leu Val Glu Lys Val Ala Gly Asp Ile Glu Ser Leu Leu Asp
        115                 120                 125

Arg Lys Val Gln Ala Leu Lys Arg Leu Ala Asp Ala Glu Asn Phe
    130                 135                 140

Gln Lys Ala His Arg Trp Gln Asp Asn Ile Lys Glu Glu Asp Ile Val
145                 150                 155                 160

Tyr Tyr Asp Ala Lys Ala Asp Ala Glu Leu Asp Asp Pro Glu Ser Glu
                165                 170                 175

Asp Val Glu Arg Gly Ser Lys Ala Ser Thr Leu Arg Leu Asp Phe Ile
            180                 185                 190

Glu Asp Pro Asn Phe Lys Asn Lys Val Asn Tyr Ser Tyr Ala Ala Val
        195                 200                 205

Gln Ile Pro Thr Asp Ile Tyr Lys Gly Ser Thr Val Ile Leu Asn Glu
    210                 215                 220

Leu Asn Trp Thr Glu Ala Leu Glu Asn Val Phe Met Glu Asn Arg Arg
225                 230                 235                 240

Gln Asp Pro Thr Leu Leu Trp Gln Val Phe Gly Ser Ala Thr Gly Val
                245                 250                 255

Thr Arg Tyr Tyr Pro Ala Thr Pro Trp Arg Ala Pro Lys Lys Ile Asp
            260                 265                 270

Leu Tyr Asp Val Arg Arg Arg Pro Trp Tyr Ile Gln Gly Ala Ser Ser
        275                 280                 285

Pro Lys Asp Met Val Ile Ile Val Asp Val Ser Gly Ser Val Ser Gly
    290                 295                 300

Leu Thr Leu Lys Leu Met Lys Thr Ser Val Cys Glu Met Leu Asp Thr
305                 310                 315                 320

Leu Ser Asp Asp Asp Tyr Val Asn Val Ala Ser Phe Asn Glu Lys Ala
                325                 330                 335

Gln Pro Val Ser Cys Phe Thr His Leu Val Gln Ala Asn Val Arg Asn
            340                 345                 350

Lys Lys Val Phe Lys Glu Ala Val Gln Gly Met Val Ala Lys Gly Thr
        355                 360                 365

Thr Gly Tyr Lys Ala Gly Phe Glu Tyr Ala Phe Asp Gln Leu Gln Asn
    370                 375                 380

Ser Asn Ile Thr Arg Ala Asn Cys Asn Lys Met Ile Met Met Phe Thr
385                 390                 395                 400

Asp Gly Gly Glu Asp Arg Val Gln Asp Val Phe Glu Lys Tyr Asn Trp
                405                 410                 415

Pro Asn Arg Thr Val Arg Val Phe Thr Phe Ser Val Gly Gln His Asn
            420                 425                 430

Tyr Asp Val Thr Pro Leu Gln Trp Met Ala Cys Ala Asn Lys Gly Tyr
        435                 440                 445

Tyr Phe Glu Ile Pro Ser Ile Gly Ala Ile Arg Ile Asn Thr Gln Glu
    450                 455                 460

Tyr Leu Asp Val Leu Gly Arg Pro Met Val Leu Ala Gly Lys Glu Ala
465                 470                 475                 480

Lys Gln Val Gln Trp Thr Asn Val Tyr Glu Asp Ala Leu Gly Leu Gly
                485                 490                 495
```

```
Leu Val Val Thr Gly Thr Leu Pro Val Phe Asn Leu Thr Gln Asp Gly
            500                 505                 510
Pro Gly Glu Lys Lys Asn Gln Leu Ile Leu Gly Val Met Gly Ile Asp
            515                 520                 525
Val Ala Leu Asn Asp Ile Lys Arg Leu Thr Pro Asn Tyr Thr Leu Gly
            530                 535                 540
Ala Asn Gly Tyr Val Phe Ala Ile Asp Leu Asn Gly Tyr Val Leu Leu
545                 550                 555                 560
His Pro Asn Leu Lys Pro Gln Thr Thr Asn Phe Arg Glu Pro Val Thr
            565                 570                 575
Leu Asp Phe Leu Asp Ala Glu Leu Glu Asp Glu Asn Lys Glu Glu Ile
            580                 585                 590
Arg Arg Ser Met Ile Asp Gly Asn Lys Gly His Lys Gln Ile Arg Thr
            595                 600                 605
Leu Val Lys Ser Leu Asp Glu Arg Tyr Ile Asp Glu Val Thr Arg Asn
            610                 615                 620
Tyr Thr Trp Val Pro Ile Arg Ser Thr Asn Tyr Ser Leu Gly Leu Val
625                 630                 635                 640
Leu Pro Pro Tyr Ser Thr Phe Tyr Leu Gln Ala Asn Leu Ser Asp Gln
            645                 650                 655
Ile Leu Gln Val Lys Tyr Phe Glu Phe Leu Leu Pro Ser Ser Phe Glu
            660                 665                 670
Ser Glu Gly His Val Phe Ile Ala Pro Arg Glu Tyr Cys Lys Asp Leu
            675                 680                 685
Asn Ala Ser Asp Asn Asn Thr Glu Phe Leu Lys Asn Phe Ile Glu Leu
            690                 695                 700
Met Glu Lys Val Thr Pro Asp Ser Lys Gln Cys Asn Asn Phe Leu Leu
705                 710                 715                 720
His Asn Leu Ile Leu Asp Thr Gly Ile Thr Gln Gln Leu Val Glu Arg
            725                 730                 735
Val Trp Arg Asp Gln Asp Leu Asn Thr Tyr Ser Leu Leu Ala Val Phe
            740                 745                 750
Ala Ala Thr Asp Gly Gly Ile Thr Arg Val Phe Pro Asn Lys Ala Ala
            755                 760                 765
Glu Asp Trp Thr Glu Asn Pro Glu Pro Phe Asn Ala Ser Phe Tyr Arg
            770                 775                 780
Arg Ser Leu Asp Asn His Gly Tyr Val Phe Lys Pro Pro His Gln Asp
785                 790                 795                 800
Ala Leu Leu Arg Pro Leu Glu Leu Glu Asn Asp Thr Val Gly Ile Leu
            805                 810                 815
Val Ser Thr Ala Val Glu Leu Ser Leu Gly Arg Arg Thr Leu Arg Pro
            820                 825                 830
Ala Val Val Gly Val Lys Leu Asp Leu Glu Ala Trp Ala Glu Lys Phe
            835                 840                 845
Lys Val Leu Ala Ser Asn Arg Thr His Gln Asp Gln Pro Gln Lys Cys
850                 855                 860
Gly Pro Asn Ser His Cys Glu Met Asp Cys Glu Val Asn Asn Glu Asp
865                 870                 875                 880
Leu Leu Cys Val Leu Ile Asp Asp Gly Gly Phe Leu Val Leu Ser Asn
            885                 890                 895
Gln Asn His Gln Trp Asp Gln Val Gly Arg Phe Phe Ser Glu Val Asp
            900                 905                 910
Ala Asn Leu Met Leu Ala Leu Tyr Asn Asn Ser Phe Tyr Thr Arg Lys
```

-continued

```
                915                 920                 925
Glu Ser Tyr Asp Tyr Gln Ala Ala Cys Ala Pro Gln Pro Gly Asn
    930                 935                 940

Leu Gly Ala Ala Pro Arg Gly Val Phe Val Pro Thr Val Ala Asp Phe
945                 950                 955                 960

Leu Asn Leu Ala Trp Trp Thr Ser Ala Ala Trp Ser Leu Phe Gln
            965                 970                 975

Gln Leu Leu Tyr Gly Leu Ile Tyr His Ser Trp Phe Gln Ala Asp Pro
                980                 985                 990

Ala Glu Ala Glu Gly Ser Pro Glu Thr Arg Glu Ser Ser Cys Val Met
        995                 1000                1005

Lys Gln Thr Gln Tyr Tyr Phe Gly Ser Val Asn Ala Ser Tyr Asn Ala
    1010                1015                1020

Ile Ile Asp Cys Gly Asn Cys Ser Arg Leu Phe His Ala Gln Arg Leu
1025                1030                1035                1040

Thr Asn Thr Asn Leu Leu Phe Val Val Ala Glu Lys Pro Leu Cys Ser
            1045                1050                1055

Gln Cys Glu Ala Gly Arg Leu Leu Gln Lys Glu Thr His Cys Pro Ala
        1060                1065                1070

Asp Gly Pro Glu Gln Cys Glu Leu Val Gln Arg Pro Arg Tyr Arg Arg
            1075                1080                1085

Gly Pro His Ile Cys Phe Asp Tyr Asn Ala Thr Glu Asp Thr Ser Asp
    1090                1095                1100

Cys Gly Arg Gly Ala Ser Phe Pro Pro Ser Leu Gly Val Leu Val Ser
1105                1110                1115                1120

Leu Gln Leu Leu Leu Leu Leu Gly Leu Pro Pro Arg Pro Gln Pro Gln
            1125                1130                1135

Val Leu Val His Ala Ser Arg Arg Leu
            1140                1145
```

<210> SEQ ID NO 3
<211> LENGTH: 3770
<212> TYPE: DNA
<213> ORGANISM: Homo sapiens

<400> SEQUENCE: 3

```
tactataggg cggccgcgaa ttcggcacga ggcggcgcgg agcggagcag gcagccccgc      60
gcgctcgccc accgcccgct ccgcgcagct ccccgcggcc gctctcgtcg ccgccgcagc     120
gggcgcgtcg gagggagccc agcatggccg gccgggctc gccgcgccgc gcgtcccggg     180
gggcctcggc gcttctcgct gccgcgcttc tctacgccgc gctgggggac gtggtgcgct     240
cggagcagca gataccgctc tccgtggtga agctctgggc ctcggctttt ggtggggaga     300
taaaatccat tgctgctaag tactccggtt cccagcttct gcaaaagaaa tacaaagagt     360
atgagaaaga cgttgccata gaagaaattg atggcctcca actggtaaag aagctggcaa     420
agaacatgga agagatgttt cacaagaagt ctgaggccgt caggcgtctg gtggaggctg     480
cagaagaagc acacctgaaa catgaatttg atgcagactt acagtatgaa tacttcaatg     540
ctgtgctgat aaatgaaagg gacaaagacg ggaattttttt ggagctggga aggaattca     600
tcttagcccc aaatgaccat tttaataatt tgcctgtgaa catcagtcta agtgacgtcc     660
aagtaccaac gaacatgtac aacaaagacc ctgcaattgt caatgggggtt tattggtctg     720
aatctctaaa caagtttttt gtagataact ttgaccgtga cccatctctc atatggcagt     780
actttggaag tgcaagggc ttttttaggc agtatccggg gattaaatgg gaaccagatg     840
```

-continued

```
agaatggagt cattgccttc gactgcagga accgaaaatg gtacatccag gcagcaactt      900
ctccgaaaga cgtggtcatt ttagttgacg tcagtggcag catgaaagga ctccgtctga      960
ctatcgcgaa gcaaacagtc tcatccattt tggatacact tggggatgat gacttcttca     1020
acataattgc ttataatgag gagcttcact atgtggaacc ttgcctgaat ggaactttgg     1080
tgcaagccga caggacaaac aaagagcact tcagggagca tctggacaaa cttttcgcca     1140
aaggaattgg aatgttggat atagctctga atgaggcctt caacattctg agtgatttca     1200
accacacggg acaaggaagt atctgcagtc aggccatcat gctcataact gatggggcgg     1260
tggacaccta tgatacaatc tttgcaaaat acaattggcc agatcgaaag gttcgcatct     1320
tcacatacct cattggacga gaggctgcgt ttgcagacaa tctaaagtgg atggcctgtg     1380
ccaacaaagg attttttacc cagatctcca ccttggctga tgtgcaggag aatgtcatgg     1440
aataccttca cgtgcttagc cggcccaaag tcatcgacca ggagcatgat gtggtgtgga     1500
ccgaagctta cattgacagc actctgactg atgatcaggg ccccgtcctg atgaccactg     1560
tagccatgcc tgtgtttagt aagcagaacg aaaccagatc gaagggcatt cttctgggag     1620
tggttggcac agatgtccca gtgaaagaac ttctgaagac catccccaaa tacaagttag     1680
ggattcacgg ttatgccttt gcaatcacaa ataatggrta tatcctgacg catccggaac     1740
tcaggctgct gtacgaagaa ggaaaaaagc gaaggaaacc taactatagt agcgttgacc     1800
tctctgaggt ggagtgggaa gaccgagatg acgtgttgag aaatgctatg gtgaatcgaa     1860
agacggggaa gttttccatg gaggtgaaga agacagtgga caaagggaaa cgggttttgg     1920
tgatgacaaa tgactactat tatacagaca tcaagggtac tcctttcagt ttaggtgtgg     1980
cgctttccag aggtcatggg aaatatttct tccgagggaa tgtaaccatc gaagaaggcc     2040
tgcatgactt agaacatccc gatgtgtcct ggcagatgaa atggtcctac tgcaacactg     2100
acctacaccc tgagcaccgc catctgtctc agttagaagc gattaagctc tacctaaaag     2160
gcaaagaacc tctgctccag tgtgataaag aattgatcca agaagtcctt tttgacgcgg     2220
tggtgagtgc ccccattgaa gcgtattgga ccagcctggc cctcaacaaa tctgaaaatt     2280
ctgacaaggg cgtggaggtt gccttcctcg gcactcgcac gggcctctcc agaatcaacc     2340
tgtttgtcgg ggctgagcag ctcaccaatc aggacttcct gaaagctggc gacaaggaga     2400
acatttttaa cgcagaccat ttccctctct ggtaccgaag agccgctgag cagattccag     2460
ggagcttcgt ctactcgatc ccattcagca ctggaccagt caataaaagc aatgtggtga     2520
cagcaagtac atccatccag ctcctggatg aacggaaatc tcctgtggtg gcagctgtag     2580
gcattcagat gaaacttgaa ttttccaaa ggaagttctg gactgccagc agacagtgtg     2640
cttccctgga tggcaaatgc tccatcagct gtgatgatga gactgtgaat tgttacctca     2700
tagacaataa tggatttatt ttggtgtctg aagactacac acagactgga gactttttg     2760
gtgagatcga gggagctgtg atgaacaaat gctaacaat gggctccttt aaaagaatta     2820
ccctttatga ctaccaagcc atgtgtagag ccaacaagga aagcagcgat ggcgcccatg     2880
gcctcctgga tccttataat gccttcctct ctgcagtaaa atggatcatg acagaacttg     2940
tcttgttcct ggtggaattt aacctctgca gttggtggca ctccgatatg acagctaaag     3000
cccagaaatt gaaacagacc ctggagcctt gtgatactga atatccagca ttcgtctctg     3060
agcgcaccat caaggagact acagggaata ttgcttgtga agactgctcc aagtcctttg     3120
tcatccagca aatcccaagc agcaacctgt tcatggtggt ggtggacagc agctgcctct     3180
```

-continued

| | |
|---|---|
| gtgaatctgt ggcccccatc accatggcac ccattgaaat caggtataat gaatcccttta | 3240 |
| agtgtgaacg tctaaaggcc cagaagatca gaaggcgccc agaatcttgt catggcttcc | 3300 |
| atcctgagga gaatgcaagg gagtgtgggg gtgcgccgag tctccaagcc cagacagtcc | 3360 |
| tccttctgct ccctctgctt tgatgctctc tctcaaggtg acactgactg agatgttctc | 3420 |
| ttactgactg agatgttctc ttggcatgct aaatcatgga taaactgtga accaaaatat | 3480 |
| ggtgcaacat acgagacatg aatatagtcc aaccatcagc atctcatcat gattttaaac | 3540 |
| tgtgcgtgat ataaactctt aaagatatgt tgacaaaaag ttatctatca tcttttact | 3600 |
| ttgccagtca tgcaaatgtg agtttgccac atgataatca cccttcatca gaaatgggac | 3660 |
| cgcaagtggt aggcagtgtc ccttctgctt gaaacctatt gaaaccaatt taaaactgtg | 3720 |
| tactttttaa ataaagtata ttaaaatcat aaaaaaaaaa aaaaaaaaaa | 3770 |

<210> SEQ ID NO 4
<211> LENGTH: 5073
<212> TYPE: DNA
<213> ORGANISM: Homo sapiens

<400> SEQUENCE: 4

| | |
|---|---|
| ccatgcctgc aactcccaac ttcctcgcaa accccagctc cagcagccgc tggattcccc | 60 |
| tccagccaat gcccgtggcc tgggcctttg tgcagaagac ctcggccctc ctgtggctgc | 120 |
| tgcttctagg cacctccctg tccctgcgt ggggacaggc caagattcct ctggaaacag | 180 |
| tgaagctatg ggctgacacc ttcggcgggg acctgtataa cactgtgacc aaatactcag | 240 |
| gctctctctt gctgcagaag aagtacaagg atgtggagtc cagtctgaag atcgaggagg | 300 |
| tggatggctt ggagctggtg aggaagttct cagaggacat ggagaacatg ctgcggagga | 360 |
| aagtcgaggc ggtccagaat ctggtggaag ctgccgagga ggccgacctg aaccacgaat | 420 |
| tcaatgaatc cctggtgttc gactattaca actcggtcct gatcaacgag agggacgaga | 480 |
| agggcaactt cgtggagctg ggcgccgagt tcctcctgga gtccaatgct cacttcagca | 540 |
| acctgccggt gaacacctcc atcagcagcg tgcagctgcc caccaacgtg tacaacaaag | 600 |
| acccagatat tttaaatgga gtctacatgt ctgaagcctt gaatgctgtc ttcgtggaga | 660 |
| acttccagag agacccaacg ttgacctggc aatattttgg cagtgcaact ggattcttca | 720 |
| ggatctatcc aggtataaaa tggacacctg atgagaatga agtcattact tttgactgcc | 780 |
| gaaaccgcgg ctggtacatt caagctgcta cttctcccaa ggacatagtg attttggtgg | 840 |
| acgtgagcgg cagtatgaag gggctgagga tgactattgc caagcacacc atcaccacca | 900 |
| tcttggacac cctgggggag aatgacttcg ttaatatcat agcgtacaat gactacgtcc | 960 |
| attacatcga gccttgtttt aaagggatcc tcgtccaggc ggaccgagac aatcgagagc | 1020 |
| atttcaaact gctggtggag gagttgatgg tcaaaggtgt ggggggtcgtg gaccaagccc | 1080 |
| tgagagaagc cttccagatc ctgaagcagt tccaagaggc caagcaagga agcctctgca | 1140 |
| accaggccat catgctcatc agcgacggcg ccgtggagga ctacgagccg gtgtttgaga | 1200 |
| agtataactg gccagactgt aaggtccgag ttttcactta cctcattggg agagaagtgt | 1260 |
| cttttgctga ccgcatgaag tggattgcat gcaacaacaa aggctactac acgcagatct | 1320 |
| caactgctgg cggacacccag gagaacgtga tggaatacct gcacgtgctc agccgcccca | 1380 |
| tggtcatcaa ccacgaccac gacatcatct ggacagaggc ctacatggac agcaagctcc | 1440 |
| tcagctcgca ggctcagagc ctgacactgc tcaccactgt ggccatgcca gtcttcagca | 1500 |
| agaagaacga aacgcgatcc catggcattc tcctgggtgt ggtgggctca gatgtggccc | 1560 |

-continued

```
tgagagagct gatgaagctg gcgccccggt acaagcttgg agtgcacgga tacgcctttc      1620
tgaacaccaa caatggctac atcctctccc atcccgacct ccggcccctg tacagagagg      1680
ggaagaaact aaaacccaaa cctaactaca acagtgtgga tctctccgaa gtggagtggg      1740
aagaccaggc tgaatctctg agaacagcca tgatcaatag ggaaacaggt actctctcga      1800
tggatgtgaa ggttccgatg gataaaggga agcgagttct tttcctgacc aatgactact      1860
tcttcacgga catcagcgac accccttca gtttgggggt ggtgctgtcc cggggccacg      1920
gagaatacat ccttctgggg aacacgtctg tggaagaagg cctgcatgac ttgcttcacc      1980
cagacctggc cctggccggt gactggatct actgcatcac agatattgac ccagaccacc      2040
ggaagctcag ccagctagag gccatgatcc gcttcctcac caggaaggac ccagacctgg      2100
agtgtgacga ggagctggtc cgggaggtgc tgtttgacgc ggtggtgaca gcccccatgg      2160
aagcctactg gacagcgctg gccctcaaca tgtccgagga gtctgaacac gtggtggaca      2220
tggccttcct gggcacccgg gctggcctcc tgagaagcag cttgttcgtg ggctccgaga      2280
aggtctccga caggaagttc ctgacacctg aggacgaggc cagcgtgttc accctggacc      2340
gcttcccgct gtggtaccgc caggcctcag agcatcctgc tggcagcttc gtcttcaacc      2400
tccgctgggc agaaggacca gaaagtgcgg gtgaacccat ggtggtgacg gcaagcacag      2460
ctgtggcggt gaccgtggac aagaggacag ccattgctgc agccgcgggc gtccaaatga      2520
agctggaatt cctccagcgc aaattctggg cggcaacgcg gcagtgcagc actgtggatg      2580
ggccgtgcac acagagctgc gaggacagtg atctggactg cttcgtcatc gacaacaacg      2640
ggttcattct gatctccaag aggtcccgag agacgggaag atttctgggg gaggtggatg      2700
gtgctgtcct gacccagctg ctcagcatgg gggtgttcag ccaagtgact atgtatgact      2760
atcaggccat gtgcaaaccc tcgagtcacc accacagtgc agcccagccc ctggtcagcc      2820
caatttctgc cttcttgacg gcgaccaggt ggctgctgca ggagctggtg ctgttcctgc      2880
tggagtggag tgtctggggc tcctggtacg acagaggggc cgaggccaaa agtgtcttcc      2940
atcactccca caaacacaag aagcaggacc cgctgcagcc ctgcgacacg gagtaccccg      3000
tgttcgtgta ccagccggcc atccgggagg ccaacgggat cgtggagtgc gggccctgcc      3060
agaaggtatt tgtggtgcag cagattccca acagtaacct cctcctcctg gtgacagacc      3120
ccacctgtga ctgcagcatc ttcccaccag tgctgcagga ggcgacagaa gtcaaatata      3180
atgcctctgt caaatgtgac cggatgcgct cccagaagct ccgccggcga ccagactcct      3240
gccacgcctt ccatccagag gagaatgccc aggactgcgg cggcgcctcg acacctcag      3300 cctcgccgcc cctactcctg ctgcctgtgt gtgcctgggg gctactgccc caactcctgc      3360
ggtgacacca cccagcctga cctgtgtttt ggcaaggtga tccttccaga gccatcccaa      3420
aaagtcagca ctgacatggg atgcagctaa ctgcagttgg gtcgccccca ggccaacgct      3480
cctctcaatc ctgggctggt ggccctggc tccggagaat gctggatgga acaggaaacc      3540
aatcacctgg caccactttc aagatgcttc atggtgcccg gtaccatctg ccctaggtct      3600
caacatgagc atacttctga cctaaccttc ctgtctcctc ttcgggaagc cagcgtgagc      3660
tcagcttgga ccaagacaaa ataatttagt tcttcctgta ctccagagtc cagacccagc      3720
caagaaaggg tcagttgttt ctgacccttt ctgtcggagt ggtctctggt agaacccaag      3780
gacttctggg tactgagaag cagcagcaga atgaggccaa atgcagagat gaggctaagg      3840
caagaatatg ccccaactaa agcatagatt ccccaaagtg aggctcatgg tgggaggcca      3900
```

-continued

| | | | | |
|---|---|---|---|---|
| ctcaccttcc | tagctgctgc | tcgaaaaggt | tttgactgtg | ttggggtggg ggttgggtaa | 3960 |
| gggaatggtc | aagactgaga | aaggaatgaa | atccattcag | gaaatatcga cagggctaca | 4020 |
| cgtgatgtcc | ccaaactgct | gctattgaag | aacttcccaa | aacttcttta caaagcccta | 4080 |
| aaggaaagtt | tgcatctatg | aaaagccaat | aggctgagac | atccaattgc tgcatggaaa | 4140 |
| ttgatgtaca | ttcaggggac | ggcaaaaata | gctgtaaaat | agtgaaaaag agcagtggtt | 4200 |
| gtgctctttt | ctggccaatg | atttacaaaa | gaatctactt | gactctgtcc ctggagtgaa | 4260 |
| atccttaggg | ttggaacttg | tgggaacatt | ccaacttgct | aagcagggtc cactgggagg | 4320 |
| gaagctctat | ctgggaactc | accccagcg | cacacacatc | tcccccaggg tcccaaggcc | 4380 |
| ccgcagcttc | ctcccccgac | caaaccccaa | gacctggatc | ccaggagaca acagtctcca | 4440 |
| catgagagca | acattaaggg | caaagccatg | gagaaatgtg | ggagaggccg gcctcaaatc | 4500 |
| tttccattta | acaaacccca | gtgatgggta | tggacagcat | gcagggcttt tggggcgctt | 4560 |
| ccccccgctc | ctccatcacc | ctcagcctcc | acacttcaaa | gttcaagttc aaagctgttc | 4620 |
| aagtttccta | ccagcaaata | gccctaactt | gcctctagag | taggccaaat gccaactctg | 4680 |
| taaaacacac | ttacattatc | ggttacagaa | tgtcactctt | accatcatgt cttgcaacaa | 4740 |
| ccctgtgagg | gcagtattaa | tgcccccctta | cagcagaaga | cactgcagct cgaagacagc | 4800 |
| ttaagtggca | gaataatgct | agaacagcta | aggtttacat | gtaccaaata acatgtttca | 4860 |
| gctcattcca | tcctcacaac | agcccctga | aagtgggtac | tatcattagt cccatgttat | 4920 |
| agaaactgca | gcagagttga | aaattgcctc | caaattaccg | gaagagtgta tgaagattga | 4980 |
| atgtgatgta | ttcacgtaac | atgcttgaaa | ctgcctggca | tatactaaac gctaaataaa | 5040 |
| tacatgctaa | ctgcaaaaaa | aaaaaaaaaa | aaa | | 5073 |

<210> SEQ ID NO 5
<211> LENGTH: 1085
<212> TYPE: PRT
<213> ORGANISM: Homo sapiens

<400> SEQUENCE: 5

Met Ala Gly Pro Gly Ser Pro Arg Arg Ala Ser Arg Gly Ala Ser Ala
1               5                   10                  15

Leu Leu Ala Ala Ala Leu Leu Tyr Ala Ala Leu Gly Asp Val Val Arg
            20                  25                  30

Ser Glu Gln Gln Ile Pro Leu Ser Val Val Lys Leu Trp Ala Ser Ala
        35                  40                  45

Phe Gly Gly Glu Ile Lys Ser Ile Ala Ala Lys Tyr Ser Gly Ser Gln
    50                  55                  60

Leu Leu Gln Lys Lys Tyr Lys Glu Tyr Glu Lys Asp Val Ala Ile Glu
65                  70                  75                  80

Glu Ile Asp Gly Leu Gln Leu Val Lys Lys Leu Ala Lys Asn Met Glu
                85                  90                  95

Glu Met Phe His Lys Lys Ser Glu Ala Val Arg Arg Leu Val Glu Ala
            100                 105                 110

Ala Glu Glu Ala His Leu Lys His Glu Phe Asp Ala Asp Leu Gln Tyr
        115                 120                 125

Glu Tyr Phe Asn Ala Val Leu Ile Asn Glu Arg Asp Lys Asp Gly Asn
    130                 135                 140

Phe Leu Glu Leu Gly Lys Glu Phe Ile Leu Ala Pro Asn Asp His Phe
145                 150                 155                 160

Asn Asn Leu Pro Val Asn Ile Ser Leu Ser Asp Val Gln Val Pro Thr

-continued

```
                165                 170                 175
Asn Met Tyr Asn Lys Asp Pro Ala Ile Val Asn Gly Val Tyr Trp Ser
            180                 185                 190
Glu Ser Leu Asn Lys Val Phe Val Asp Asn Phe Asp Arg Asp Pro Ser
            195                 200                 205
Leu Ile Trp Gln Tyr Phe Gly Ser Ala Lys Gly Phe Arg Gln Tyr
            210                 215                 220
Pro Gly Ile Lys Trp Glu Pro Asp Glu Asn Gly Val Ile Ala Phe Asp
225                 230                 235                 240
Cys Arg Asn Arg Lys Trp Tyr Ile Gln Ala Ala Thr Ser Pro Lys Asp
                245                 250                 255
Val Val Ile Leu Val Asp Val Ser Gly Ser Met Lys Gly Leu Arg Leu
            260                 265                 270
Thr Ile Ala Lys Gln Thr Val Ser Ser Ile Leu Asp Thr Leu Gly Asp
            275                 280                 285
Asp Asp Phe Phe Asn Ile Ile Ala Tyr Asn Glu Glu Leu His Tyr Val
            290                 295                 300
Glu Pro Cys Leu Asn Gly Thr Leu Val Gln Ala Asp Arg Thr Asn Lys
305                 310                 315                 320
Glu His Phe Arg Glu His Leu Asp Lys Leu Phe Ala Lys Gly Ile Gly
                325                 330                 335
Met Leu Asp Ile Ala Leu Asn Glu Ala Phe Asn Ile Leu Ser Asp Phe
            340                 345                 350
Asn His Thr Gly Gln Gly Ser Ile Cys Ser Gln Ala Ile Met Leu Ile
            355                 360                 365
Thr Asp Gly Ala Val Asp Thr Tyr Asp Thr Ile Phe Ala Lys Tyr Asn
            370                 375                 380
Trp Pro Asp Arg Lys Val Arg Ile Phe Thr Tyr Leu Ile Gly Arg Glu
385                 390                 395                 400
Ala Ala Phe Ala Asp Asn Leu Lys Trp Met Ala Cys Ala Asn Lys Gly
                405                 410                 415
Phe Phe Thr Gln Ile Ser Thr Leu Ala Asp Val Gln Glu Asn Val Met
            420                 425                 430
Glu Tyr Leu His Val Leu Ser Arg Pro Lys Val Ile Asp Gln Glu His
            435                 440                 445
Asp Val Val Trp Thr Glu Ala Tyr Ile Asp Ser Thr Leu Thr Asp Asp
450                 455                 460
Gln Gly Pro Val Leu Met Thr Thr Val Ala Met Pro Val Phe Ser Lys
465                 470                 475                 480
Gln Asn Glu Thr Arg Ser Lys Gly Ile Leu Leu Gly Val Val Gly Thr
                485                 490                 495
Asp Val Pro Val Lys Glu Leu Leu Lys Thr Ile Pro Lys Tyr Lys Leu
            500                 505                 510
Gly Ile His Gly Tyr Ala Phe Ala Ile Thr Asn Asn Gly Tyr Ile Leu
            515                 520                 525
Thr His Pro Glu Leu Arg Leu Leu Tyr Glu Glu Gly Lys Lys Arg Arg
            530                 535                 540
Lys Pro Asn Tyr Ser Ser Val Asp Leu Ser Glu Val Glu Trp Glu Asp
545                 550                 555                 560
Arg Asp Asp Val Leu Arg Asn Ala Met Val Asn Arg Lys Thr Gly Lys
                565                 570                 575
Phe Ser Met Glu Val Lys Lys Thr Val Asp Lys Gly Lys Arg Val Leu
            580                 585                 590
```

```
Val Met Thr Asn Asp Tyr Tyr Tyr Thr Asp Ile Lys Gly Thr Pro Phe
        595                 600                 605

Ser Leu Gly Val Ala Leu Ser Arg Gly His Gly Lys Tyr Phe Phe Arg
        610                 615                 620

Gly Asn Val Thr Ile Glu Glu Gly Leu His Asp Leu Glu His Pro Asp
625                 630                 635                 640

Val Ser Leu Ala Asp Glu Trp Ser Tyr Cys Asn Thr Asp Leu His Pro
            645                 650                 655

Glu His Arg His Leu Ser Gln Leu Glu Ala Ile Lys Leu Tyr Leu Lys
                660                 665                 670

Gly Lys Glu Pro Leu Leu Gln Cys Asp Lys Glu Leu Ile Gln Glu Val
            675                 680                 685

Leu Phe Asp Ala Val Val Ser Ala Pro Ile Glu Ala Tyr Trp Thr Ser
        690                 695                 700

Leu Ala Leu Asn Lys Ser Glu Asn Ser Asp Lys Gly Val Glu Val Ala
705                 710                 715                 720

Phe Leu Gly Thr Arg Thr Gly Leu Ser Arg Ile Asn Leu Phe Val Gly
                725                 730                 735

Ala Glu Gln Leu Thr Asn Gln Asp Phe Leu Lys Ala Gly Asp Lys Glu
            740                 745                 750

Asn Ile Phe Asn Ala Asp His Phe Pro Leu Trp Tyr Arg Arg Ala Ala
        755                 760                 765

Glu Gln Ile Pro Gly Ser Phe Val Tyr Ser Ile Pro Phe Ser Thr Gly
    770                 775                 780

Pro Val Asn Lys Ser Asn Val Val Thr Ala Ser Thr Ser Ile Gln Leu
785                 790                 795                 800

Leu Asp Glu Arg Lys Ser Pro Val Val Ala Val Gly Ile Gln Met
                805                 810                 815

Lys Leu Glu Phe Phe Gln Arg Lys Phe Trp Thr Ala Ser Arg Gln Cys
            820                 825                 830

Ala Ser Leu Asp Gly Lys Cys Ser Ile Ser Cys Asp Asp Glu Thr Val
        835                 840                 845

Asn Cys Tyr Leu Ile Asp Asn Asn Gly Phe Ile Leu Val Ser Glu Asp
850                 855                 860

Tyr Thr Gln Thr Gly Asp Phe Gly Glu Ile Glu Gly Ala Val Met
865                 870                 875                 880

Asn Lys Leu Leu Thr Met Gly Ser Phe Lys Arg Ile Thr Leu Tyr Asp
                885                 890                 895

Tyr Gln Ala Met Cys Arg Ala Asn Lys Glu Ser Ser Asp Gly Ala His
            900                 905                 910

Gly Leu Leu Asp Pro Tyr Asn Ala Phe Leu Ser Ala Val Lys Trp Ile
        915                 920                 925

Met Thr Glu Leu Val Leu Phe Leu Val Glu Phe Asn Leu Cys Ser Trp
        930                 935                 940

Trp His Ser Asp Met Thr Ala Lys Ala Gln Lys Leu Lys Gln Thr Leu
945                 950                 955                 960

Glu Pro Cys Asp Thr Glu Tyr Pro Ala Phe Val Ser Glu Arg Thr Ile
                965                 970                 975

Lys Glu Thr Thr Gly Asn Ile Ala Cys Glu Asp Cys Ser Lys Ser Phe
            980                 985                 990

Val Ile Gln Gln Ile Pro Ser Ser Asn Leu Phe Met Val Val Asp
        995                 1000                1005
```

```
Ser Ser Cys Leu Cys Glu Ser Val Ala Pro Ile Thr Met Ala Pro Ile
    1010                1015                1020

Glu Ile Arg Tyr Asn Glu Ser Leu Lys Cys Glu Arg Leu Lys Ala Gln
1025                1030                1035                1040

Lys Ile Arg Arg Arg Pro Glu Ser Cys His Gly Phe His Pro Glu Glu
                1045                1050                1055

Asn Ala Arg Glu Cys Gly Gly Ala Pro Ser Leu Gln Ala Gln Thr Val
            1060                1065                1070

Leu Leu Leu Leu Pro Leu Leu Leu Met Leu Phe Ser Arg
        1075                1080                1085

<210> SEQ ID NO 6
<211> LENGTH: 1120
<212> TYPE: PRT
<213> ORGANISM: Homo sapiens

<400> SEQUENCE: 6

Met Pro Ala Thr Pro Asn Phe Leu Ala Asn Pro Ser Ser Ser Ser Arg
  1               5                  10                  15

Trp Ile Pro Leu Gln Pro Met Pro Val Ala Trp Ala Phe Val Gln Lys
                20                  25                  30

Thr Ser Ala Leu Leu Trp Leu Leu Leu Gly Thr Ser Leu Ser Pro
         35                  40                  45

Ala Trp Gly Gln Ala Lys Ile Pro Leu Glu Thr Val Lys Leu Trp Ala
     50                  55                  60

Asp Thr Phe Gly Gly Asp Leu Tyr Asn Thr Val Thr Lys Tyr Ser Gly
 65                  70                  75                  80

Ser Leu Leu Leu Gln Lys Lys Tyr Lys Asp Val Glu Ser Ser Leu Lys
                 85                  90                  95

Ile Glu Glu Val Asp Gly Leu Glu Leu Val Arg Lys Phe Ser Glu Asp
                100                 105                 110

Met Glu Asn Met Leu Arg Arg Lys Val Glu Ala Val Gln Asn Leu Val
            115                 120                 125

Glu Ala Ala Glu Glu Ala Asp Leu Asn His Glu Phe Asn Glu Ser Leu
130                 135                 140

Val Phe Asp Tyr Tyr Asn Ser Val Leu Ile Asn Glu Arg Asp Glu Lys
145                 150                 155                 160

Gly Asn Phe Val Glu Leu Gly Ala Glu Phe Leu Leu Glu Ser Asn Ala
                165                 170                 175

His Phe Ser Asn Leu Pro Val Asn Thr Ser Ile Ser Ser Val Gln Leu
            180                 185                 190

Pro Thr Asn Val Tyr Asn Lys Asp Pro Asp Ile Leu Asn Gly Val Tyr
        195                 200                 205

Met Ser Glu Ala Leu Asn Ala Val Phe Val Glu Asn Phe Gln Arg Asp
210                 215                 220

Pro Thr Leu Thr Trp Gln Tyr Phe Gly Ser Ala Thr Gly Phe Phe Arg
225                 230                 235                 240

Ile Tyr Pro Gly Ile Lys Trp Thr Pro Asp Glu Asn Gly Val Ile Thr
                245                 250                 255

Phe Asp Cys Arg Asn Arg Gly Trp Tyr Ile Gln Ala Ala Thr Ser Pro
            260                 265                 270

Lys Asp Ile Val Ile Leu Val Asp Val Ser Gly Ser Met Lys Gly Leu
        275                 280                 285

Arg Met Thr Ile Ala Lys His Thr Ile Thr Thr Ile Leu Asp Thr Leu
290                 295                 300
```

-continued

Gly Glu Asn Asp Phe Val Asn Ile Ile Ala Tyr Asn Asp Tyr Val His
305                 310                 315                 320

Tyr Ile Glu Pro Cys Phe Lys Gly Ile Leu Val Gln Ala Asp Arg Asp
                325                 330                 335

Asn Arg Glu His Phe Lys Leu Leu Val Glu Leu Met Val Lys Gly
            340                 345                 350

Val Gly Val Val Asp Gln Ala Leu Arg Glu Ala Phe Gln Ile Leu Lys
        355                 360                 365

Gln Phe Gln Glu Ala Lys Gln Gly Ser Leu Cys Asn Gln Ala Ile Met
    370                 375                 380

Leu Ile Ser Asp Gly Ala Val Glu Asp Tyr Glu Pro Val Phe Glu Lys
385                 390                 395                 400

Tyr Asn Trp Pro Asp Cys Lys Val Arg Val Phe Thr Tyr Leu Ile Gly
                405                 410                 415

Arg Glu Val Ser Phe Ala Asp Arg Met Lys Trp Ile Ala Cys Asn Asn
            420                 425                 430

Lys Gly Tyr Tyr Thr Gln Ile Ser Thr Leu Ala Asp Thr Gln Glu Asn
        435                 440                 445

Val Met Glu Tyr Leu His Val Leu Ser Arg Pro Met Val Ile Asn His
    450                 455                 460

Asp His Asp Ile Ile Trp Thr Glu Ala Tyr Met Asp Ser Lys Leu Leu
465                 470                 475                 480

Ser Ser Gln Ala Gln Ser Leu Thr Leu Leu Thr Thr Val Ala Met Pro
                485                 490                 495

Val Phe Ser Lys Lys Asn Glu Thr Arg Ser His Gly Ile Leu Leu Gly
            500                 505                 510

Val Val Gly Ser Asp Val Ala Leu Arg Glu Leu Met Lys Leu Ala Pro
        515                 520                 525

Arg Tyr Lys Leu Gly Val His Gly Tyr Ala Phe Leu Asn Thr Asn Asn
    530                 535                 540

Gly Tyr Ile Leu Ser His Pro Asp Leu Arg Pro Leu Tyr Arg Glu Gly
545                 550                 555                 560

Lys Lys Leu Lys Pro Lys Pro Asn Tyr Asn Ser Val Asp Leu Ser Glu
                565                 570                 575

Val Glu Trp Glu Asp Gln Ala Glu Ser Leu Arg Thr Ala Met Ile Asn
            580                 585                 590

Arg Glu Thr Gly Thr Leu Ser Met Asp Val Lys Val Pro Met Asp Lys
        595                 600                 605

Gly Lys Arg Val Leu Phe Leu Thr Asn Asp Tyr Phe Phe Thr Asp Ile
    610                 615                 620

Ser Asp Thr Pro Phe Ser Leu Gly Val Val Leu Ser Arg Gly His Gly
625                 630                 635                 640

Glu Tyr Ile Leu Leu Gly Asn Thr Ser Val Glu Glu Gly Leu His Asp
                645                 650                 655

Leu Leu His Pro Asp Leu Ala Leu Ala Gly Asp Trp Ile Tyr Cys Ile
            660                 665                 670

Thr Asp Ile Asp Pro Asp His Arg Lys Leu Ser Gln Leu Glu Ala Met
        675                 680                 685

Ile Arg Phe Leu Thr Arg Lys Asp Pro Asp Leu Glu Cys Asp Glu Glu
    690                 695                 700

Leu Val Arg Glu Val Leu Phe Asp Ala Val Val Thr Ala Pro Met Glu
705                 710                 715                 720

-continued

```
Ala Tyr Trp Thr Ala Leu Ala Leu Asn Met Ser Glu Ser Glu His
            725                 730                 735
Val Val Asp Met Ala Phe Leu Gly Thr Arg Ala Gly Leu Leu Arg Ser
            740                 745                 750
Ser Leu Phe Val Gly Ser Glu Lys Val Ser Asp Arg Lys Phe Leu Thr
            755                 760                 765
Pro Glu Asp Glu Ala Ser Val Phe Thr Leu Asp Arg Phe Pro Leu Trp
770                 775                 780
Tyr Arg Gln Ala Ser Glu His Pro Ala Gly Ser Phe Val Phe Asn Leu
785                 790                 795                 800
Arg Trp Ala Glu Gly Pro Glu Ser Ala Gly Glu Pro Met Val Val Thr
                805                 810                 815
Ala Ser Thr Ala Val Ala Val Thr Val Asp Lys Arg Thr Ala Ile Ala
            820                 825                 830
Ala Ala Ala Gly Val Gln Met Lys Leu Glu Phe Leu Gln Arg Lys Phe
            835                 840                 845
Trp Ala Ala Thr Arg Gln Cys Ser Thr Val Asp Gly Pro Cys Thr Gln
850                 855                 860
Ser Cys Glu Asp Ser Asp Leu Asp Cys Phe Val Ile Asp Asn Asn Gly
865                 870                 875                 880
Phe Ile Leu Ile Ser Lys Arg Ser Arg Glu Thr Gly Arg Phe Leu Gly
                885                 890                 895
Glu Val Asp Gly Ala Val Leu Thr Gln Leu Leu Ser Met Gly Val Phe
            900                 905                 910
Ser Gln Val Thr Met Tyr Asp Tyr Gln Ala Met Cys Lys Pro Ser Ser
            915                 920                 925
His His His Ser Ala Ala Gln Pro Leu Val Ser Pro Ile Ser Ala Phe
930                 935                 940
Leu Thr Ala Thr Arg Trp Leu Leu Gln Glu Leu Val Leu Phe Leu Leu
945                 950                 955                 960
Glu Trp Ser Val Trp Gly Ser Trp Tyr Asp Arg Gly Ala Glu Ala Lys
                965                 970                 975
Ser Val Phe His His Ser His Lys His Lys Gln Asp Pro Leu Gln
            980                 985                 990
Pro Cys Asp Thr Glu Tyr Pro Val Phe Val Tyr Gln Pro Ala Ile Arg
            995                 1000                1005
Glu Ala Asn Gly Ile Val Glu Cys Gly Pro Cys Gln Lys Val Phe Val
    1010                1015                1020
Val Gln Gln Ile Pro Asn Ser Asn Leu Leu Leu Val Thr Asp Pro
1025                1030                1035                1040
Thr Cys Asp Cys Ser Ile Phe Pro Pro Val Leu Gln Glu Ala Thr Glu
                1045                1050                1055
Val Lys Tyr Asn Ala Ser Val Lys Cys Asp Arg Met Arg Ser Gln Lys
        1060                1065                1070
Leu Arg Arg Arg Pro Asp Ser Cys His Ala Phe His Pro Glu Glu Asn
        1075                1080                1085
Ala Gln Asp Cys Gly Gly Ala Ser Asp Thr Ser Ala Ser Pro Pro Leu
        1090                1095                1100
Leu Leu Leu Pro Val Cys Ala Trp Gly Leu Leu Pro Gln Leu Leu Arg
1105                1110                1115                1120
```

<210> SEQ ID NO 7
<211> LENGTH: 24
<212> TYPE: DNA

<213> ORGANISM: Homo sapiens

<400> SEQUENCE: 7
aggatggccc tggggaaaag aaga                                          24

<210> SEQ ID NO 8
<211> LENGTH: 20
<212> TYPE: DNA
<213> ORGANISM: Homo sapiens

<400> SEQUENCE: 8
atcatcaatg aggacacaga                                               20

<210> SEQ ID NO 9
<211> LENGTH: 20
<212> TYPE: DNA
<213> ORGANISM: Homo sapiens

<400> SEQUENCE: 9
agaacgaaac cagatcgaag                                               20

<210> SEQ ID NO 10
<211> LENGTH: 21
<212> TYPE: DNA
<213> ORGANISM: Homo sapiens

<400> SEQUENCE: 10
cgattcacca tagcatttct c                                             21

<210> SEQ ID NO 11
<211> LENGTH: 17
<212> TYPE: DNA
<213> ORGANISM: Homo sapiens

<400> SEQUENCE: 11
ctaccaagcc atgtgta                                                  17

<210> SEQ ID NO 12
<211> LENGTH: 20
<212> TYPE: DNA
<213> ORGANISM: Mus musculus

<400> SEQUENCE: 12
agaacgaaac taggtcaaag                                               20

<210> SEQ ID NO 13
<211> LENGTH: 21
<212> TYPE: DNA
<213> ORGANISM: Mus musculus

<400> SEQUENCE: 13
cgatttacca tggcatttcg t                                             21

<210> SEQ ID NO 14
<211> LENGTH: 254
<212> TYPE: DNA
<213> ORGANISM: Rattus rattus

<400> SEQUENCE: 14
gattcttctg ggtgtggttg gcacagatgt cccagtaaaa gagcttctga agaccatccc    60
caaatacaag ttaggaattc atggttatgc ctttgccatc acgaataatg gatacatctt   120
gacacacccg gagctcaggc ccctgtatga agaagggaaa aagcgaagga agcctaatta   180

```
cagtagtgtg gatctctcgg aagtcgagtg ggaagatcgg gatgatgtgt tacgaaatgc    240
catggtaaat cgac                                                      254

<210> SEQ ID NO 15
<211> LENGTH: 5001
<212> TYPE: DNA
<213> ORGANISM: Homo sapiens

<400> SEQUENCE: 15
ccatgcctgc aactcccaac ttcctcgcaa accccagctc cagcagccgc tggattcccc     60
tccagccaat gcccgtggcc tgggcctttg tgcagaagac ctcggccctc ctgtggctgc    120
tgcttctagg cacctccctg tcccctgcgt ggggacaggc caagattcct ctggaaacag    180
tgaagctatg ggctgacacc ttcggcgggg acctgtataa cactgtgacc aaatactcag    240
gctctctctt gctgcagaag aagtacaagg atgtggagtc cagtctgaag atcgaggagg    300
tggatggctt ggagctggtg aggaagttct cagaggacat ggagaacatg ctgcggagga    360
aagtcgaggc ggtccagaat ctggtggaag ctgccgagga ggccgacctg aaccacgaat    420
tcaatgaatc cctggtgttc gactattaca actcggtcct gatcaacgag agggacgaga    480
agggcaactt cgtggagctg gcgccagt tcctcctgga gtccaatgct cacttcagca    540
acctgccggt gaacacctcc atcagcagcg tgcagctgcc caccaacgtg tacaacaaag    600
acccagatat tttaaatgga gtctacatgt ctgaagcctt gaatgctgtc ttcgtggaga    660
acttccagag agacccaacg ttgacctggc aatattttgg cagtgcaact ggattcttca    720
ggatctatcc aggtataaaa tggacacctg atgagaatgg agtcattact tttgactgcc    780
gaaaccgcgg ctggtacatt caagctgcta cttctcccaa ggacatagtg attttggtgg    840
acgtgagcgg cagtatgaag gggctgagga tgactattgc caagcacacc atcaccacca    900
tcttggacac cctgggggag aatgactcg ttaatatcat agcgtacaat gactacgtcc    960
attacatcga gccttgtttt aaagggatcc tcgtccaggc ggaccgagac aatcgagagc   1020
atttcaaact gctggtggag gagttgatgg tcaaggtgt gggggtcgtg gaccaagccc   1080
tgagagaagc cttccagatc ctgaagcagt tccaagaggc caagcaagga agcctctgca   1140
accaggccat catgctcatc agcgacggcg ccgtggagga ctacgagccg gtgtttgaga   1200
agtataactg gccagactgt aaggtccgag ttttcactta cctcattggg agagaagtgt   1260
cttttgctga ccgcatgaag tggattgcat gcaacaacaa aggctactac acgcagatct   1320
caacgctggc ggacacccag gagaacgtga tggaatacct gcacgtgctc agccgcccca   1380
tggtcatcaa ccacgaccac gacatcatct ggacagaggc ctacatggac agcaagctcc   1440
tcagctcgca ggctcagagc ctgacactgc tcaccactgt ggccatgcca gtcttcagca   1500
agaagaacga aacgcgatcc catggcattc tcctgggtgt ggtgggctca gatgtggccc   1560
tgagagagct gatgaagctg cgcccccggt acaagcttgg agtgcacgga tacgcctttc   1620
tgaacaccaa caatggctac atcctctccc atcccgacct ccggcccctg tacagagagg   1680
ggaagaaact aaaacccaaa cctaactaca acagtgtgga tctctccgaa gtggagtggg   1740
aagaccaggc tgaatctaag cgagttcttt tcctgaccaa tgactacttc ttcacgcgaca   1800 tcagcgacac cccttttcagt ttgggggtgg tgctgtcccg ggccacggga gaatacatcc   1860
ttctggggaa cacgtctgtg gaagaaggcc tgcatgactt gcttcaccca gacctggccc   1920
tggccggtga ctggatctac tgcatcacag atattgaccc agaccaccgg aagctcagcc   1980
```

```
agctagaggc catgatccgc ttcctcacca ggaaggaccc agacctggag tgtgacgagg    2040
agctggtccg ggaggtgctg tttgacgcgg tggtgacagc ccccatggaa gcctactgga    2100
cagcgctggc cctcaacatg tccgaggagt ctgaacacgt ggtggacatg gccttcctgg    2160
gcacccgggc tggcctcctg agaagcagct tgttcgtggg ctccgagaag gtctccgaca    2220
ggaagttcct gacacctgag gacgaggcca gcgtgttcac cctggaccgc ttcccgctgt    2280
ggtaccgcca ggcctcagag catcctgctg gcagcttcgt cttcaacctc cgctgggcag    2340
aaggaccaga aagtgcgggt gaacccatgg tggtgacggc aagcacagct gtggcggtga    2400
ccgtggacaa gaggacagcc attgctgcag ccgcgggcgt ccaaatgaag ctggaattcc    2460
tccagcgcaa attctgggcg gcaacgcggc agtgcagcac tgtggatggg ccgtgcacac    2520
agagctgcga ggacagtgat ctggactgct tcgtcatcga caacaacggg ttcattctga    2580
tctccaagag gtcccgagag acgggaagat ttctggggga ggtggatggt gctgtcctga    2640
cccagctgct cagcatgggg gtgttcagcc aagtgactat gtatgactat caggccatgt    2700
gcaaaccctc gagtcaccac cacagtgcag cccagcccct ggtcagccca atttctgcct    2760
tcttgacggc gaccaggtgg ctgctgcagg agctggtgct gttcctgctg gagtggagtg    2820
tctggggctc ctggtacgac agaggggccg aggccaaaag tgtcttccat cactcccaca    2880
aacacaagaa gcaggacccg ctgcagccct gcgacacgga gtacccgtg ttcgtgtacc    2940 agccggccat ccgggaggcc aacgggatcg tggagtgcgg gccctgccag aaggtatttg    3000
tggtgcagca gattcccaac agtaacctcc tcctcctggt gacagacccc acctgtgact    3060
gcagcatctt cccaccagtg ctgcaggagg cgacagaagt caaatataat gcctctgtca    3120
aatgtgaccg gatgcgctcc cagaagctcc gccggcgacc agactcctgc cacgccttcc    3180
atccagagga gaatgcccag gactgcggcg gcgcctcgga cacctcagcc tcgccgcccc    3240
tactcctgct gcctgtgtgt gcctgggggc tactgcccca actcctgcgg tgacaccacc    3300
cagcctgacc tgtgttttgg caaggtgatc cttccagagc catcccaaaa agtcagcact    3360
gacatgggat gcagctaact gcagttgggt cgccccccagg ccaacgctcc tctcaatcct    3420
gggctggtgg cccctggctc cggagaatgc tggatggaac aggaaaccaa tcacctggca    3480
ccactttcaa gatgcttcat ggtgcccggt accatctgcc ctaggtctca acatgagcat    3540
acttctgacc taaccttcct gtctcctctt cgggaagcca gcgtgagctc agcttggacc    3600
aagacaaaat aatttagttc ttcctgtact ccagagtcca gacccagcca agaaagggtc    3660
agttgtttct gacccttct gtcggagtgg tctctggtag aacccaagga cttctgggta    3720
ctgagaagca gcagcagaat gaggccaaat gcagagatga ggctaaggca agaatatgcc    3780
ccaactaaag catagattcc ccaaagtgag gctcatggtg ggaggccact caccttccta    3840
gctgctgctc gaaaaggttt tgactgtgtt ggggtggggg ttgggtaagg gaatggtcaa    3900
gactgagaaa ggaatgaaat ccattcagga aatatcgaca gggctacacg tgatgtcccc    3960
aaactgctgc tattgaagaa cttcccaaaa cttctttaca aagccctaaa ggaaagtttg    4020
catctatgaa aagccaatag gctgagacat ccaattgctg catggaaatt gatgtacatt    4080
caggggacgg caaaaatagc tgtaaaatag tgaaaagag cagtggttgt gctctttct    4140 ggccaatgat ttacaaaaga atctacttga ctctgtccct ggagtgaaat ccttagggtt    4200
ggaacttgtg ggaacattcc aacttgctaa gcagggtcca ctgggaggga agctctatct    4260
gggaactcac ccccagcgca cacacatctc ccccagggtc ccaaggcccc gcagcttcct    4320
cccccgacca aaccccaaga cctggatccc aggagacaac agtctccaca tgagagcaac    4380
```

-continued

```
attaagggca aagccatgga gaaatgtggg agaggccggc ctcaaatctt tccatttaac    4440 aaacccagt gatgggtatg gacagcatgc agggcttttg gggcgcttcc ccccgctcct    4500
ccatcaccct cagcctccac acttcaaagt tcaagttcaa agctgttcaa gtttcctacc    4560
agcaaatagc cctaacttgc ctctagagta ggccaaatgc caactctgta aaacacactt    4620
acattatcgg ttacagaatg tcactcttac catcatgtct tgcaacaacc ctgtgagggc    4680
agtattaatg cccccttaca gcagaagaca ctgcagctcg aagacagctt aagtggcaga    4740
ataatgctag aacagctaag gtttacatgt accaaataac atgtttcagc tcattccatc    4800
ctcacaacag cccctgaaa gtgggtacta tcattagtcc catgttatag aaactgcagc    4860
agagttgaaa attgcctcca aattaccgga agagtgtatg aagattgaat gtgatgtatt    4920
cacgtaacat gcttgaaact gcctggcata tactaaacgc taaataaata catgctaact    4980
gcaaaaaaaa aaaaaaaaa a                                               5001
```

<210> SEQ ID NO 16
<211> LENGTH: 5712
<212> TYPE: DNA
<213> ORGANISM: Homo sapiens

<400> SEQUENCE: 16

```
ccatgcctgc aactcccaac ttcctcgcaa accccagctc cagcagccgc tggattcccc      60
tccagccaat gcccgtggcc tgggcctttg tgcagaagac ctcggccctc ctgtggctgc     120
tgcttctagg cacctcccctg tccctgcgt ggggacaggc caagattcct ctggaaacag     180
tgaagctatg gctgacacc ttcggcgggg acctgtataa cactgtgacc aaatactcag     240
gctctctctt gctgcagaag aagtacaagg atgtggagtc cagtctgaag atcgaggagg     300
tggatggctt ggagctggtg aggaagttct cagaggacat ggagaacatg ctgcggagga     360
aagtcgaggc ggtccagaat ctggtggaag ctgccgagga ggccgacctg aaccacgaat     420
tcaatgaatc cctggtgttc gactattaca actcggtcct gatcaacgag agggacgaga     480
agggcaactt cgtggagctg gcgccgagt tcctcctgga gtccaatgct cacttcagca     540
acctgccggt gaacacctcc atcagcagcg tgcagctgcc caccaacgtg tacaacaaag     600
acccagatat tttaaatgga gtctacatgt ctgaagcctt gaatgctgtc ttcgtggaga     660
acttccagag agacccaacg ttgacctggc aatattttgg cagtgcaact ggattcttca     720
ggatctatcc aggtataaaa tggacacctg atgagaatgg agtcattact tttgactgcc     780
gaaaccgcgg ctggtacatt caagctgcta cttctcccaa ggacatagtg attttggtgg     840
acgtgagcgg cagtatgaag gggctgagga tgactattgc caagcacacc atcaccacca     900
tcttggacac cctgggggag aatgacttcr ttaatatcat agcgtacaat gactacgtcc     960
attacatcga gccttgtttt aaagggatcc tcgtccaggc ggaccgagac aatcgagagc    1020
atttcaaact gctggtggag gagttgatgg tcaaggtgt ggggtcgtg gaccaagccc    1080 tgagagaagc cttccagatc ctgaagcagt tccaagaggc caagcaagga agcctctgca    1140
accaggccat catgctcatc agcgacggcg ccgtggagga ctacgagccg gtgtttgaga    1200
agtataactg gccagactgt aaggtccgag ttttcactta cctcattggg agagaagtgt    1260
cttttgctga ccgcatgaag tggattgcat gcaacaacaa aggctactac acgcagatct    1320
caacgctggc ggacacccag gagaacgtga tggaataacct gcacgtgctc agccgcccca    1380
tggtcatcaa ccacgaccac gacatcatct ggacagaggc ctacatggac agcaagctcc    1440
```

-continued

```
tcagctcgca ggctcagagc ctgacactgc tcaccactgt ggccatgcca gtcttcagca    1500
agaagaacga aacgcgatcc catggcattc tcctgggtgt ggtgggctca gatgtggccc    1560
tgagagagct gatgaagctg cgcccccggt acaagcttgg agtgcacgga tacgcctttc    1620
tgaacaccaa caatggctac atcctctccc atcccgacct ccggcccctg tacagagagg    1680
ggaagaaact aaaacccaaa cctaactaca acagtgtgga tctctccgaa gtggagtggg    1740
aagaccaggc tgaatctctg agaacagcca tgatcaatag ggaaacaggt actctctcga    1800
tggatgtgaa ggttccgatg gataaaggga agcgagttct tttcctgacc aatgactact    1860
tcttcacgga catcagcgac accccttttca gtttgggggt ggtgctgtcc cggggccacg    1920
gagaatacat ccttctgggg aacacgtctg tggaagaagg cctgcatgac ttgcttcacc    1980
cagacctggc cctggccggt gactggatct actgcatcac agatattgac ccagaccacc    2040
ggaagctcag ccagctagag gccatgatcc gcttcctcac caggaaggac ccagacctgg    2100
agtgtgacga ggagctggtc cgggaggtgc tgtttgacgc ggtggtgaca gcccccatgg    2160
aagcctactg gacagcgctg gccctcaaca tgtccgagga gtctgaacac gtggtggaca    2220
tggccttcct gggcacccgg gctggcctcc tgagaagcag cttgttcgtg ggctccgaga    2280
aggtctccga caggaagttc ctgacacctg aggacgaggc cagcgtgttc accctggacc    2340
gcttcccgct gtggtaccgc caggcctcag agcatcctgc tggcagcttc gtcttcaacc    2400
tccgctgggc agaaggacca gaaagtgcgg gtgaacccat ggtggtgacg gcaagcacag    2460
ctgtggcggt gaccgtggac aagaggacag ccattgctgc agccgcgggc gtccaaatga    2520
agctggaatt cctccagcgc aaattctggg cggcaacgcg gcagtgcagc actgtggatg    2580
ggccgtgcac acagagctgc gaggacagtg atctggactg cttcgtcatc gacaacaacg    2640
ggttcattct gatctccaag aggtcccgag agacgggaag atttctgggg gaggtggatg    2700
gtgctgtcct gacccagctg ctcagcatgg gggtgttcag ccaagtgact atgtatgact    2760
atcaggccat gtgcaaaccc tcgagtcacc accacagtgc agcccagccc ctggtcagcc    2820
caatttctgc cttcttgacg gcgaccaggt ggctgctgca ggagctggtg cttgtgagtg    2880
ggggtagaca cggggctggt ggaggctgca tgcgagggtg gcttaggagg gtgtccttga    2940
tcaggaggct gcaaggtctc caggacaacc cacttgctac caagaccccg gggaaggagg    3000
gcacaatccc tgggcatgga cgccacctct tccctgcatg cttgcccctg ggagggacct    3060
cattgctcaa ccagagccct caagcaggga agggtgtc ctggaggaga ggggatgggc    3120
cggggctgt cagggatact ccagctcctt gggaacccaa gtcggaggg ctcagaggtc    3180
tccgagattc agtcctgtgt ctgacaggtt cctgctggag tggagtgtct ggggctcctg    3240
gtacgacaga ggggccgagg gtgagtgcac ggagctgcag ggccatgtgc tgaagagcag    3300
tggcattttg gtccactaac gtgagaccat tccctgtggg gtgggtgaca gtggggatag    3360
gtgaccctga agcatcgttg ttcacatctc acctgcgtg gccttctctc atcacatccc    3420
tcactcctgg ctctgtgtgt gacatcatct tgggacaccg ccactccatg tgccatcatc    3480
accacccccat gacatcctgc cctcatgtgc caccatgttt tcctgtgccg tgtccaccct    3540
gtgctgggct tatgttccgg ccagccaaaa gtgtcttcca tcactcccac aaacacaaga    3600
agcaggaccc gctgcagccc tgcgacacgg agtaccccgt gttcgtgtac cagccggcca    3660
tccgggaggc caacgggatc gtggagtgcg ggccctgcca aaggtatttt gtggtgcagc    3720
agattcccaa cagtaacctc ctcctcctgg tgacagaccc cacctgtgac tgcagcatct    3780
tcccaccagt gctgcaggag gcgacagaag tcaaatataa tgcctctgtc aaatgtgacc    3840
```

-continued

```
ggatgcgctc ccagaagctc cgccggcgac cagactcctg ccacgccttc catccagagg      3900
agaatgccca ggactgcggy ggcgcctcgg acacctcagc ctcgccgccc ctactcctgc      3960
tgcctgtgtg tgcctggggg ctactgcccc aactcctgcg gtgacaccac ccagcctgac      4020
ctgtgttttg gcaaggtgat ccttccagag ccatcccaaa aagtcagcac tgacatggga      4080
tgcagctaac tgcagttggg tcgccccag gccaacgctc ctctcaatcc tgggctggtg       4140
gcccctggct ccggagaatg ctggatggaa caggaaacca atcacctggc accactttca      4200
agatgcttca tggtgcccgg taccatctgc cctaggtctc aacatgagca tacttctgac      4260
ctaaccttcc tgtctcctct tcgggaagcc agcgtgagct cagcttggac caagacaaaa      4320
taatttagtt cttcctgtac tccagagtcc agacccagcc aagaaagggt cagttgtttc      4380 tgacccttc  tgtcggagtg gtctctggta aacccaagg  acttctgggt actgagaagc      4440
agcagcagaa tgaggccaaa tgcagagatg aggctaaggc aagaatatgc ccaactaaa      4500 gcatagattc cccaaagtga ggctcatggt gggaggccac tcaccttcct agctgctgct      4560
cgaaaaggtt ttgactgtgt tggggtgggg gttgggtaag ggaatggtca agactgagaa      4620
aggaatgaaa tccattcagg aaatatcgac agggctacac gtgatgtccc caaactgctg      4680
ctattgaaga acttcccaaa acttctttac aaagccctaa aggaaagttt gcatctatga      4740
aaagccaata ggctgagaca tccaattgct gcatggaaat tgatgtacat tcaggggacg      4800
gcaaaaatag ctgtaaaata gtgaaaaaga gcagtggttg tgctcttttc tggccaatga      4860
tttacaaaag aatctacttg actctgtccc tggagtgaaa tccttagggt tggaacttgt      4920
gggaacattc caacttgcta agcagggtcc actgggaggg aagctctatc tgggaactca      4980
cccccagcgc acacacatct cccccagggt cccaaggccc cgcagcttcc tcccccgacc      5040
aaaccccaag acctggatcc caggagacaa cagtctccac atgagagcaa cattaagggc      5100
aaagccatgg agaaatgtgg gagaggccgg cctcaaatct ttccatttaa caaccccag       5160 tgatgggtat ggacagcatg cagggctttt ggggcgcttc ccccgctcc tccatcaccc      5220 tcagcctcca cacttcaaag ttcaagttca aagctgttca agtttcctac cagcaaatag      5280
ccctaacttg cctctagagt aggccaaatg ccaactctgt aaaacacact tacattatcg      5340
gttacagaat gtcactctta ccatcatgtc ttgcaacaac cctgtgaggg cagtattaat      5400
gcccccttac agcagaagac actgcagctc gaagacagct taagtggcag aataatgcta      5460
gaacagctaa ggtttacatg taccaaataa catgtttcag ctcattccat cctcacaaca      5520 gcccctgaa  agtgggtact atcattagtc ccatgttata gaaactgcag cagagttgaa      5580
aattgcctcc aaattaccgg aagagtgtat gaagattgaa tgtgatgtat tcacgtaaca      5640
tgcttgaaac tgcctggcat atactaaacg ctaaataaat acatgctaac tgcaaaaaaa      5700
aaaaaaaaaa aa                                                           5712
```

<210> SEQ ID NO 17
<211> LENGTH: 1096
<212> TYPE: PRT
<213> ORGANISM: Homo sapiens

<400> SEQUENCE: 17

```
Met Pro Ala Thr Pro Asn Phe Leu Ala Asn Pro Ser Ser Ser Ser Arg
 1               5                   10                  15

Trp Ile Pro Leu Gln Pro Met Pro Val Ala Trp Ala Phe Val Gln Lys
            20                  25                  30
```

-continued

```
Thr Ser Ala Leu Leu Trp Leu Leu Leu Gly Thr Ser Leu Ser Pro
         35                  40                  45

Ala Trp Gly Gln Ala Lys Ile Pro Leu Glu Thr Val Lys Leu Trp Ala
 50                  55                  60

Asp Thr Phe Gly Gly Asp Leu Tyr Asn Thr Val Thr Lys Tyr Ser Gly
 65                  70                  75                  80

Ser Leu Leu Gln Lys Lys Tyr Lys Asp Val Glu Ser Ser Leu Lys
             85                  90                  95

Ile Glu Glu Val Asp Gly Leu Glu Leu Val Arg Lys Phe Ser Glu Asp
            100                 105                 110

Met Glu Asn Met Leu Arg Arg Lys Val Glu Ala Val Gln Asn Leu Val
            115                 120                 125

Glu Ala Ala Glu Glu Ala Asp Leu Asn His Glu Phe Asn Glu Ser Leu
130                 135                 140

Val Phe Asp Tyr Tyr Asn Ser Val Leu Ile Asn Glu Arg Asp Glu Lys
145                 150                 155                 160

Gly Asn Phe Val Glu Leu Gly Ala Glu Phe Leu Leu Glu Ser Asn Ala
                165                 170                 175

His Phe Ser Asn Leu Pro Val Asn Thr Ser Ile Ser Ser Val Gln Leu
                180                 185                 190

Pro Thr Asn Val Tyr Asn Lys Asp Pro Asp Ile Leu Asn Gly Val Tyr
            195                 200                 205

Met Ser Glu Ala Leu Asn Ala Val Phe Val Glu Asn Phe Gln Arg Asp
210                 215                 220

Pro Thr Leu Thr Trp Gln Tyr Phe Gly Ser Ala Thr Gly Phe Phe Arg
225                 230                 235                 240

Ile Tyr Pro Gly Ile Lys Trp Thr Pro Asp Glu Asn Gly Val Ile Thr
                245                 250                 255

Phe Asp Cys Arg Asn Arg Gly Trp Tyr Ile Gln Ala Ala Thr Ser Pro
            260                 265                 270

Lys Asp Ile Val Ile Leu Val Asp Val Ser Gly Ser Met Lys Gly Leu
            275                 280                 285

Arg Met Thr Ile Ala Lys His Thr Ile Thr Thr Ile Leu Asp Thr Leu
290                 295                 300

Gly Glu Asn Asp Phe Val Asn Ile Ile Ala Tyr Asn Asp Tyr Val His
305                 310                 315                 320

Tyr Ile Glu Pro Cys Phe Lys Gly Ile Leu Val Gln Ala Asp Arg Asp
                325                 330                 335

Asn Arg Glu His Phe Lys Leu Val Glu Glu Leu Met Val Lys Gly
            340                 345                 350

Val Gly Val Val Asp Gln Ala Leu Arg Glu Ala Phe Gln Ile Leu Lys
            355                 360                 365

Gln Phe Gln Glu Ala Lys Gln Gly Ser Leu Cys Asn Gln Ala Ile Met
370                 375                 380

Leu Ile Ser Asp Gly Ala Val Glu Asp Tyr Glu Pro Val Phe Glu Lys
385                 390                 395                 400

Tyr Asn Trp Pro Asp Cys Lys Val Arg Val Phe Thr Tyr Leu Ile Gly
                405                 410                 415

Arg Glu Val Ser Phe Ala Asp Arg Met Lys Trp Ile Ala Cys Asn Asn
            420                 425                 430

Lys Gly Tyr Tyr Thr Gln Ile Ser Thr Leu Ala Asp Thr Gln Glu Asn
            435                 440                 445

Val Met Glu Tyr Leu His Val Leu Ser Arg Pro Met Val Ile Asn His
```

-continued

```
            450                 455                 460
Asp His Asp Ile Ile Trp Thr Glu Ala Tyr Met Asp Ser Lys Leu Leu
465                 470                 475                 480

Ser Ser Gln Ala Gln Ser Leu Thr Leu Leu Thr Thr Val Ala Met Pro
                485                 490                 495

Val Phe Ser Lys Lys Asn Glu Thr Arg Ser His Gly Ile Leu Leu Gly
                500                 505                 510

Val Val Gly Ser Asp Val Ala Leu Arg Glu Leu Met Lys Leu Ala Pro
                515                 520                 525

Arg Tyr Lys Leu Gly Val His Gly Tyr Ala Phe Leu Asn Thr Asn Asn
                530                 535                 540

Gly Tyr Ile Leu Ser His Pro Asp Leu Arg Pro Leu Tyr Arg Glu Gly
545                 550                 555                 560

Lys Lys Leu Lys Pro Lys Pro Asn Tyr Asn Ser Val Asp Leu Ser Glu
                565                 570                 575

Val Glu Trp Glu Asp Gln Ala Glu Ser Lys Arg Val Leu Phe Leu Thr
                580                 585                 590

Asn Asp Tyr Phe Phe Thr Asp Ile Ser Asp Thr Pro Phe Ser Leu Gly
                595                 600                 605

Val Val Leu Ser Arg Gly His Gly Glu Tyr Ile Leu Leu Gly Asn Thr
                610                 615                 620

Ser Val Glu Glu Gly Leu His Asp Leu Leu His Pro Asp Leu Ala Leu
625                 630                 635                 640

Ala Gly Asp Trp Ile Tyr Cys Ile Thr Asp Ile Asp Pro Asp His Arg
                645                 650                 655

Lys Leu Ser Gln Leu Glu Ala Met Ile Arg Phe Leu Thr Arg Lys Asp
                660                 665                 670

Pro Asp Leu Glu Cys Asp Glu Glu Leu Val Arg Glu Val Leu Phe Asp
                675                 680                 685

Ala Val Val Thr Ala Pro Met Glu Ala Tyr Trp Thr Ala Leu Ala Leu
                690                 695                 700

Asn Met Ser Glu Glu Ser Glu His Val Val Asp Met Ala Phe Leu Gly
705                 710                 715                 720

Thr Arg Ala Gly Leu Leu Arg Ser Ser Leu Phe Val Gly Ser Glu Lys
                725                 730                 735

Val Ser Asp Arg Lys Phe Leu Thr Pro Glu Asp Glu Ala Ser Val Phe
                740                 745                 750

Thr Leu Asp Arg Phe Pro Leu Trp Tyr Arg Gln Ala Ser Glu His Pro
                755                 760                 765

Ala Gly Ser Phe Val Phe Asn Leu Arg Trp Ala Glu Gly Pro Glu Ser
770                 775                 780

Ala Gly Glu Pro Met Val Val Thr Ala Ser Thr Ala Val Ala Val Thr
785                 790                 795                 800

Val Asp Lys Arg Thr Ala Ile Ala Ala Ala Gly Val Gln Met Lys
                805                 810                 815

Leu Glu Phe Leu Gln Arg Lys Phe Trp Ala Ala Thr Arg Gln Cys Ser
                820                 825                 830

Thr Val Asp Gly Pro Cys Thr Gln Ser Cys Glu Asp Ser Asp Leu Asp
                835                 840                 845

Cys Phe Val Ile Asp Asn Asn Gly Phe Ile Leu Ile Ser Lys Arg Ser
                850                 855                 860

Arg Glu Thr Gly Arg Phe Leu Gly Glu Val Asp Gly Ala Val Leu Thr
865                 870                 875                 880
```

-continued

Gln Leu Leu Ser Met Gly Val Phe Ser Gln Val Thr Met Tyr Asp Tyr
             885                 890                 895
Gln Ala Met Cys Lys Pro Ser Ser His His Ser Ala Ala Gln Pro
    900                 905                 910
Leu Val Ser Pro Ile Ser Ala Phe Leu Thr Ala Thr Arg Trp Leu Leu
            915                 920                 925
Gln Glu Leu Val Leu Phe Leu Leu Glu Trp Ser Val Trp Gly Ser Trp
        930                 935                 940
Tyr Asp Arg Gly Ala Glu Ala Lys Ser Val Phe His His Ser His Lys
945                 950                 955                 960
His Lys Lys Gln Asp Pro Leu Gln Pro Cys Asp Thr Glu Tyr Pro Val
                965                 970                 975
Phe Val Tyr Gln Pro Ala Ile Arg Glu Ala Asn Gly Ile Val Glu Cys
            980                 985                 990
Gly Pro Cys Gln Lys Val Phe Val Val Gln Gln Ile Pro Asn Ser Asn
        995                 1000                1005
Leu Leu Leu Leu Val Thr Asp Pro Thr Cys Asp Cys Ser Ile Phe Pro
  1010                1015                1020
Pro Val Leu Gln Glu Ala Thr Glu Val Lys Tyr Asn Ala Ser Val Lys
1025                1030                1035                1040
Cys Asp Arg Met Arg Ser Gln Lys Leu Arg Arg Pro Asp Ser Cys
            1045                1050                1055
His Ala Phe His Pro Glu Glu Asn Ala Gln Asp Cys Gly Gly Ala Ser
        1060                1065                1070
Asp Thr Ser Ala Ser Pro Pro Leu Leu Leu Pro Val Cys Ala Trp
    1075                1080                1085
Gly Leu Leu Pro Gln Leu Leu Arg
        1090                1095

<210> SEQ ID NO 18
<211> LENGTH: 18
<212> TYPE: DNA
<213> ORGANISM: Homo sapiens

<400> SEQUENCE: 18
gcgaggacag tgatctgg                                                18

<210> SEQ ID NO 19
<211> LENGTH: 20
<212> TYPE: DNA
<213> ORGANISM: Homo sapiens

<400> SEQUENCE: 19
gggtcctcgt tcttgtgttt                                              20

<210> SEQ ID NO 20
<211> LENGTH: 20
<212> TYPE: DNA
<213> ORGANISM: Homo sapiens

<400> SEQUENCE: 20
tcagcctcca cacttcaaag                                              20

<210> SEQ ID NO 21
<211> LENGTH: 19
<212> TYPE: DNA
<213> ORGANISM: Homo sapiens

```
<400> SEQUENCE: 21
tccgcctgga cgaggatcc                                              19

<210> SEQ ID NO 22
<211> LENGTH: 20
<212> TYPE: DNA
<213> ORGANISM: Homo sapiens

<400> SEQUENCE: 22
gtgtccaaga tggtggtgat                                             20

<210> SEQ ID NO 23
<211> LENGTH: 22
<212> TYPE: DNA
<213> ORGANISM: Homo sapiens

<400> SEQUENCE: 23
atctactgca tcacagatat tg                                          22

<210> SEQ ID NO 24
<211> LENGTH: 19
<212> TYPE: DNA
<213> ORGANISM: Homo sapiens

<400> SEQUENCE: 24
ggtgaggaag cggatcatg                                              19

<210> SEQ ID NO 25
<211> LENGTH: 21
<212> TYPE: DNA
<213> ORGANISM: Mus musculus

<400> SEQUENCE: 25
ttcaacgaga aggcacagcc t                                           21

<210> SEQ ID NO 26
<211> LENGTH: 21
<212> TYPE: DNA
<213> ORGANISM: Mus musculus

<400> SEQUENCE: 26
gttggcacag gccatccact g                                           21

<210> SEQ ID NO 27
<211> LENGTH: 21
<212> TYPE: DNA
<213> ORGANISM: Mus musculus

<400> SEQUENCE: 27
aggctgtgcc ttctcgttga a                                           21

<210> SEQ ID NO 28
<211> LENGTH: 18
<212> TYPE: DNA
<213> ORGANISM: Mus musculus

<400> SEQUENCE: 28
gagcccccaa gaagatcg                                               18

<210> SEQ ID NO 29
<211> LENGTH: 18
<212> TYPE: DNA
<213> ORGANISM: Mus musculus
```

```
<400> SEQUENCE: 29
cgatcttctt gggggctc                                                       18

<210> SEQ ID NO 30
<211> LENGTH: 18
<212> TYPE: DNA
<213> ORGANISM: Mus musculus

<400> SEQUENCE: 30
cacgatgatg accatgtc                                                       18

<210> SEQ ID NO 31
<211> LENGTH: 20
<212> TYPE: DNA
<213> ORGANISM: Mus musculus

<400> SEQUENCE: 31
ggcaagaccc tacactgttg                                                     20

<210> SEQ ID NO 32
<211> LENGTH: 19
<212> TYPE: DNA
<213> ORGANISM: Mus musculus

<400> SEQUENCE: 32
cctggtaata gcgagtgac                                                      19

<210> SEQ ID NO 33
<211> LENGTH: 536
<212> TYPE: DNA
<213> ORGANISM: Mus musculus

<400> SEQUENCE: 33
aagcttctct ctcatcacca ggaggaagac atcatgtact acgatgccaa ggctgacgcc         60
gagctggtaa gtgtccccac ctttgccgta gaggatgggg agcagccaga gccacacctt        120
gttcttctgg gccacaacag tctcagctgt aaagtgggtg ttagggatcc atgctcacct        180
ttctgaactc aaccattctg tgtcgtgctt ggtcagcctc tccttgtcca cagctcccta        240
gagatccttg accctccagg gcgtgtcttc atcaccatta taggctaagc tcccctgca        300 ccatgtggag caagcagggt ggtagagtgt tggatatcag ggtggttcca tcccagtatg        360
aggggctctc tgggctccat gggagtagag aggagaaaga aatggactcc aggacctcct        420
ggggtaggta catgggagtg agacatggtg acatctaagc cctgcccagg acagtagagg        480
ctcctttcct tgtgatttgg ggaactttgc atcaagctat gtagaagaac ccatgg           536

<210> SEQ ID NO 34
<211> LENGTH: 572
<212> TYPE: DNA
<213> ORGANISM: Mus musculus

<400> SEQUENCE: 34
caggtggcct gtggctgggc cccttctctg aacactcaca gtggagacag ggctggccac         60
agnagacccc atccttctct cccttcaggg gctggggttg gtgtaacag gaacttctcc         120 ctgttttcaa cctgacacag gatggccctg gggaaaagaa ggtgagttgc ccagtgggtt        180
atctggggag gagttggcat gcctggagca ggtctgggga tggaggaggg ttagggcatg        240
ctacagattt ggcaaagcag ctctccgtat cagcagctta gccctaggc ctgggccagg         300
```

| | | |
|---|---|---|
| gggttctact atgGagttga | ctcattatag cataccttcc | cattcctttg tgtccagaac | 360 |
| cagttaatcc tgggtgtcat | gggcatcgat gtggccttga | atgacatcaa aaggctgact | 420 |
| cccaactaca cagtaagtgt | ccacctgccc ctctgccctg | gtttgctgtc catagtgaca | 480 |
| caagccagac tcagcagggg | agacatgggg actgaaagac | cgtcacagaa agacttccca | 540 |
| aagggtttgt tctgaagctg | tggacagcaa gc | | 572 |

<210> SEQ ID NO 35
<211> LENGTH: 1853
<212> TYPE: DNA
<213> ORGANISM: Mus musculus

<400> SEQUENCE: 35

| | | | |
|---|---|---|---|
| gctttcttgt ggctgcgggc | cttggagtgc atgctgagtg | ggtgagctcc ctgggggccg | 60 |
| gctgcaggct ccaggcaagc | atgctggatg ggggcccagc | tcacagctcc ctgccaccca | 120 |
| ggcggccctt ctccacaggc | acaaaccac atcagccctg | cttgctcacc gaggcctgga | 180 |
| tgagggtag gctgagatat | ttctttgatg atttagagga | gggagagcaa gaaaatctcc | 240 |
| ctggaagagc tggtgtggcc | ccacatgaga tcctgggaaa | tcaaagaaag cctgggcagg | 300 |
| cagaaagcag gggaggccat | ggagatgggt ttagcagggg | gcgaccctga acctcccaac | 360 |
| cccagccttc tgccctgccc | ctcagctacc gtcatcctca | atgagcttaa ctggacagag | 420 |
| gccctggaga acgtcttcat | tgagaaccgt aggcaagacc | ctacactgtt gtggcaagtc | 480 |
| tttggcagtg ccacgggagt | cactcgctat tacccaggta | ggcaccactg tctccctggc | 540 |
| ccatccagca cccgtcttgc | tccatctcca agcctaccca | ttctgaggtc catggggtac | 600 |
| aatgaaccag gtcaatcccc | atcactcccg cctgctccag | tcagaccctt ctgccgggcc | 660 |
| gggccccttc accccctctt | tccacagcca caccatggcg | agccccaag aagattgacc | 720 |
| tgtacgatgt cagaagacga | ccctggtgag tgagcaaggg | gggtggaggc gagacacccc | 780 |
| ctcaactccc catctctcgt | gcccgctccc ctccctccca | atatccagac ctccgagcag | 840 |
| ggcgcagcca gctctatcca | attttcattt cacacatcgc | tgccactgga aaatggatcc | 900 |
| catcgcccag gcaagccgcc | cagctgcctc tgccccacg | cgtgtcgtcc actacccagc | 960 |
| ccccccacac ccactcagaa | ctgagagcag accagggaag | gtgcttccag gggtagctag | 1020 |
| agcctccgtc aggtcagccg | gccccaccta tcatttgat | ccctggacac cccgaccctc | 1080 |
| tgctctgcct ctctcacact | actccatgat cttccctccc | tcctccatta cacagccaga | 1140 |
| ctctctggag tctctctagg | acagaggaca caagccacta | aagccttctg tccccgtgga | 1200 |
| tcacctgccc cttccccctc | acctcttgtt tacttaatga | gggaaccaga tcactcacgt | 1260 |
| cacaagaaaa aaaaaactgt | ctttttgtat tgagcatggt | ctcccccagtg cccagaccta | 1320 |
| ttccaacccc tgtagtgcgt | ggtcagtaga acacaggaa | tcaagtgggt ggaagaagga | 1380 |
| agaccccgca ggtcccggag | gtgccgtcct taactgagtc | ttctcactgg caggtatata | 1440 |
| caggggcct catcacccaa | ggacatggtc atcattgtgg | atgtgtgagt gagccttgta | 1500 |
| ggctggtggg atgggctagg | actggactct gcttcctggg | caccttatga gggaagggcg | 1560 |
| ggaaaaccct gagagcccac | atgcatgcgc cccttccgt | gcctggtttc caggagtggg | 1620 |
| agcgtgagcg gcctgactct | gaagctgatg aagacgtccg | tctgtgagat gctagacacg | 1680 |
| ctctctgatg atgactatgt | gaacgtggcc tcagtgagtg | gcaaggtggc aggcaggctg | 1740 |
| ggtaccactc acccccatcc | aacctgctcc catgacaacc | atcagccctg tacaacagct | 1800 |
| gcacactgtg tggccagcct | gaagccactc accacccccc | actgtcccca cag | 1853 |

<210> SEQ ID NO 36
<211> LENGTH: 21
<212> TYPE: DNA
<213> ORGANISM: Rattus rattus

<400> SEQUENCE: 36
gacaggacca acaaggagca c                                          21

<210> SEQ ID NO 37
<211> LENGTH: 21
<212> TYPE: DNA
<213> ORGANISM: Rattus rattus

<400> SEQUENCE: 37
gccaaccaca cccagaagaa t                                          21

<210> SEQ ID NO 38
<211> LENGTH: 21
<212> TYPE: DNA
<213> ORGANISM: Rattus rattus

<400> SEQUENCE: 38
aacgcaccat caaggagacc a                                          21

<210> SEQ ID NO 39
<211> LENGTH: 18
<212> TYPE: DNA
<213> ORGANISM: Rattus rattus

<400> SEQUENCE: 39
aggggcagca gcagcaag                                              18

<210> SEQ ID NO 40
<211> LENGTH: 516
<212> TYPE: DNA
<213> ORGANISM: Rattus rattus

<400> SEQUENCE: 40
ttcagggagc atttggacaa acttttttgcc aaagggattg gaatgctcga tattgcgctg     60
aacgaggcct tcaatgtact gagcgatttc aaccacaccg acaaggaag catttgcagc     120 caggccatta tgctcataac cgatggggca rtggacacct acgayaccat ctttgcaaag    180
tacaattggc cagagcgaaa ggttcgaatc ttcacttacc tcattggacg agaggctgct    240
tttgcagaca atctcaagtg gatrgcttgt gctaacaaag gattttttcac ccagatctcc    300 accttggctg atgtgcagga aaatgtcatg gaatacctcc atgtactcag tcgacccaaa    360
gtcatcgacc aggaacatga tgtggtgtgg accgaagcgt acatcgacag cactctccct    420
caggctcaaa agcttgctga tgatcagggc ctcgtcttga tgaccacagt ggccatgcct    480
gtgtttagta agcagaacga aactaggtca aagggc                           516

<210> SEQ ID NO 41
<211> LENGTH: 274
<212> TYPE: DNA
<213> ORGANISM: Rattus rattus

<400> SEQUENCE: 41
cagggaacat tgcttgtgaa gaytgctcca agtcctttgt catccagcaa atcccaagta     60
gcaatctgtt catggyggtg gtggacagta gctgtctctg tgagtctgtg gctcctatca    120

-continued

```
ccatggcacc cattgaaatc aggtataatg aatcccttaa gtgtgaacgg ttaaaggctc    180
agaagatcag acgacgtccg gaatcctgcc acggcttcca tcctgaggag aatgcgagag    240
agtgtggggg tgcatcaagt ctccaggccc aggt                                274
```

<210> SEQ ID NO 42
<211> LENGTH: 1096
<212> TYPE: PRT
<213> ORGANISM: Homo sapiens

<400> SEQUENCE: 42

```
Met Pro Ala Thr Pro Asn Phe Leu Ala Asn Pro Ser Ser Ser Arg
 1               5                  10                  15

Trp Ile Pro Leu Gln Pro Met Pro Val Ala Trp Ala Phe Val Gln Lys
                20                  25                  30

Thr Ser Ala Leu Leu Trp Leu Leu Leu Gly Thr Ser Leu Ser Pro
        35                  40                  45

Ala Trp Gly Gln Ala Lys Ile Pro Leu Glu Thr Val Lys Leu Trp Ala
    50                  55                  60

Asp Thr Phe Gly Gly Asp Leu Tyr Asn Thr Val Thr Lys Tyr Ser Gly
65                  70                  75                  80

Ser Leu Leu Gln Lys Lys Tyr Lys Asp Val Glu Ser Ser Leu Lys
                85                  90                  95

Ile Glu Glu Val Asp Gly Leu Glu Leu Val Arg Lys Phe Ser Glu Asp
                100                 105                 110

Met Glu Asn Met Leu Arg Arg Lys Val Glu Ala Val Gln Asn Leu Val
            115                 120                 125

Glu Ala Ala Glu Glu Ala Asp Leu Asn His Glu Phe Asn Glu Ser Leu
        130                 135                 140

Val Phe Asp Tyr Tyr Asn Ser Val Leu Ile Asn Glu Arg Asp Glu Lys
145                 150                 155                 160

Gly Asn Phe Val Glu Leu Gly Ala Glu Phe Leu Leu Glu Ser Asn Ala
                165                 170                 175

His Phe Ser Asn Leu Pro Val Asn Thr Ser Ile Ser Ser Val Gln Leu
            180                 185                 190

Pro Thr Asn Val Tyr Asn Lys Asp Pro Asp Ile Leu Asn Gly Val Tyr
        195                 200                 205

Met Ser Glu Ala Leu Asn Ala Val Phe Val Glu Asn Phe Gln Arg Asp
    210                 215                 220

Pro Thr Leu Thr Trp Gln Tyr Phe Gly Ser Ala Thr Gly Phe Phe Arg
225                 230                 235                 240

Ile Tyr Pro Gly Ile Lys Trp Thr Pro Asp Glu Asn Gly Val Ile Thr
                245                 250                 255

Phe Asp Cys Arg Asn Arg Gly Trp Tyr Ile Gln Ala Ala Thr Ser Pro
            260                 265                 270

Lys Asp Ile Val Ile Leu Val Asp Val Ser Gly Ser Met Lys Gly Leu
        275                 280                 285

Arg Met Thr Ile Ala Lys His Thr Ile Thr Thr Ile Leu Asp Thr Leu
    290                 295                 300

Gly Glu Asn Asp Phe Xaa Asn Ile Ile Ala Tyr Asn Asp Tyr Val His
305                 310                 315                 320

Tyr Ile Glu Pro Cys Phe Lys Gly Ile Leu Val Gln Ala Asp Arg Asp
                325                 330                 335

Asn Arg Glu His Phe Lys Leu Leu Val Glu Glu Leu Met Val Lys Gly
            340                 345                 350
```

-continued

```
Val Gly Val Val Asp Gln Ala Leu Arg Glu Ala Phe Gln Ile Leu Lys
            355                 360                 365
Gln Phe Gln Glu Ala Lys Gln Gly Ser Leu Cys Asn Gln Ala Ile Met
    370                 375                 380
Leu Ile Ser Asp Gly Ala Val Glu Asp Tyr Glu Pro Val Phe Glu Lys
385                 390                 395                 400
Tyr Asn Trp Pro Asp Cys Lys Val Arg Val Phe Thr Tyr Leu Ile Gly
                405                 410                 415
Arg Glu Val Ser Phe Ala Asp Arg Met Lys Trp Ile Ala Cys Asn Asn
            420                 425                 430
Lys Gly Tyr Tyr Thr Gln Ile Ser Thr Leu Ala Asp Thr Gln Glu Asn
            435                 440                 445
Val Met Glu Tyr Leu His Val Leu Ser Arg Pro Met Val Ile Asn His
    450                 455                 460
Asp His Asp Ile Ile Trp Thr Glu Ala Tyr Met Asp Ser Lys Leu Leu
465                 470                 475                 480
Ser Ser Gln Ala Gln Ser Leu Thr Leu Leu Thr Thr Val Ala Met Pro
            485                 490                 495
Val Phe Ser Lys Lys Asn Glu Thr Arg Ser His Gly Ile Leu Leu Gly
            500                 505                 510
Val Val Gly Ser Asp Val Ala Leu Arg Glu Leu Met Lys Leu Ala Pro
        515                 520                 525
Arg Tyr Lys Leu Gly Val His Gly Tyr Ala Phe Leu Asn Thr Asn Asn
        530                 535                 540
Gly Tyr Ile Leu Ser His Pro Asp Leu Arg Pro Leu Tyr Arg Glu Gly
545                 550                 555                 560
Lys Lys Leu Lys Pro Lys Pro Asn Tyr Asn Ser Val Asp Leu Ser Glu
                565                 570                 575
Val Glu Trp Glu Asp Gln Ala Glu Ser Leu Arg Thr Ala Met Ile Asn
            580                 585                 590
Arg Glu Thr Gly Thr Leu Ser Met Asp Val Lys Val Pro Met Asp Lys
            595                 600                 605
Gly Lys Arg Val Leu Phe Leu Thr Asn Asp Tyr Phe Phe Thr Asp Ile
        610                 615                 620
Ser Asp Thr Pro Phe Ser Leu Gly Val Val Leu Ser Arg Gly His Gly
625                 630                 635                 640
Glu Tyr Ile Leu Leu Gly Asn Thr Ser Val Glu Glu Gly Leu His Asp
                645                 650                 655
Leu Leu His Pro Asp Leu Ala Leu Ala Gly Asp Trp Ile Tyr Cys Ile
            660                 665                 670
Thr Asp Ile Asp Pro Asp His Arg Lys Leu Ser Gln Leu Glu Ala Met
            675                 680                 685
Ile Arg Phe Leu Thr Arg Lys Asp Pro Asp Leu Glu Cys Asp Glu Glu
        690                 695                 700
Leu Val Arg Glu Val Leu Phe Asp Ala Val Thr Ala Pro Met Glu
705                 710                 715                 720
Ala Tyr Trp Thr Ala Leu Ala Leu Asn Met Ser Glu Glu Ser Glu His
                725                 730                 735
Val Val Asp Met Ala Phe Leu Gly Thr Arg Ala Gly Leu Leu Arg Ser
            740                 745                 750
Ser Leu Phe Val Gly Ser Glu Lys Val Ser Asp Arg Lys Phe Leu Thr
        755                 760                 765
```

```
Pro Glu Asp Glu Ala Ser Val Phe Thr Leu Asp Arg Phe Pro Leu Trp
    770                 775                 780
Tyr Arg Gln Ala Ser Glu His Pro Ala Gly Ser Phe Val Phe Asn Leu
785                 790                 795                 800
Arg Trp Ala Glu Gly Pro Glu Ser Ala Gly Glu Pro Met Val Val Thr
                805                 810                 815
Ala Ser Thr Ala Val Ala Val Thr Val Asp Lys Arg Thr Ala Ile Ala
            820                 825                 830
Ala Ala Ala Gly Val Gln Met Lys Leu Glu Phe Leu Gln Arg Lys Phe
        835                 840                 845
Trp Ala Ala Thr Arg Gln Cys Ser Thr Val Asp Gly Pro Cys Thr Gln
    850                 855                 860
Ser Cys Glu Asp Ser Asp Leu Asp Cys Phe Val Ile Asp Asn Asn Gly
865                 870                 875                 880
Phe Ile Leu Ile Ser Lys Arg Ser Arg Glu Thr Gly Arg Phe Leu Gly
                885                 890                 895
Glu Val Asp Gly Ala Val Leu Thr Gln Leu Leu Ser Met Gly Val Phe
            900                 905                 910
Ser Gln Val Thr Met Tyr Asp Tyr Gln Ala Met Cys Lys Pro Ser Ser
        915                 920                 925
His His His Ser Ala Ala Gln Pro Leu Val Ser Pro Ile Ser Ala Phe
    930                 935                 940
Leu Thr Ala Thr Arg Trp Leu Leu Gln Glu Leu Val Leu Val Ser Gly
945                 950                 955                 960
Gly Arg His Gly Ala Gly Gly Gly Cys Met Arg Gly Trp Leu Arg Arg
                965                 970                 975
Val Ser Leu Ile Arg Arg Leu Gln Gly Leu Gln Asp Asn Pro Leu Ala
            980                 985                 990
Thr Lys Thr Pro Gly Lys Glu Gly Thr Ile Pro Gly His Gly Arg His
        995                 1000                1005
Leu Phe Pro Ala Cys Leu Pro Leu Gly Gly Thr Ser Leu Leu Asn Gln
    1010                1015                1020
Ser Pro Gln Ala Gly Lys Arg Val Ser Trp Arg Arg Gly Asp Gly Pro
1025                1030                1035                1040
Gly Ala Val Arg Asp Thr Pro Ala Pro Trp Glu Pro Lys Ser Gly Gly
                1045                1050                1055
Leu Arg Gly Leu Arg Asp Ser Val Leu Cys Leu Thr Gly Ser Cys Trp
            1060                1065                1070
Ser Gly Val Ser Gly Ala Pro Gly Thr Thr Glu Gly Pro Arg Val Ser
        1075                1080                1085
Ala Arg Ser Cys Arg Ala Met Cys
    1090                1095

<210> SEQ ID NO 43
<211> LENGTH: 2008
<212> TYPE: DNA
<213> ORGANISM: Homo sapiens

<400> SEQUENCE: 43
tactataggg cggccgcgaa ttcggcacga ggcggcgcgg agcggagcag gcagccccgc    60
gcgctcgccc accgcccgct ccgcgcagct ccccgcggcc gctctcgtcg ccgccgcagc   120
gggcgcgtcg gagggagccc agcatggccg gcggggctc gccgcgccgc gcgtcccggg   180
gggcctcggc gcttctcgct gccgcgcttc tctacgccgc gctgggggac gtggtgcgct   240
```

-continued

```
cggagcagca gataccgctc tccgtggtga agctctgggc ctcggctttt ggtggggaga    300
taaaatccat tgctgctaag tactccggtt cccagcttct gcaaaagaaa tacaaagagt    360
atgagaaaga cgttgccata gaagaaattg atggcctcca actggtaaag aagctggcaa    420
agaacatgga agagatgttt cacaagaagt ctgaggccgt caggcgtctg gtggaggctg    480
cagaagaagc acacctgaaa catgaatttg atgcagactt acagtatgaa acttcaatg     540 ctgtgctgat aaatgaaagg gacaaagacg ggaattttt ggagctggga aaggaattca     600
tcttagcccc aaatgaccat tttaataatt tgcctgtgaa catcagtcta agtgacgtcc    660
aagtaccaac gaacatgtac aacaaagacc ctgcaattgt caatggggtt tattggtctg    720
aatctctaaa caaagttttt gtagataact ttgaccgtga cccatctctc atatggcagt    780
actttggaag tgcaaaggc tttttaggc agtatccggg gattaaatgg gaaccagatg       840
agaatggagt cattgccttc gactgcagga accgaaaatg gtacatccag gcagcaactt    900
ctccgaaaga cgtggtcatt ttagttgacg tcagtggcag catgaaagga ctccgtctga    960
ctatcgcgaa gcaaacagtc tcatccattt tggatacact tggggatgat gacttcttca   1020
acataattgc ttataatgag gagcttcact atgtggaacc ttgcctgaat ggaactttgg   1080
tgcaagccga caggacaaac aaagagcact tcagggagca tctggacaaa cttttcgcca   1140
aaggaattgg aatgttggat atagytctga atgaggcctt caacattctg agtgatttca   1200
accacacggg acaaggaagt atctgcagtc aggccatcat gctcataact gatggggcgg   1260
tggacaccta tgatacaatc tttgcaaaat acaattggcc agatcgaaag gttcgcatct   1320
tcacataccc cattggacga gaggctgcgt ttgcagacaa tctaaagtgg atggcctgtg   1380
ccaacaaagg attttttacc cagatctcca ccttggctga tgtgcaggag aatgtcatgg   1440
aataccttca cgtgcttagc cggcccaaag tcatcgacca ggagcatgat gtggtgtgga   1500
ccgaagctta cattgacagc actctgactg atgatcaggg ccccgtcctg atgaccactg   1560
tagccatgcc tgtgtttagt aagcagaacg aaaccagatc gaagggcatt cttctgggag   1620
tggttggcac agatgtccca gtgaaagaac ttctgaagac catccccaaa tacaagttag   1680
ggattcacgg ttatgccttt gcaatcacaa ataatggata tatcctgacg catccggaac   1740
tcaggctgct gtacgaagaa ggaaaaaagc gaaggaaacc taactatagt agcgttgacc   1800
tctctgaggt ggagtgggaa gaccgagatg acgtgttgag aaatgctatg gtgaatcgaa   1860
agacggggaa gttttccatg gaggtgaaga agacagtgga caagggggta cattttctc    1920 aaacatttt gctgcttaat ttaaaacaaa ccactgtgaa aaattagctt tgaaagctat    1980
atctggaata aatatctttc gctgaagg                                       2008
```

<210> SEQ ID NO 44
<211> LENGTH: 3598
<212> TYPE: DNA
<213> ORGANISM: Homo sapiens

<400> SEQUENCE: 44

```
tactataggg cggccgcgaa ttcggcacga ggcggcgcgg agcggagcag gcagccccgc     60
gcgctcgccc accgcccgct ccgcgcagct ccccgcggcc gctctcgtcg ccgccgcagc    120
gggcgcgtcg gagggagccc agcatggccg ggccgggctc gccgcgccgc gcgtcccggg    180
gggcctcggc gcttctcgct gccgcgcttc tctacgccgc gctgggggac gtggtgcgct    240
cggagcagca gataccgctc tccgtggtga agctctgggc ctcggctttt ggtggggaga    300
taaaatccat tgctgctaag tactccggtt cccagcttct gcaaaagaaa tacaaagagt    360
```

```
atgagaaaga cgttgccata gaagaaattg atggcctcca actggtaaag aagctggcaa    420
agaacatgga agagatgttt cacaagaagt ctgaggccgt caggcgtctg gtggaggctg    480
cagaagaagc acacctgaaa catgaatttg atgcagactt acagtatgaa tacttcaatg    540
ctgtgctgat aaatgaaagg gacaaagacg ggaatttttt ggagctggga aaggaattca    600
tcttagcccc aaatgaccat tttaataatt tgcctgtgaa catcagtcta agtgacgtcc    660
aagtaccaac gaacatgtac aacaaagacc ctgcaattgt caatggggtt tattggtctg    720
aatctctaaa caaagttttt gtagataact ttgaccgtga cccatctctc atatggcagt    780
actttggaag tgcaaagggc ttttttaggc agtatccggg gattaaatgg gaaccagatg    840
agaatggagt cattgccttc gactgcagga accgaaaatg gtacatccag gcagcaactt    900
ctccgaaaga cgtggtcatt ttagttgacg tcagtggcag catgaaagga ctccgtctga    960
ctatcgcgaa gcaaacagtc tcatccattt tggatacact tggggatgat gacttcttca   1020
acataattgc ttataatgag gagcttcact atgtggaacc ttgcctgaat ggaactttgg   1080
tgcaagccga caggacaaac aaagagcact cagggagca tctggacaaa cttttcgcca   1140
aaggaattgg aatgttggat atagctctga atgaggcctt caacattctg agtgatttca   1200
accacacggg acaaggaagt atctgcagtc aggccatcat gctcataact gatggggcgg   1260
tggacaccta tgatacaatc tttgcaaaat acaattggcc agatcgaaag gttcgcatct   1320
tcacatacct cattggacga gaggctgcgt ttgcagacaa tctaaagtgg atggcctgtg   1380
ccaacaaagg attttttacc cagatctcca ccttggctga tgtgcaggag aatgtcatgg   1440
aataccttca cgtgcttagc cggcccaaag tcatcgacca ggagcatgat gtggtgtgga   1500
ccgaagctta cattgacagc actctgactg atgatcaggg ccccgtcctg atgaccactg   1560
tagccatgcc tgtgtttagt aagcagaacg aaaccagatc gaagggcatt cttctgggag   1620
tggttggcac agatgtccca gtgaaagaac ttctgaagac catccccaaa tacaagttag   1680
ggattcacgg ttatgccttt gcaatcacaa ataatggrta tatcctgacg catccggaac   1740
tcaggctgct gtacgaagaa ggaaaaaagc gaaggaaacc taactatagt agcgttgacc   1800
tctctgaggt ggagtgggaa gaccgagatg acgtgttgag aaatgctatg gtgaatcgaa   1860
agacggggaa gttttccatg gaggtgaaga agacagtgga caaagggaaa cgggttttgg   1920
tgatgacaaa tgactactat tatacagaca tcaagggtac tcctttcagt ttaggtgtgg   1980
cgctttccag aggtcatggg aaatatttct tccgagggaa tgtaaccatc gaagaaggcc   2040
tgcatgactt agaacatccc gatgtgtcct ggcagatga atggtcctac tgcaacactg   2100
acctacaccc tgagcaccgc catctgtctc agttagaagc gattaagctc tacctaaaag   2160
gcaaagaacc tctgctccag tgtgataaag aattgatcca agaagtcctt tttgacgcgg   2220
tggtgagtgc ccccattgaa gcgtattgga ccagcctggc cctcaacaaa tctgaaaatt   2280
ctgacaaggg cgtggaggtt gccttcctcg gcactcgcac gggcctctcc agaatcaacc   2340
tgtttgtcgg ggctgagcag ctcaccaatc aggacttcct gaaagctggc gacaaggaga   2400
acatttttaa cgcagaccat ttccctctct ggtaccgaag agccgctgag cagattccag   2460
ggagcttcgt ctactcgatc ccattcagca ctggaccagt caataaaagc aatgtggtga   2520
cagcaagtac atccatccag ctcctggatg aacggaaatc tcctgtgagt gcagctgtag   2580
gcattcagat gaaacttgaa ttttttccaaa ggaagttctg gactgccagc agacagtgtg   2640
cttccctgga tggcaaatgc tccatcagct gtgatgatga gactggagac ttttttggtg   2700
```

-continued

```
agatcgaggg agctgtgatg aacaaattgc taacaatggg ctcctttaaa agaattaccc    2760
tttatgacta ccaagccatg tgtagagcca acaaggaaag cagcgatggc gcccatggcc    2820
tcctggatcc cagaaattga aacagaccct ggagccttgt gatactgaat atccagcatt    2880
cgtctctgag cgcaccatca aggagactac aggaatatt gcttgtgaag actgctccaa     2940
gtcctttgtc atccagcaaa tcccaagcag caacctgttc atggtggtgg tggacagcaa    3000
ctgcctctgt gaatctgtgg cccccatcac catggcaccc attgaaatca ggtataatga    3060
atcccttaag tgtgaacgtc taaaggccca agatcagaa aggcgccag aatcttgtca      3120 tggcttccat cctgaggaga atgcaaggga gtgtgggggt gcgccgagtc tccaagccca    3180
gacagtcctc cttctgctcc ctctgctttt gatgctcttc tcaaggtgac actgactgag    3240
atgttctctt actgactgag atgttctctt ggcatgctaa atcatggata aactgtgaac    3300
caaaatatgg tgcaacatac gagacatgaa tatagtccaa ccatcagcat ctcatcatga    3360
ttttaaactg tgcgtgatat aaactcttaa agatatgttg acaaaagtt atctatcatc      3420 tttttacttt gccagtcatg caaatgtgag tttgccacat gataatcacc cttcatcaga    3480
aatgggaccg caagtggtag gcagtgtccc ttctgcttga aacctattga aaccaattta    3540
aaactgtgta cttttttaaat aaagtatatt aaaatcataa aaaaaaaaaa aaaaaaa      3598
```

<210> SEQ ID NO 45
<211> LENGTH: 27
<212> TYPE: DNA
<213> ORGANISM: Homo sapiens

<400> SEQUENCE: 45

```
ccatcctaat acgactcact atagggc                                           27
```

<210> SEQ ID NO 46
<211> LENGTH: 23
<212> TYPE: DNA
<213> ORGANISM: Homo sapiens

<400> SEQUENCE: 46

```
actcactata gggctcgagc ggc                                               23
```

<210> SEQ ID NO 47
<211> LENGTH: 1036
<212> TYPE: DNA
<213> ORGANISM: Homo sapiens

<400> SEQUENCE: 47

```
ctgtgagtgc agctgtaggc attcagatga aacttgaatt tttccaaagg aagttctgga      60
ctgccagcag acagtgtgct tccctggatg gcaaatgctc catcagctgt gatgatgaga     120
ctggagactt ttttggtgag atcgagggag ctgtgatgaa caaattgcta acaatgggct     180
cctttaaaag aattacccct tatgactacc aagccatgtg tagagccaac aaggaaagca     240
gcgatggcgc ccatggcctc ctggatccca gaaattgaaa cagaccctgg agccttgtga     300
tactgaatat ccagcattcg tctctgagcg caccatcaag gagactacag gaatattgc      360 ttgtgaagac tgctccaagt cctttgtcat ccagcaaatc ccaagcagca acctgttcat     420
ggtggtggtg gacagcaact gcctctgtga atctgtggcc cccatcacca tggcacccat    480
tgaaatcagg tataatgaat cccttaagtg tgaacgtcta aaggcccaga agatcagaag     540
gcgcccagaa tcttgtcatg gcttccatcc tgaggagaat gcaagggagt gtgggggtgc     600
gccgagtctc caagcccaga cagtcctcct tctgctccct ctgcttttga tgctcttctc     660
```

```
aaggtgacac tgactgagat gttctcttac tgactgagat gttctcttgg catgctaaat      720
catggataaa ctgtgaacca aaatatggtg caacatacga gacatgaata tagtccaacc      780
atcagcatct catcatgatt ttaaactgtg cgtgatataa actcttaaag atatgttgac      840
aaaaagttat ctatcatctt tttactttgc cagtcatgca aatgtgagtt tgccacatga      900
taatcaccct tcatcagaaa tgggaccgca agtggtaggc agtgtccctt ctgcttgaaa      960
cctattgaaa ccaatttaaa actgtgtact ttttaaataa agtatattaa aatcataaaa     1020
aaaaaaaaaa aaaaaa                                                     1036

<210> SEQ ID NO 48
<211> LENGTH: 26
<212> TYPE: DNA
<213> ORGANISM: Homo sapiens

<400> SEQUENCE: 48
ctagaggcca tgatccgctt cctcac                                           26

<210> SEQ ID NO 49
<211> LENGTH: 20
<212> TYPE: DNA
<213> ORGANISM: Homo sapiens

<400> SEQUENCE: 49
gcccacgaac aagctgcttc                                                  20
```

α-2/δ GENE

FIELD OF THE INVENTION

The present invention relates to novel genes and polypeptides derived and identified therefrom encoding polypeptides related to the alpha-2-delta ("α2δ") protein that is a subunit of the voltage-sensitive calcium channel. In particular, three human novel genes and polypeptides derived and identified therefrom encoding three human polypeptides related to the α2δ protein are disclosed. The invention also describes vectors and host cells comprising the novel genes. The invention also describes methods for using the novel genes, polypeptides, and antibodies specifically targeting the polypeptides in the detection of genetic alterations of the gene, subcellular localization of the polypeptide, gene therapy applications, diagnostics for syndromes associated with altered α2δ expression, such as neurological diseases and disorders, diabetes, cancer, and other diseases associated with α2δ expression, and binding assays in connection with chemical databases, specifically, development of proprietary screening strategies for molecules which modify α2δ protein activity.

BACKGROUND OF THE INVENTION

The voltage activated calcium channels ("VSCCs") of vertebrates have been shown to be involved in a variety of different physiological processes including muscle contraction, insulin release from the pancreas, and neurotransmitter release in the nervous system (Greenberg D. *Annals of Neurology*, 1997;42:275-82; Catterall W. A., *Trends in Neurosciences*, 1993;16:500-506; Catterall W., Epstein P. N., *Diabetologia*, 35(Suppl 2:S23-33) 1992; Birnbaumer L., et al., *Neuron.*, 1994:13; Rorsman P., et al., *Diabete. Metab.*, 1994;20:138-145).

VSCCs are most highly expressed in excitable tissues including brain, skeletal muscle, and heart. They are multi-protein complexes composed of a central α1 pore-forming subunit variably associated with beta, gamma, and/or an α2δ subunit. Nine different functional classes of VSCCs have been described, based on biophysical and pharmacological studies. These functional classes are mainly determined by the α1 subunit composition. The beta, gamma, and α2δ subunits modulate channel function, affecting the kinetics of activation and inactivation, voltage-dependence, peak amplitude, and ligand binding. Walker N., De Waard M., *Trends in Neurosciences*, 1998;21(4):148-154.

A number of compounds useful in treating various diseases in animals, including humans, are thought to exert their beneficial effects by modulating functions of voltage-dependent calcium channels. Many of these compounds bind to calcium channels and alter cellular calcium flux in response to a depolarizing signal. However, a lack of understanding of the structure of channel subunits and the genes that code for them has hampered scientists both in discerning the pharmacology of compounds that interact with calcium channels and in the ability to rationally design compounds that will interact with calcium channels to have desired therapeutic effects. The lack of understanding is due in part to the fact that it has not been possible to obtain the large amounts of highly purified channel subunits that are required to understand, at the molecular level, the nature of the subunits and their interactions with one another, with the cell membranes across which the channels allow calcium ions to pass, with calcium and other ions, and with low molecular weight compounds that affect channel function.

Further, the lack of information on genes that code for calcium channel subunits has prevented the understanding of the molecular properties of the mature calcium channel subunits and their precursor proteins (i.e., the mature subunits with signal peptides appended to the amino-terminus) and the regulation of expression of calcium channel subunits. An understanding of these properties, and of how expression of calcium channel subunits genes is regulated, may provide the basis for designing therapeutic agents which have beneficial effects through affecting calcium channel function or concentration. Furthermore, the availability of sequences of genes coding for calcium channel subunits would make possible the diagnosis of defects, which might underlie a number of diseases, in genes coding for such subunits.

Expression experiments in *Xenopus* oocytes have demonstrated that in order to produce fully functional calcium channels, the α1 and α2δ subunits must both be expressed. Absence of the α2δ subunit results in a nonfunctional channel, even though the α1 subunit, through which ions flow, is fully expressed. Indeed, not only the ion flux through these channels, but the pharmacological properties of the α1 are different in the absence of the α2δ subunit. The α2δ subunit, therefore, is a critical component of VSCCs and one that must be studied if one is to better characterize VSCC function.

A detailed understanding of VSCC operation is beginning to reveal some mechanisms for interceding in the progression of diseases associated with abnormal VSCC functions. U.S. Pat. No. 5,618,720, which issued Apr. 8, 1997, references α1 and α2δ subunits and the polynucleotide sequences that encode the subunits. The publication, however, does not disclose any additional α2δ subunits and in light of the importance of the α2δ subunit, it can be understood that the identification and characterization of new α2δ subunits and the genes encoding these subunits would advance molecular genetic and pharmacological studies to understand the relations between the structure and the function of VSCCs.

Also, a further understanding of the biochemical mechanisms behind these subunits and their effect on mammals may lead to new opportunities for treating and diagnosing diseases related to abnormal (high or low) VSCC operation. Stated another way, a better understanding of the molecular mechanisms of VSCC operation will allow improved design of therapeutic drugs that treat diseases related to abnormal VSCC expression, and specifically abnormal α2δ expression.

The cDNAs, oligonucleotides, peptides, antibodies for the α2δ proteins, which are the subject of this invention, provide a plurality of tools for studying VSCC operations in various cells and tissues and for diagnosing and selecting inhibitors or drugs with the potential to intervene in various disorders or diseases in which altered α2δ expression is implicated. Such disease states affected include epilepsy and other seizure-related syndromes, migraine, ataxia and other vestibular defects (for review, Terwindt, G M et. Al., Eur J Hum Genet 1998 July-August; 6(4):297-307), chronic pain (Backonja M, JAMA 1998 Dec. 2;280(21):1831-6), mood, sleep interference (Rowbotham M, JAMA 1998 December 2;280(21):1837-42), anxiety (Singh et al., Psychopharmocology 1996 Sep. 127(1): 1-9), ALS (Mazzini L et. Al., J Neurol Sci 1998 October, 160 Suppl 1:S57-63), multiple sclerosis (Metz L, Semin Neurol 1998;18(3):389-95), mania (Erfurth A, et al., J Psychiatr Res 1998 September-October; 32(5):261-4), tremor (Evidente V G, et al., Mov Disord 1998 September; 13(5):829-31), parkinsonism (Olson W L, et al., Am J Med 1997 January; 102(1):60-6) substance abuse/ addiction syndromes (Watson, W P et al., Neuropharmacology 1997 October; 36(10):1369-75), depression, and cancer, since at least one α2δ gene is located in a region of the genome which is thought to harbor an important tumor suppressor gene (Kok K., et al., Adv Cancer Res 1997;71: 27-92).

The α2δ gene is also thought to play a part in proliferative diseases other than cancer, such as inflammation. Treatment with compounds which bind to α2δ lead to changes in the signal transduction mechanism of certain proteins. This includes altered levels of MEK (eg, MEK1 and MEK2) which activates the MAP kinase. Inhibitors of MEK appear to mimic the analgesic activities associated with the binding of gabapentin to α2δ. Activation of MAP kinase by mitogens appears to be essential for proliferation, and constitutive activation of this kinase is sufficient to induce cellular transformation.

SUMMARY OF THE INVENTION

While the α1 subunit is known to be coded for by 9 genes, the beta subunit by 4 genes, and the gamma subunit by 2 genes, previously only two human α2δ genes were known: "α2δ-A (cDNA Accession No. M76559.1 and protein Accession No. P54289.1) and α2δ-B (cDNA SEQ ID NO 1 and protein SEQ ID NO 2). The α2δ-A gene codes for at least five different splice variants which show tissue-specific expression (Angelotti T., Hoffman F., FEBS, 1996;397:331-337). Translation of the α2δ-A gene produces a polypeptide which is post-translationally cleaved into the α2 and the δ subunits. A2 and δ are then joined by disulfide bonds (De Jongh K., JBC, 1990;265(25):14738-14741; Jay S., JBC, 1991;266(5):3287-3293). A2 is thought to be completely extracellular and is heavily glycosylated, while δ probably forms a single transmembrane domain with five intracellular amino acids at its c-terminus (Brickley K., FEBS, 1995;364: 129-133). This transmembrane domain anchors the protein to the membrane. A2δ-B is related to α2δ-A and is available in the public database, GENBANK.

The inventors, however, have discovered the existence of two new human α2δ genes, hereinafter referred to as "α2δ-C", and "α2δ-D" genes (gene names CACNA2C and CACNA2D). The present invention, therefore, relates to the isolation of polynucleotide sequences which identify and encode novel α2δ-related proteins (preferably α2δ-C and α2δ-D proteins) that are expressed in various cells and tissues, both the polynucleotide sequences for the full length genes and any splice variants and their encoded proteins. The polynucleotide sequences are identified in SEQ ID NOS 3-4 and the amino acid sequences of the α2δ proteins encoded by the three novel genes are set forth in SEQ ID NOS 5-6.

The invention also concerns a purified or isolated nucleic acid comprising at least 20 consecutive nucleotides of the nucleotide sequences SEQ ID NOS 3-4, or a nucleotide sequence complementary thereto.

A2δ-C protein of SEQ ID NO 5 is 28% identical and 48% similar at the protein level to α2δ-A protein. A2δ-C protein is 28% identical and 47% similar to α2δ-B. A2δ-C gene of SEQ ID NO 3 contains a mapped marker (known as an STS) within its nucleotide sequence which has been mapped to human chromosome 3p21.1. This region of the human genome is thought to harbor an important tumor suppressor gene, thus α2δ-C gene is a candidate tumor suppressor gene (Kersemaekers A M, et al., Br J Cancer 1998;77(2); 192-200).

A2δ-D protein of SEQ ID NO 6 is 28% identical and 47% similar at the protein level to α2δ-A protein. A2δ-D protein is 28% identical and 46% similar to α2δ-B protein. A2δ-D gene of SEQ ID 4 maps to a previously published cosmid contig on human chromosome 12 p13.3.

The unique full length polynucleotides of the present invention were initally discovered by mining the genbank database for sequences with homology to α2δ, by utilizing known nucleotide sequences and various methods known in the art, including tools provided by Compugen Systems Ltd. See Sequence Analysis Primer by Michael Gribskkov, John Devereux, Oxford University Press, 1994. After identification of expressed sequenced tags (ESTs) and full-length sequences related to α2δ-A, cloning methods were used to obtain, in hand, full-length sequences for α2δ-C and α2δ-D, see Examples 1, 2 and 3. In short, an arrayed human, kidney cDNA library obtained from Origene, was screened by PCR, using oligonucleotide primers derived from the database sequences. Clones identified from the library screen were sequenced by standard methods for verification. A summary of the sequencing information is provided in Example 3.

Analysis of the cloned sequences for α2δ-B, α2δ-C, and α2δ-D led to the identification of a conserved domain and of a number of splice variants. The conserved domain is known as a vonWillebrand factor A3 domain (Huizinga, E G, et. al., Structure 1997, Sep. 15;5(9):1147-56). This domain has been described in a large number of proteins and is thought to mediate cell adhesion. Interesting splice-variants of α2δ-C and α2δ-D were also identified. These variants result in a c-terminal truncation of the respective protein sequences. Truncation of the c-terminus may lead to the production of a soluble, secreted α2δ-C or α2δ-D protein with new functions beyond that previously described for α2δ.

The α2δ proteins are of interest because they play an important role in many disease states. In one example, α2δ-A has been shown to be a high-affinity binding target of the anti-convulsant drug gabapentin (NEURONTIN) (Gee N., JBC 1996;271:5768-5776). This property of the α2δ-A protein has the potential to have profound physiological effects. Thus, by regulating the levels or activities of α2δ-C and/or α2δ-D protein, or by modulating their function, desirable physiological effects may be obtained. Such effects may be used to treat a variety of diseases involving abnormal expression of α2δ or the abnormal expression of VSCCs (i.e., disease states include, but are not limited to epilepsy, chronic pain, anxiety, diabetes, ALS, mania, cancer, tremor, parkinsonism, migraine, ataxia, mood, sleep interference, depression, multiple sclerosis, inflammation).

The rationale for the therapeutic use of α2δ-C and/or α2δ-D proteins to design or discover treatment for these diseases is based upon the fact that gabapentin has been successfully used for treating epilepsy, chronic pain, and ALS, and has implications for use in the treatment of mania, tremor, parkinsonism, migraine, ataxia, mood, inflammation, sleep interference, and/or multiple sclerosis). Gabapentin is known to bind to α2δ-A with high affinity and this binding is thought to represent the mechanism of action of gabapentin. Therefore, gabapentin and/or other compounds which bind to α2δ-C and/or α2δ-D proteins may have similar, or related, therapeutic effects to the effects seen with gabapentin. Also, compounds which are known to have therapeutic effects on calcium channels are regulated in their affinity by the presence of α2δ. Thus, pharmacological or genetic approaches to alleviating this deficiency will have a major impact on the diseases described above.

One aspect of the invention is to provide purified α2δ-C and/or α2δ-D proteins. The purified proteins may be obtained from either recombinant cells or naturally occurring cells. The purified α2δ-C and/or α2δ-D proteins of the invention may be mammalian in origin. Primate, including human-derived α2δ-C and/or α2δ-D proteins, are examples of the various proteins specifically provided for. The invention also provides allelic variants and biologically active derivatives of naturally occurring α2δ-C and/or α2δ-D proteins.

Another aspect of the invention is to provide polynucleotides encoding the α2δ-C and/or α2δ-D proteins of the invention and to provide polynucleotides complementary to polynucleotide coding strand. The polynucleotides of the invention may be used to provide for the recombinant expression of α2δ-C and/or α2δ-D proteins. The polynucleotides of the invention may also be used for genetic therapy purposes so as to 1) treat diseases which may result from alterations of α2δ-C and/or α2δ-D genes or from alterations of cellular pathways involving α2δ-C and/or α2δ-D, 2) test for presence of a disease, or susceptibility to a disease, due to alterations or deletions in α2δ-C and/or α2δ-D, 3) analyze or alter the subcellular localization of the α2δ-C and/or α2δ-D polypeptide, 4) clone or isolate discrete classes of RNA similar to α2δ-C and/or α2δ-D genes, 5) express discrete classes of RNA in order to alter the levels of α2δ-C and/or α2δ-D genes.

The invention also relates to oligonucleotide molecules useful as probes or primers, wherein said oligonucleotide molecules hybridize specifically with any nucleotide sequence comprising or related to the α2δ-C and/or α2δ-D genes, particularly the sequences of SEQ ID NOS 3-4. These oligonucleotides are useful either as primers for use in various processes such as DNA amplification and microsequencing or as probes for DNA recognition in hybridization analyses.

A nucleic acid probe or primer according to the invention comprises at least 8 consecutive nucleotides of a polynucleotide of SEQ ID NOS 3-4, preferably from 8 to 200 consecutive nucleotides, more particularly from 10, 15, 20 or 30 to 100 consecutive nucleotides, more preferably from 10 to 90 nucleotides, and most preferably from 20 to 80 consecutive nucleotides of a polynucleotide of SEQ ID NOS 3 or 4. Preferred probes or primers of the invention comprise the oligonucleotides selected from the group consisting of the oligonucleotides set forth in the examples below.

The invention also concerns a method for the amplification of a region of the α2δ-C and/or α2δ-D genes. The method comprises the step of: contacting a test sample suspected of containing the desired α2δ-C and/or α2δ-D sequence or portion thereof with amplification reaction reagents, comprising a pair of amplification primers such as those described above, the primers being located on either side of the α2δ-C and/or α2δ-D nucleotide region to be amplified. The method may further comprise the step of detecting the amplification product. For example, the amplification product may be detected using a detection probe that can hybridize with an internal region of the amplified sequences. Alternatively, the amplification product may be detected with any of the primers used for the amplification reaction themselves, optionally in a labeled form.

The invention also concerns diagnostic kits for detecting the presence of at least one copy of a α2δ-C and/or α2δ-D DNA in a test sample, said kits containing a primer, a pair of primers or a probe according to the invention.

In a first embodiment, the kit comprises primers such as those described above, preferably forward and reverse primers which are used to amplify the α2δ-C and/or α2δ-D gene or a fragment thereof.

In a second embodiment, the kit comprises a hybridization DNA probe, that is or eventually becomes immobilized on a solid support, which is capable of hybridizing with the α2δ-C and/or α2δ-D gene or a fragment thereof. The techniques for immobilizing a nucleotide primer or probe on a solid support are well-known to the skilled person.

The kits of the present invention can also comprise optional elements including appropriate amplification reagents such as DNA polymerases when the kit comprises primers, reagents useful in hybridization reactions and reagents useful to reveal the presence of a hybridization reaction between a labeled hybridization probe and the α2δ-C and/or α2δ-D gene.

Another aspect of the invention is to provide antibodies capable of binding to α2δ-C and/or α2δ-D proteins of the invention. The antibodies may be polyclonal or monoclonal. The invention also provides methods of using the subject antibodies to detect and measure expression of α2δ-C and/or α2δ-D proteins either in vitro or in vivo, or for detecting proteins that interact with α2δ-C and/or α2δ-D proteins, or molecules that regulate any of the activities of α2δ-C and/or α2δ-D proteins.

Another aspect of the invention is to provide assays for the detection of proteins that interact with α2δ-C or α2δ-D using genetic approaches. A preferred embodiment involves the use of yeast two-hybrid approaches for this screening. (Bartel and Fields, The Yeast Two-Hybrid System, Oxford University Press, 1997)

Another aspect of the invention is to provide assays for the detection or screening of therapeutic compounds that interfere with, or mimic in any way, the interaction between α2δ-C and/or α2δ-D proteins and ligands that bind to α2δ-C and/or α2δ-D proteins.

In a first embodiment, such a method for the screening of a candidate substance comprises the following steps:
  a) providing a polypeptide comprising the amino acid sequence of SEQ ID NO 5 and/or 6, or a peptide fragment or a variant thereof,
  b) obtaining a candidate substance;
  c) bringing into contact said polypeptide with said candidate substance; and
  d) detecting the complexes formed between said polypeptide and said candidate substance.

In one embodiment of the screening method defined above, the complexes formed between the polypeptide and the candidate substance are further incubated in the presence of a polyclonal or a monoclonal antibody that specifically binds to the α2δ-C and/or α2δ-D protein of the invention or to the peptide fragment or variant thereof.

The candidate substance or molecule to be assayed for interacting with the α2δ-C and/or α2δ-D polypeptide may be of diverse nature, including, without being limited to, natural or synthetic organic compounds or molecules of biological origin such as polypeptides.

In another embodiment of the present screening method, increasing concentrations of a substance competing for binding to the α2δ-C and/or α2δ-D protein with the considered candidate substance is added, simultaneously or prior to the addition of the candidate substance or molecule, when performing step c) of said method. By this technique, the detection and optionally the quantification of the complexes formed between the α2δ-C and/or α2δ-D protein or the peptide fragment or variant thereof and the candidate substance or molecule to be screened allows the one skilled in the art to determine the affinity value of said substance or molecule for said α2δ-C and/or α2δ-D protein or the peptide fragment or variant thereof.

The invention also pertains to kits useful for performing the hereinbefore described screening method. Preferably, such kits comprise a α2δ-C and/or α2δ-D protein having the amino acid sequence of SEQ ID NO 5 and/or 6 or a peptide fragment or a variant thereof, and optionally means useful to detect the complex formed between the α2δ-C and/or α2δ-D protein or its peptide fragment or variant and the candidate substance. In a preferred embodiment the detection means consist in monoclonal or polyclonal antibodies directed against the α2δ-C and/or α2δ-D protein or a peptide fragment or a variant thereof.

The assays of the invention therefore comprise the step of measuring the effect of a compound of interest on binding between α2δ-C and/or α2δ-D protein and the ligands that bind to α2δ-C and/or α2δ-D proteins. Binding may be measured in a variety of ways, including the use of labeled α2δ-C and/or α2δ-D protein or labeled ligands. These ligands may include, but are not limited to, neutral alpha-amino acids, which have been shown to bind to α2δ-A, or therapeutic compounds such as gabapentin or related analogues.

Another aspect of the invention is to provide assays for the discovery of proteins that interact directly or indirectly with α2δ-C and/or α2δ-D proteins. The assays of the invention comprise a method for detecting such interactions in cells, or in biochemical assays. These interactions may be detected in a variety of ways, including the use of the cDNA encoding α2δ-C and/or α2δ-D proteins, or α2δ-C and/or α2δ-D proteins themselves, or fragments or modifications thereof. The assays may also comprise a method for detecting the interaction between α2δ subunits and other subunits of the calcium channel, such as α1 subunits. These assays may involve measuring the interaction between the proteins directly, or assaying the activity of a fully assembled calcium channel.

Before the present sequences, polypeptides, methods for making and using the invention are described, it is to be understood that the invention is not to be limited only to the particular sequences, polypeptides and methods described. The sequences, polypeptides and methodologies may vary, and the terminology used herein is for the purpose of describing particular embodiments. The foregoing is not intended and should not be construed as limiting the invention in any way since the scope of protection will ultimately depend upon the claims. Unless defined otherwise, all technical and scientific terms used herein have the same meaning as is commonly understood by one of skill in the art to which this invention belongs. All U.S. patents and all publications mentioned herein are incorporated in their entirety by reference thereto.

BRIEF DESCRIPTION OF THE INVENTION

FIG. 1: Fine-mapping of α2δ-B to mouse chromosome 9

FIG. 2: Human α2δ-B tissue distribution

FIG. 3: [3H] gabapentin binding activity by human α2δ-B in transiently transfected COS7

FIG. 4: Human α2δ-C tissue distribution

DETAILED DESCRIPTION OF THE INVENTION

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications Manual of Basic Technique, 2$^{nd}$ Ed.* (R. I. Freshney. 1987. Liss, Inc. New York, N.Y.), and *Gene Transfer and Expression Protocols*, pp. 109-128, ed. E. J. Murray, The Humana Press Inc., Clifton, N.J.) *Sequence Analysis Primer* (Gribskov, et al., 1994, Oxford University Press).

In one aspect, the present invention provides novel isolated and purified polynucleotides, hereinafter referred to as alpha-2-delta-C and alpha-2-delta-D ("α2δ-C", "α2δ-D") genes, encoding α2δ-C and α2δ-D proteins, wherein the polynucleotide sequences are substantially similar to those shown in SEQ ID NOS 3-4 and the polypeptide sequences are substantially similar to those shown in SEQ ID NOS 5-6. The terms "α2δ-C" and "α2δ-D" are used broadly herein. Unless noted otherwise, the terms "α2δ-C" and "α2δ-D" include any natural mammalian-derived form of α2δ-C and α2δ-D and the like. It is preferred that the terms α2δ-C and α2δ-D include all mammals, including but not limited to primates and humans.

The polynucleotides provided for may encode complete α2δ-C and/or α2δ-D proteins or portions thereof. The polynucleotides of the invention may be produced by a variety of methods including in vitro chemical synthesis using well known solid phase synthesis technique, by cloning or combinations thereof. The polynucleotide of the invention may be derived from cDNA or genomic libraries. Persons of ordinary skill in the art are familiar with the degeneracy of the genetic code and may readily design polynucleotides that encode α2δ-C and/or α2δ-D proteins that have either partial or polynucleotide sequence homology to naturally occurring polynucleotide sequences encoding α2δ-C and/or α2δ-D proteins. The polynucleotides of the invention may be single stranded or double stranded. Polynucleotide complementary to polynucleotides encoding α2δ-C and/or α2δ-D proteins are also provided.

Polynucleotides encoding an α2δ-C or α2δ-D protein can be obtained from cDNA libraries prepared from tissue believed to possess α2δ-C and/or α2δ-D protein or mRNA and to express it at a detectable level. For example, a cDNA library can be constructed by obtaining polyadenylated mRNA from a cell line known to express α2δ-C and/or α2δ-D protein, and using the mRNA as a template to synthesize double stranded cDNA.

Libraries, either cDNA or genomic, are screened with probes designed to identify the gene of interest or the protein encoded by it. For cDNA expression libraries, suitable probes include monoclonal and polyclonal antibodies that recognize and specifically bind to an α2δ-C or α2δ-D protein. For cDNA libraries, suitable probes include carefully selected oligonucleotide probes (usually of about 20-80 bases in length) that encode known or suspected portions of an α2δ-C or α2δ-D protein from the same or different species, and/or complementary or homologous cDNAs or fragments thereof that encode the same or a similar gene, and/or homologous genomic DNAs or fragments thereof.

Screening the cDNA or genomic library with the selected probe may be conducted using standard procedures as described in Chapters 10-12 of Sambrook et al., *Molecular Cloning: A Laboratory Manual*, New York, Cold Spring Harbor Laboratory Press, 1989).

A preferred method of practicing this invention is to use carefully selected oligonucleotide sequences to screen cDNA libraries from various tissues. The oligonucleotide sequences selected as probes should be sufficient in length and sufficiently unambiguous that false positives are minimized. The actual nucleotide sequence(s) is/are usually designed based on regions of an α2δ protein that have the least codon redundancy. The oligonucleotides may be degenerate at one or more positions. The use of degenerate oligonucleotides is of particular importance where a library is screened from a species in which preferential codon usage is not known.

The oligonucleotide must be labeled such that it can be detected upon hybridization to DNA in the library being screened. The preferred method of labeling is to use ATP (e.g., T32P) and polynucleotide kinase to radiolabel the 5' end of the oligonucleotide. However, other methods may be used to label the oligonucleotide, including, but not limited to, biotinylation or enzyme labeling.

cDNAs encoding α2δ proteins can also be identified and isolated by other known techniques of recombinant DNA technology, such as by direct expression cloning or by using the polymerase chain reaction (PCR) as described in U.S. Pat. No. 4,683,195, in section 14 of Sambrook, et al., *Molecular Cloning: A Laboratory Manual*, second edition, Cold Spring Harbor Laboratory Press, New York, 1989, or in Chapter 15 of *Current Protocols in Molecular Biology*, Ausubel et al. eds., Green Publishing Associates and Wiley-Interscience 1991. This method requires the use of oligonucleotide probes that will hybridize to DNA encoding an α2δ-C and/or α2δ-D protein.

As defined herein, "substantially similar" includes identical sequences, as well as deletions, substitutions or additions to a DNA, RNA or protein sequence that maintain any biologically active portion thereof of the protein product and possess any of the conserved motifs. This includes, but is not limited to, any splice variants of α2δ-C and/or α2δ-D which are found to exist. Preferably, the DNA sequences according to the invention consist essentially of the DNA sequence of SEQ ID NOS 3-4. These novel purified and isolated DNA sequences can be used to direct expression of the α2δ-C and/or α2δ-D protein and for mutational analysis of α2δ-C and/or α2δ-D protein function.

Mutated sequences according to the invention can be identified in a routine manner by those skilled in the art using the teachings provided herein, and techniques well known in the art.

In a preferred embodiment, the present invention comprises a nucleotide sequence that hybridizes to the nucleotide sequence shown in SEQ ID NOS 3-4 under high stringency hybridization conditions. As used herein, the term "high stringency hybridization conditions" refers to hybridization on a filter support at 65° C. in a low salt hybridization buffer to the probe of interest at $2 \times 10^8$ cpm/μg for between about 8 hours to 24 hours, followed by washing in 1% SDS, 20 mM phosphate buffer and 1 mM EDTA at 65° C., for between about 30 minutes to 4 hours. In a preferred embodiment, the low salt hybridization buffer comprises between, 0.5-10% SDS, and 0.05M and 0.5 M sodium phosphate. In a most preferred embodiment, the low salt hybridization buffer comprises, 7% SDS, and 0.125M sodium phosphate.

As known in the art, numerous equivalent conditions may be employed to comprise either low or high stingency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm−5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The polynucleotides of the invention have a variety of uses, some of which have been indicated or will be addressed in greater detail, infra. The particular uses for a given polynucleotide depend, in part, on the specific polynucleotide embodiment of interest. The polynucleotides of the invention may be used as hybridization probes to recover α2δ-C and/or α2δ-D proteins from genetic libraries. The polynucleotides of the invention may also be used as primers for the amplification of α2δ-C and/or α2δ-D protein encoding polynucleotides or a portion thereof through the polymerase chain reaction (PCR) and other similar amplification procedures. The polynucleotides of the invention may also be used as probes and amplification primers to detect mutations in α2δ-C and/or α2δ-D protein encoding genes that have been correlated with diseases, particularly diseases related to an altered function for α2δ-A protein. Including, but not limited to, those diseases stated above.

The invention also provides a variety of polynucleotide expression vectors, comprising α2δ-C and/or α2δ-D, or a sequence substantially similar to it subcloned into an extra-chromosomal vector. This aspect of the invention allows for in vitro expression of the α2δ-C and/or α2δ-D gene, thus permitting an analysis of α2δ-C and/or α2δ-D gene regulation and α2δ-C and/or α2δ-D protein structure and function. As used herein, the term "extra-chromosomal vector" includes, but is not limited to, plasmids, bacteriophages, cosmids, retroviruses and artificial chromosomes. In a preferred embodiment, the extra-chromosomal vector comprises an expression vector that allows for α2δ-C and/or α2δ-D protein production when the recombinant DNA molecule is inserted into a host cell. Such vectors are well known in the art and include, but are not limited to, those with the T3 or T7 polymerase promoters, the SV40 promoter, the CMV promoter, or any promoter that either can direct gene expression, or that one wishes to test for the ability to direct gene expression.

In a preferred embodiment, the subject expression vectors comprise a polynucleotide sequence encoding an α2δ-C and/or α2δ-D protein in functional combination with one or more promoter sequences so as to provide for the expression of the α2δ-C and/or α2δ-D protein (or an anti-sense copy of the sequence suitable for inhibition of expression of an endogenous gene). The vectors may comprise additional polynucleotide sequences for gene expression, regulation, or the convenient manipulation of the vector, such additional sequences include terminators, reporters, enhancers, selective markers, packaging sites, and the like. Detailed description of polynucleotide expression vectors and their use can be found in, among other places *Gene Expression Technol-* ogy: *Methods in Enzymology Volume* 185 Goeddel ed, Academic Press Inc., San Diego, Calif. (1991), *Protein Expression in Animal Cells* Roth ea., Academic Press, San Diego, Calif. (1994).

The polynucleotide expression vectors of the invention have a variety of uses. Such uses include the genetic engineering of host cells to express α2δ-C and/or α2δ-D proteins. In a further aspect, the present invention provides recombinant host cells that are stably transfected with a recombinant DNA molecule comprising α2δ-C and/or α2δ-D subcloned into an extra-chromosomal vector. The host cells of the present invention may be of any type, including, but not limited to, bacterial, yeast, mammalian cells, and *Xenopus* oocytes. Transfection of host cells with recombinant DNA molecules is well known in the art (Sambrook et al., Molecular Cloning, A Laboratory Manual, $2^{nd}$ ed., Cold Spring Harbor Press, 1989) and, as used herein, includes, but is not limited to calcium phosphate transfection, dextran sulfate transfection, electroporation, lipofection and viral infection. This aspect of the invention allows for in vitro and in vivo expression of α2δ-C and/or α2δ-D and its gene product, thus enabling high-level expression of α2δ-C and/or α2δ-D protein. In a further aspect of the invention the RNA molecules containing α2δ-C or α2δ-D can be injected into *Xenopus* oocytes along with other calcium channel subunit clones and calcium flux across the oocyte membrane can be measured using standard electrophysiological techniques.

In another aspect of the invention transgenic animals can be constructed by injection of the nucleotide sequence for α2δ-C or α2δ-D cloned in suitable expression vectors into germ cells.

Other uses of the polynucleotide expression vectors, discussed in greater detail, infra, include, their use for genetic therapy for diseases and conditions in which it may be desirable use to express α2δ-C and/or α2δ-D proteins at levels greater than naturally occurring expression levels. Alternatively, it may be desirable to use the subject vectors for anti-sense expression to reduce the naturally occurring levels of α2δ-C and/or α2δ-D protein.

A2δ-C and α2δ-D share amino acid homology to α2δ-A, thus it is very likely that they share some structural and functional characteristics with α2δ-A. A2δ-A is known to interact with other subunits of voltage-sensitive calcium channels, such as α1 and beta. When calcium channels are expressed in oocytes, a functional channel is only produced when an α2δ subunit is present. Therefore, α2δ is required for calcium channel function. In addition, α2δ-A has been shown to bind to gabapentin, a drug used to treat epilepsy, chronic pain, ALS, and potentially other neurological diseases. The mechanism of action of gabapentin is thought to be through its interaction with α2δ. Given the homology between the α2δ proteins, it is likely that α2δ-C and α2δ-D also share these functions.

The polynucleotide sequences of SEQ ID NOS 3-4 were mapped to human chromosomes using the nucleotide sequences for the cDNA from library sources (See Examples 2-3) to generate probes. The sequences were mapped to a particular chromosome or to a specific region of the chromosome using well known techniques. These include in situ hybridization to chromosomal spreads, and PCR-based mapping by amplifying DNA from standard radiation hybrid cell lines. (Verma et al (1988) Human Chromosomes: A Manual of Basic Techniques, Pergamon Press, NYC. A2δ-C of SEQ ID NO 3 maps to human chromosome 3p21.1. A2δ-D of SEQ ID NO 4 maps to a previously published cosmid contig on human chromosome 12p13.3.

In another aspect, the present invention provides a substantially purified recombinant protein comprising a polypeptide substantially similar to the α2δ-C and/or α2δ-D polypeptides shown in SEQ ID NOS 5-6. Furthermore, this aspect of the invention enables the use of α2δ protein in several in vitro assays described below. As used herein, the term "substantially similar" includes deletions, substitutions and additions to the sequences of SEQ ID NOS 5-6 introduced by any in vitro means, or any genetic alterations naturally seen in vivo. As used herein, the term "substantially purified" means that the protein should be free from detectable contaminating protein, but the α2δ-C and/or α2δ-D protein may be co-purified with an interacting protein, or as an oligomer. In a most preferred embodiment, the protein sequence according to the invention comprises an amino acid sequence of SEQ ID NOS 5-6. Mutated sequences according to the invention can be identified in a routine manner by those skilled in the art using the teachings provided herein and techniques well known in the art. This aspect of the invention provides a novel purified protein that can be used for ill vitro assays, and as a component of a pharmaceutical composition.

A2δ-C and/or α2δ-D proteins may be used to discover molecules that interfere with its activities. For example, molecules that prevent the binding of α2δ-C and/or α2δ-D to ligands such as neutral alpha-amino acids (for example (L)-leucine), or to other molecules such as other subunits of the voltage-sensitive calcium channels. Additionally, α2δ-C and/or α2δ-D proteins may be used to find other proteins with which it directly interacts, and potentially representing additional important regulators of VSCC transport.

The α2δ-C and/or α2δ-D proteins of the present invention have a putative biological activity of modulating the cellular flux of calcium, potentially including both intracellular and extracellular calcium stores. The α2δ-C and/or α2δ-D protein of the invention may be isolated from a variety of mammalian animal species. Preferred mammalian species for isolation are primates and humans. The invention also contemplates allelic variants of α2δ-C and/or α2δ-D protein. A2δ-C and/or α2δ-D proteins may be prepared from a variety of mammalian tissues. Preferably, α2δ-C and/or α2δ-D proteins are obtained from recombinant host cells genetically engineered to express significant quantities of α2δ-C and/or α2δ-D proteins. A2δ-C and/or α2δ-D proteins may be isolated from non-recombinant or recombinant cells in a variety of ways well known to a person of ordinary skill in the art.

The terms "α2δ-C protein" and "α2δ-D protein" as used herein refers not only to proteins having the amino acid residue sequence of naturally occurring α2δ-C and/or α2δ-D proteins, but also refers to functional derivatives and variants of naturally occurring α2δ-C and/or α2δ-D protein. A "functional derivative" of a native polypeptide is a compound having a qualitative biological activity in common with the native α2δ-C and/or α2δ-D protein. Thus, a functional derivative of a native α2δ-C and/or α2δ-D protein is a compound that has a qualitative biological activity in common with a native α2δ-C and/or α2δ-D protein, e.g., binding to other calcium channel subunits and modulating the flux of calcium in cells, or binding to neutral alpha-amino acids and other cognate ligands. "Functional derivatives" include, but are not limited to, fragments of native polypeptides from any animal species (including human), and derivatives of native (human and non-human) polypeptides and their fragments, provided that they have a biological activity in common with a respective native polypeptide. "Fragments" comprise regions within the sequence of a mature native polypeptide. The term "derivative" is used to define amino acid sequence and glycosylation variants, and covalent modifications of a native polypeptide, whereas the term "variant" refers to amino acid sequence and glycosylation variants within this definition. Preferably, the functional derivatives are polypeptides which have at least about 70% amino acid sequence similarity, more preferably about 80% amino acid sequence similarity, even more preferably at least 90% amino acid sequence similarity, most preferably at least about 99% amino acid sequence similarity with the sequence of a corresponding native polypeptide. Most preferably, the functional derivatives of a native α2δ-C and/or α2δ-D protein retain or mimic the region or regions within the native polypeptide sequence that directly participate in ligand binding. The phrase "functional derivative" specifically includes peptides and small organic molecules having a qualitative biological activity in common with a native α2δ-C and/or α2δ-D protein.

"Identity" or "homology" with respect to a native polypeptide and its functional derivative is defined herein as the percentage of amino acid residues in the candidate sequence that are similar to residues of a corresponding native polypeptide, after aligning the sequences and introducing gaps, if necessary, to achieve the maximum percent homology. Neither N- or C-terminal extensions nor insertions, nor alternatively-spliced variants, shall be construed as reducing identity or homology. Methods and computer programs for the alignment are well known in the art.

Amino acid sequence variants of native α2δ-C and/or α2δ-[D proteins and α2δ-C and/or α2δ-D protein fragments are prepared by methods known in the art by introducing appropriate nucleotide changes into a native or variant α2δ-C and/or α2δ-D protein encoding DNA, or by in vitro synthesis of the desired polypeptide. There are two principal variables in the construction of amino acid sequence variants: the location of the mutation site and the nature of the mutation. With the exception of naturally-occurring alleles, which do not require the manipulation of the DNA sequence encoding the α2δ-C and/or α2δ-D protein, the amino acid sequence variants of α2δ-C and/or α2δ-D protein are preferably constructed by mutating the DNA, either to arrive at an allele or an amino acid sequence variant that does not occur in nature.

Alternatively or in addition, amino acid alterations can be made at sites that differ in α2δ-C and/or α2δ-D proteins from various species, or in highly conserved regions, depending on the goal to be achieved.

Sites at such locations will typically be modified in series, e.g. by (1) substituting first with conservative choices and then with more radical selections depending upon the results achieved, (2) deleting the target residue or residues, or (3) inserting residues of the same or different class adjacent to the located site, or combinations of options 1-3.

One helpful technique is called "alanine scanning" Cunningham and Wells, *Science* 244, 1081-1085 (1989). Here, a residue or group of target residues is identified and substituted by alanine or polyalanine. Those domains demonstrating functional sensitivity to the alanine substitutions are then refined by introducing further or other substituents at or for the sites of alanine substitution.

After identifying the desired mutation(s), the gene encoding an α2δ-C and/or α2δ-D protein variant can, for example, be obtained by chemical synthesis.

More preferably, DNA encoding an α2δ-C and/or α2δ-D protein amino acid sequence variant is prepared by site-directed mutagenesis of DNA that encodes an earlier prepared variant or a nonvariant version of the α2δ-C and/or α2δ-D protein. Site-directed (site-specific) mutagenesis allows the production of α2δ-C and/or α2δ-D protein variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the techniques of site-specific mutagenesis are well known in the art, as exemplified by publications such as, Edelman et al., *DNA* 2:183 (1983). As will be appreciated, the site-specific mutagenesis technique typically employs a phage vector that exists in both a single-stranded and double-stranded form. Typical vectors useful in site-directed mutagenesis include vectors such as the M13 phage. This and other phage vectors are commercially available and their use is well known to those skilled in the art. A versatile and efficient procedure for the construction of oligodeoxyribonucleotide directed site-specific mutations in DNA fragments using M13-derived vectors was published by Zoller, M. J. and Smith, M., Nucleic Acids Res. 10, 6487-6500 [1982]). Also, plasmid vectors that contain a single-stranded phage origin of replication, Veira et al., Meth. Enzymol. 153:3 (1987)] may be employed to obtain single-stranded DNA. Alternatively, nucleotide substitutions are introduced by synthesizing the appropriate DNA fragment in vitro, and amplifying it by PCR procedures known in the art.

In general, site-specific mutagenesis may be performed by obtaining either a double-stranded or a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* USA 75, 5765 (1978). This primer is then annealed with the single-stranded protein sequence-containing vector, and subjected to DNA-polymerizing enzymes such as, *E. coli* polymerase I Klenow fragment, to complete the synthesis of the mutation-bearing strand. Thus, a heteroduplex is formed wherein one strand encodes the original non-mutated sequence and the second strand bears the desires mutation. This heteroduplex vector is then used to transform appropriate host cells such as HB101 cells, and clones are selected that include recombinant vectors bearing the mutated sequence arrangement. Thereafter, the mutated region may be removed and placed in an appropriate expression vector for protein production.

The PCR technique may also be used in creating amino acid sequence variants of an α2δ-C and/or α2δ-D protein. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 500-5000 nucleotides from that of the first, such that in the end the entire amplified region of DNA bounded by the primes can be easily sequenced. PCR amplification using a primer pair like the one just described results in a population of DNA fragments that differ at the position of the mutation specified by the primer, and possibly at other positions, as template copying is somewhat error-prone.

Further details of the foregoing and similar mutagenesis techniques are found in general textbooks, such as, for example. Sambrook et al., *Molecular Cloning: H Laboratory Manual 2nd edition*, Cold Spring Harbor Press, Cold Spring Harbor (1989), and *Current Protocols in Molecular Biology*, Ausubel et al. eds., John Wiley and Sons (1995).

Naturally-occurring amino acids are divided into groups based on common side chain properties:

(1) hydrophobic: norleucine, met, ala, val, leu, ile;
(2) neutral hydrophobic: cys, ser. tier;
(3) acidic: asp, glu;
(4) basic: asn, gin, his, lys, erg;
(5) residues that influence chain orientation: gly, pro; and
(6) aromatic: trp, tyr, pine.

Conservative substitutions involve exchanging a member within one group for another member within the same group, whereas non-conservative substitutions will entail exchanging a member of one of these classes for another. Variants obtained by non-conservative substitutions are expected to result in significant changes in the biological properties/function of the obtained variant, and may result in α2δ-C and/or α2δ-D protein variants which block α2δ-C and/or α2δ-D protein biological activities, i.e., modulation of calcium flux, or binding to neutral, alpha-amino acids. Amino acid positions that are conserved among various species are generally substituted in a relatively conservative manner if the goal is to retain biological function.

Amino acid sequence deletions generally range from about 1 to 30 residues, more preferably about 1 to 10 residues, and typically are contiguous. Deletions may be introduced into regions not directly involved in ligand binding.

Amino acid insertions include amino- and/or carboxyl terminal fusions ranging in length from one residue to polypeptides containing a hundred or more residues, as well as intrasequence insertions of single or multiple amino acid residues. Intrasequence insertions (i.e. insertions within the α2δ-C and/or α2δ-D protein amino acid sequence) may range generally from about 1 to 10 residues, more preferably 1 to 5 residues, more preferably 1 to 3 residues. Examples of terminal insertions include the α2δ-C and/or α2δ-D proteins with an N-terminal methionyl residue, a naturally-occuring N-terminal signal sequence, an artifact of direct expression in bacterial recombinant cell culture, and fusion of a heterologous N-terminal signal sequence to the N-terminus of the α2δ-C and/or α2δ-D protein to facilitate the secretion of the mature α2δ-C and/or α2δ-D protein from recombinant host cells. Such signal sequences will generally be obtained from, and thus homologous to, the intended host cell species. Suitable sequences include STII or Ipp for *E. coli*, alpha factor for yeast, and viral signals such as herpes gD for mammalian cells. Other insertional variants of the native α2δ-C and/or α2δ-D protein molecules include the fusion of the N- or C-terminus of an α2δ-C and/or α2δ-D protein to immunogenic polypeptides, e.g. bacterial polypeptides such as betalactamase or an enzyme encoded by the E. cold trp locus, or yeast protein, and C-terminal fusions with proteins having a long half-life such as immunoglobulin regions (preferably immunoglobulin constant regions), albumin, or ferritin, as described in PCT published application WO 89/02922.

Since it is often difficult to predict in advance the characteristics of a variant α2δ-C and/or α2δ-D protein, it will be appreciated that screening will be needed to select the optimum variant. For this purpose biochemical screening assays, such as those described herein below, will be readily available.

In a further aspect, the present invention provides antibodies and methods for detecting antibodies that selectively bind polypeptides with an amino acid sequence substantially similar to the amino acid sequence of SEQ ID NOS 5-6. As discussed in greater detail, infra, the antibody of the present invention can be a polyclonal or a monoclonal antibody, prepared by using all or part of the sequence of SEQ ID NOS 5-6, or modified portions thereof, to elicit an immune response in a host animal according to standard techniques (Harlow and Lane (1988), eds. Antibody: A Laboratory Manual, Cold Spring Harbor Press). In a preferred embodiment, the entire polypeptide sequence of SEQ ID NOS 5-6 is used to elicit the production of polyclonal antibodies in a host animal.

The method of detecting α2δ-C and/or α2δ-D antibodies comprises contacting cells with an antibody that recognizes α2δ-C and/or α2δ-D protein and incubating the cells in a manner that allows for detection of the α2δ-C and/or α2δ-D protein-antibody complex. Standard conditions for antibody detection of antigen can be used to accomplish this aspect of the invention (Harlow and Lane, 1988). This aspect of the invention permits the detection of α2δ-C and/or α2δ-D protein both in vitro and in vivo.

The subject invention provides methods for the treatment of a variety of diseases characterized by undesirably abnormal cellular levels of α2δ-C and/or α2δ-D. Diseases may be treated through either in vivo or in vitro genetic therapy. Protocols for genetic therapy through the use of viral vectors can be found, among other places, in Viral Vector Gene Therapy and Neuroscience Applications, Kaplit and Lowry, Academic Press, San Diego (1995). Gene therapy applications typically involve identifying target host cells or tissues in need of the therapy, designing vector constructs capable of expressing a desired gene product in the identified cells, and delivering the constructs to the cells in a manner that results in efficient transduction of the target cells. The cells or tissues targeted by gene therapy are typically those that are affected by the disease that the vector construct is designed to treat. For example, in the case of cancer, the targeted tissues are malignant tumors.

The genetic therapy methods of the present invention comprise the step of introducing a vector for the expression of α2δ-C and/or α2δ-D protein (or inhibitory anti-sense RNA) into a patient cell. The patient cell may be either in the patient, i.e., in vivo genetic therapy, or external to the patient and subsequently reintroduced into the patient, i.e., in vitro genetic therapy. Diseases that may be treated by the subject genetic therapy methods include, but are not limited to epilepsy, chronic pain, ALS, mania, cancer, anxiety, diabetes, tremor, parkinsonism, migraine, ataxia, mood, sleep interference, multiple sclerosis and inflammation).

In a preferred aspect of the invention, a method is provided for protecting mammalian cells from abnormal levels of α2δ-C and/or α2δ-D in cells, comprising introducing into mammalian cells an expression vector comprising a DNA sequence substantially similar to the DNA sequence shown in SEQ ID NOS 3 or 4, that is operatively linked to a DNA sequence that promotes the expression of the DNA sequence and incubating the cells under conditions wherein the DNA sequence of SEQ ID NOS 3 or 4 will be expressed at high levels in the mammalian cells. Suitable expression vectors are as described above. In a preferred embodiment, the coding region of the human α2δ-C and/or α2δ-D gene is subcloned into an expression vector under the transcriptional control of the cytomegalovirus (CMV) promoter to allow for constitutive α2δ-C and/or α2δ-D gene expression.

In another preferred aspect of the present invention, a method is provided for treating or preventing abnormal levels of α2δ-C and/or α2δ-D in VSCCs, comprising introducing into mammalian tumor cells an expression vector comprising a DNA that is antisense to a sequence substantially similar to the DNA sequence shown in SEQ ID NOS 3 or 4 that is operatively linked to a DNA sequence that promotes the expression of the antisense DNA sequence. The cells are then grown under conditions wherein the antisense DNA sequence of SEQ ID NOS 3 or 4 will be expressed at high levels in the mammalian cells.

In a most preferred embodiment, the DNA sequence consists essentially of SEQ ID NOS 3 or 4. In a further preferred embodiment, the expression vector comprises an adenoviral vector wherein α2δ-C and/or α2δ-D cDNA is operatively linked in an antisense orientation to a cytomegalovirus (CMV) promoter to allow for constitutive expression of the α2δ-C and/or α2δ-D antisense cDNA in a host cell. In a preferred embodiment, the α2δ-C and/or α2δ-D adenoviral expression vector is introduced into cells by injection into a mammal.

Another aspect of the invention is to provide assays useful for determining if a compound of interest can bind to α2δ-C and/or α2δ-D proteins. This binding may interfere with, or mimic, the binding of ligands to the VSCCs, or this binding may affect the function of α2δ-C and/or α2δ-D in modulating calcium flux. The assay comprises the steps of measuring the binding of a compound of interest to an α2δ-C and/or α2δ-D protein. Either the α2δ-C and/or the α2δ-D protein or the compound of interest to be assayed may be labeled with a detectable label, e.g., a radioactive or fluorescent label, so as to provide for the detection of complex formation between the compound of interest and the α2δ-C and/or α2δ-D protein. In another embodiment of the subject assays, the assays involve measuring the interference, i.e., competitive binding, of a compound of interest with the binding interaction between an α2δ-C and/or α2δ-D protein and a ligand already known to bind to α2δ-A protein. For example, the effect of increasing quantities of a compound of interest on the formation of complexes between radioactivity labeled ligand and an α2δ-C and/or α2δ-D protein may be measured by quantifying the formation of labeled ligand-α2δ-C and/or α2δ-D protein complex formation. In another embodiment of the subject assays, the assays involve measuring the alteration, i.e., non-competitive inhibition, of a compound of interest with the activity of α2δ-C and/or α2δ-D protein (compounds which bind to a different region of α2δ and inhibit α2δ activity, but don't prevent binding of ligands such as gabapentin).

Polyclonal antibodies to α2δ-C and/or α2δ-D proteins generally are raised in animals by multiple subcutaneous (se) or intraperitoneal (ip) injections of an α2δ protein and an adjuvant. It may be useful to conjugate the α2δ-C and/or α2δ-D protein or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine resides), glutaraldehyde, succinic anhydride, $SOCl_2$, or $R_1$-N=C=NR, where R and $R_1$ are different alkyl groups.

Animals are immunized against the immunogenic conjugates or derivatives by combining 1 mg or 1 fig of conjugate (for rabbits or mice, respectively) with 3 volumes of Freund's complete adjuvant and injecting the solution intradermally at multiple sites. One month later the animals are boosted with ⅕ to ¹⁄₁₀ the original amount of conjugate in Freund's complete adjuvant by subcutaneous injection at multiple sites. Seven to 14 days later the animals are bled and the serum is assayed for anti-α2δ-C and/or α2δ-D protein antibody titer. Animals are boosted until the titer plateaus. Preferably, the animal is boosted with the conjugate of the same α2δ-C and/or α2δ-D protein, but also may be conjugated to a different protein and/or through a different cross-linking reagent. Conjugates also can be made in recombinant cell culture as protein fusions. Also, aggregating agents such as alum are used to enhance the immune response.

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. For example, the anti-α2δ-C and/or α2δ-D protein monoclonal antibodies of the invention may be made using the hybridoma method first described by Kohler & Milstein, Nature 256:495 (1975), or may be made by recombinant DNA methods [Cabilly, et al, U.S. Pat. No. 4,816,567].

Antibodies can also be generated using phage display. In this approach libraries of peptides of random sequence are generated in antibody genes cloned into phage. These phage libraries are screened for antibodies by screening against the immobilized protein. (Hoogenboom-H R, Trends-Biotechnol. 1997 February; 15(2): 62-70)

In the hybridoma method, a mouse or other appropriate host animal, such a hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell [Coding, *Monoclonal Antibodies: Principles and Practice*, pp. 59-103 (academic Press, 1986)].

The anti-α2δ-C and/or α2δ-D protein specific antibodies of the invention have a number of uses. The antibodies may be used to purify α2δ-C and/or α2δ-D proteins from either recombinant or non-recombinant cells. The subject antibodies may be used to detect and/or quantify the presence of α2δ-C and/or α2δ-D proteins in tissue samples, e.g., from blood, skin, and the like. Quantitation of α2δ-C and/or α2δ-D proteins may be used diagnostically for those diseases and physiological or genetic conditions that have been correlated with particular levels of α2δ-C and/or α2δ-D protein expression levels.

In a further aspect, the present invention provides a diagnostic assay for detecting cells containing α2δ-C and/or α2δ-D deletions, comprising isolating total genomic DNA from the cell and subjecting the genomic DNA to PCR amplification using primers derived from the DNA sequence of SEQ ID NOS 3 or 4.

This aspect of the invention enables the detection of α2δ-C and/or α2δ-D deletions in any type of cell, and can be used in genetic testing or as a laboratory tool. The PCR primers can be chosen in any manner that allows the amplification of an α2δ-C and/or α2δ-D gene fragment large enough to be detected by gel electrophoresis. Detection can be by any method, including, but not limited to ethidium bromide staining of agarose or polyacrylamide gels, autoradiographic detection of radio-labeled α2δ-C and/or α2δ-D gene fragments, Southern blot hybridization, and DNA sequence analysis. In a preferred embodiment, detection is accomplished by polyacrylamide gel electrophoresis, followed by DNA sequence analysis to verify the identity of the deletions. PCR conditions are routinely determined based on the length and base-content of the primers selected according to techniques well known in the art (Sambrook et al., 1989).

An additional aspect of the present invention provides a diagnostic assay for detecting cells containing α2δ-C and/or α2δ-D deletions, comprising isolating total cell RNA and subjecting the RNA to reverse transcription-PCR amplification using primers derived from the DNA sequence of SEQ ID NOS 3 or 4. This aspect of the invention enables the detection of α2δ-C and/or α2δ-D deletions in any type of cell, and can be used in genetic testing or as a laboratory tool.

Reverse transcription is routinely accomplished via standards techniques (Ausubel et al., in Current Protocols in Molecular Biology, ed. John Wiley and Sons, Inc., 1994) and PCR is accomplished as described above.

The present invention may be better understood with reference to the accompanying examples that are intended for purposes of illustration only and should not be construed to limit the scope of the invention, as defined by the claims appended hereto.

EXAMPLES

Example 1

The sequence for human α2δ-A, c-DNA Accession No. M76559.1, was used to perform standard BLASTP searches against the Genbank non-redundant protein database and TBLASTN searches against the expressed sequence tag database (dbEST). Four full-length RNA sequences were identified (c-DNA Accession Nos. AF040709.1, AF042792.1, AF042793.1, and AB011130.1) which were highly homologous to α2δ-A. The DNA sequence of α2δ-B is provided by SEQ ID NO 1 and the amino acid sequence of α2δ-B is provided by SEQ ID NO 2. Using standard alignment tools, these four sequences were found to represent 4 different variants of the same gene. This gene was named α2δ-B. Further searches of the sequence databases, and analysis of proprietary clustered sequences generated using Compugen software, led to the identification of additional sequences related to α2δ-B. This includes human ESTs (Accession Nos. T80372.1, AA360556.1, AI563965.1, N53512.1, a mouse EST (Accession No. AA000341.1), and a sequence from C. elegans (Accession No. CAA90091.1). Since the initial identification of α2δ-B, additional related sequences have been deposited into the Genbank database. These correspond to Accession Nos. (human: AI027237.1, AI026646.1, AA994701.1, AA887514.1, AI275868.1, AI675521.1, AA906993.1, AA301068.1, AI884536.1, AI862563.1, AI191453.1, AI241832.1, AA534927.1, AA329137.1, AI586961.1, AA394008.1, AW007700.1, R38827.1, AA255807.1, H11152.1, R60736.1, T16903.1, AA435601.1, AI094263.1; mouse: AA008996.1; rat: AI105056.1, AI502878.1).

A2δ-B is 53% identical and 69% similar at the amino acid level to α2δ-A. The α2δ-B mRNA is 5482 bp long, and codes for a protein of 1145 amino acids. The three splice-variants of α2δ-B which were identified differ only in the 5' untranslated region, and do not alter the amino acid sequence. A2δ-B aligns to genomic sequence from a previously published cosmid contig on human chromosome 3p21.3. This DNA contig covers more than 600 kb of sequence. The Accession Nos. for these genomic sequences are Z84493.1, Z84494.1, Z75743.1, Z75742.1, and Z84492.1. Analysis of the DNA sequences flanking α2δ-B led to the identification of genes flanking α2δ-B on human chromosome 3p21.3 which had been mapped in both human and mouse. These flanking genes include CIS, HyaL1, GNAI-2, and GNAT-1. In mouse, all of the flanking genes were localized to mouse chromosome 9, 60 cM. Analysis of mapping data stored in the Mouse Genome Database, by Jackson Laboratory, led to the identification of three mouse neurological phenotypes that had been genetically mapped to the same mouse chromosome 9, 60 cM region. These phenotypes include epilepsy 1, ducky and tippy. Epilepsy1 and ducky both have spike-wave activity consistent with epilepsy. This tentatively maps α2δ-B to the chromosome 9, 60 cM region in mouse, and identifies α2δ-B as a candidate gene for the mouse mutants ducky, tippy, and El1 (for overview of mapping data see FIG. 1).

Northern and RT-PCR analysis of RNA expression levels of human α2δ-B were performed to analyze the expression pattern of α2δ-B. For Northern analysis, multiple tissue Northern blots and brain blots were obtained from Clontech. Non-isotopic DNA probes for α2δ-B were generated by PCR using SEQ ID NOS 7-8 and SEQ ID NO 1 as a template. Hybridization and washing conditions were in accordance with the manufacturer's instructions (Boehringer Mannheim). A2δ-B was found to have highest expression in lung, and was also detected in brain, heart, skeletal muscle, and at lower levels in all tissues tested (FIG. 2). For the Northern blot surveying different areas of human brain, α2δ-B had the highest level of expression in the cerebral cortex, but was detected in all areas of the human brain (FIG. 2). RT-PCR expression analysis of human α2δ-B was also performed. RT-PCR analysis, using a cDNA tissue panel obtained from Clontech and SEQ ID NOS 7-8 for PCR-based gene amplication (cycles: 1× at 94 C 1', 35× at 94 C 0.5°, 55 C 1', 72 C 2'; 1× at 72 C 10'), produced an expression pattern for α2δ-B consistent with results from Northern analysis. Overall, the expression pattern of α2δ-B is consistent with a proposed role of α2δ-B in epilepsy.

In order to determine if α2δ-B has functional properties comparable to α2δ-A, the ability of α2δ-B to bind to amino acids and gabapentin was measured. For this analysis, COS-7 cells were transiently transfected with the full-length porcine $α_2δ$-A, and human $α_2δ$-B genes each in the vector pcDNA3 (Invitrogen)(pcDNA3.1 for $α_2δ$-B) by the lipofectamine mediated transfection method. The cells were transfected and membranes harvested by the generic methods outlined below. The $K_D$ for binding of [$^3$H] gabapentin to α2δ-B, as compared to α2δ-A, can be found in Table 1. Additional binding studies were performed using techniques similar to those outlined below. Alterations to the protocol are listed below under the subheading "Alternative Method for Measuring [$^3$H] Gabapentin binding". The data for these binding studies are in FIG. 3. Overall, the binding and Western data demonstrated that the porcine $α_2δ$-A and human $\alpha_2\delta$-B full-length gene-products expressed transiently in the COS-7 system bind [$^3$H]gabapentin with high affinity.

TABLE 1

Saturation binding data for α2δ-B

| Porcine $\alpha_2\delta$-A (n = 2) | Human $\alpha_2\delta$-B (n = 2) |
|---|---|
| $K_D$, 23.1 nM | $K_D$, 32.6 nM |
| $K_D$, 21.2 nM | $K_D$, 87.2 nM |
| Mean = 22.2 uM | Mean = 59.9 nM |

Transient Transfection method (150 mm plate)
1: Seed 3.9×10$^6$ COS-7 cells/i 50 mm plate in 42 ml DMEM+10% FBS+5 u/ml Penicillin/5 μg/ml Streptomycin on 150 mm plate. Grow O/N.
2: Setup
Tube A—30 ug DNA in 300 ul TE+1.8 ml Optimem (5 u/ml Penicillin/5 μg/ml Streptomycin)
Tube B—150 ul Lipofectamine+1.95 ml Optimem (5 u/ml Penicillin/5 μg/ml Streptomycin)
3: At time=0 mix tubes A and B and leave at RT for 45 minutes.
4: Wash cells with 30 ml Optimem (5 u/ml Penicillin/51 g/ml Streptomycin) twice then add 16.8 ml Optimem (5 u/ml Penicillin/5 μg/ml Streptomycin) to the plates. At t=45 minutes add A/B mix to plates.
5: At t=6 hours add 21 ml of Optimem (5 u/ml Penicillin/5 μg/ml Streptomycin).
6: At t=24 hours replace medium with 42 ml Optimem (5 u/ml Penicillin/5 g/ml Streptomycin)
7: At t=48 hours rinse the cells twice with 20 ml of PBS then harvest.

Membrane Preparation (Perform at 4° C.)

1 Harvest cells into a 2 ml eppendorf in 1.5 ml 1 mM EDTA/1 mM EGTA/0.1 mM PMSF (added immediately prior to use from a 1000× stock)20% Glycerol/10 mM HEPES pH7.4@4° C. using a cell scraper.

2 Mix cells end-over-end for 30 minutes at 4° C. then centrifuge at 20,000×g for 5 minutes.

3 Resuspend pellet in 1.5 ml 1 mM EDTA/1 mM EGTA/20% Glycerol/10 mM HEPES pH 7.4@4° C. then immediately re-centrifuge at 20,000×g for 5 minutes.

4 Resuspend pellet to ~1 mg/ml (protein concentration as determined by the Bradford protein assay) in 1 mM EDTA/1 mM EGTA/20% Glycerol/10 mM HEPES pH 7.4@4° C.

For total [H3] binding, cells were sonicated for 30-40 seconds, centrifuged for 10' at 750-1000×g, and the supernatent was centrifuged for 30' at 50,000×g. The resulting pellet was resuspended in 5 mM

[$^3$H] Gabapentin Saturation Binding Assay Methodology and Data Analysis

Assays were carried out at 21° C. in a final volume of 250 μl in 96-well deep-well plates. Duplicate wells were set up for both 'total' and 'non-specific' binding. Specific binding was defined as that remaining after subtraction of the 'non-specific binding' values from the 'total' binding values. Assay components were added in the following order (all reagents were diluted in 10 mM HEPES (pH 7.4 at 21° C.)):

| | |
|---|---|
| Total binding | 200 μl 10 mM HEPES pH 7.4 |
| Non-specific binding | 175 μl 10 mM HEPES pH 7.4 and 25 μl 100 μM (S+)-3-isobutyl GABA |
| | 25 μl Appropriate COS membrane sample |
| | 25 μl [$^3$H]gabapentin |

The reaction was incubated at 21° C. for 45 minutes then filtered through GF/B filters soaked in 50 mM Tris-Cl pH 7.4 @4° C. (wash buffer), filters were washed three times with wash buffer.

The filters were then counted in a scintillation counter.

Saturation experiments were performed with 12 duplicate data points ('Total' and 'Non-Specific' binding determined in duplicate for each concentration of [$^3$H]gabapentin tested) and a [$^3$H]gabapentin concentration range from ~1 to 400 nM. Data was analyzed using KEL-RADLIG for Windows.

Alternative Method for Measuring [$^3$H] Gabapentin Binding

The method described above was followed with the following exceptions:

1) COS7 transfection: 20 ug of α2δ-A or α2δ-B plasmid DNA were incubated with 30 ul of lipofectamine. The mixture was overlaid onto the cells in 1.5 ml of serum-free medium and incubated for 5 hours. Then FBS was added to the dishes to bring the final concentration to 10%. The medium was changed the next morning. Forty-eight hours after transfection the cells were harvested for membrane preparation.

2) Membrane preparation: Cells were washed twice with cold PBS and then scraped off the tissue culture plates in cold 5 mM of Tris/5 mM EDTA (pH7.4) containing PMSF (0.1 mM), leupeptin (0.02 mM), and pepstatin (0.02 mM). The cells were incubated on ice for 30 minutes and then sonicated for 30-40 seconds. The homogenate was centrifuged for 10 minutes at 750-1000×g, and then the supernatent was centrifuged for 30 minutes at 50,000×g. The resulting pellet was resuspended in the same buffer as described above.

3) Binding Assays: The radioligand binding assay was done using 0.05 mg of membrane protein incubated in the presence of 20 nM of [$^3$H] gabapentin. The membranes were incubated in 10 mM Hepes (pH 7.4) for 40-50 minutes at room temperature, and then filtered onto pre-wetted GF/C membranes and quickly washed five times with 3 ml of ice cold 50 mM tris buffer pH7.4. The filters were dried and counted in a liquid scintillation counter. To determine background binding, 10 uM of isobutyl GABA was used and the resulting counts subtracted from the total counts of each sample.

Detection of α2δ-A and α2δ-B Expression with Anti-α$_2$ Polyclonal Antibodies

Using affinity purified anti-α$_2$ polyclonal antibodies (antigen derived from porcine α$_2$δ-A; See Brown and Gee (1998) *JBC* 273 25458-25465 for pAb generation details) the expression of the porcine α$_2$δ-A and human α2δ-B proteins (over and above control levels —COS cells transfected with the parent pcDNA3 vector) was confirmed. N.B. Cross reaction of the pAb's with α$_2$δ-B was not unexpected given the ~50% amino acid sequence identity. Furthermore, and with reference to Example 2, expression of α$_2$δ-C was not detected using this antibody (sequence identity with α$_2$δ-A 30%).

Example 2

The sequence for human $\alpha_2\delta$-A, Accession No. M76559.1, was used to perform standard BLASTP searches against the Genbank non-redundant protein database and TBLASTN searches against the expressed sequence tag database (dbEST). EST sequences were identified (Accession Nos. AA815447.1, AA190607.1, AI223142.1, AA188635.1, R43629.1, R20288.1, AA459684.1, AA662058.1, Z44942.1, Z40693.1, AI051759.1) corresponding to a new gene, with similarity to $\alpha_2\delta$-A, named $\alpha_2\delta$-C. Additional searches of the sequence databases led to the identification of other sequences related to $\alpha_2\delta$-C. This includes a mouse EST (Accession No. AU022914.1, AI843362.1), and an STS (Accession No. G36524.1) which maps to human chromosome 3p21.1. Since the initial identification of $\alpha_2\delta$-B, additional related sequences have been deposited into the Genbank database. These correspond to Accession Nos. (human ESTs: AA459804.1, AI696320.1, A1051759.1, AI696214.1; human genomic sequence: AC010180.1; mouseEST: AA445859.1, mouseRNA: AJ010949.1).

In order to clone a full-length $\alpha_2\delta$-C, a PCR-based cDNA library screen was carried out by Origene using primers (SEQ ID NOS 9-10) based on sequence derived from EST clone accession number AA190607.1 which were designed to amplify a 273 bp fragment. A positive clone was identified in a kidney library. After sequencing, this clone was identified as a novel 3' splice variant (SEQ ID NO 43). The protein sequence, which can be derived from SEQ ID NO 43, of this novel splice variant is a truncated, potentially secreted soluble form of $\alpha 2\delta$-C. PCR was performed, using primers (SEQ ID NOS 9 and 11) and a human adult brain library from LTI as a template, and the resulting fragment of 248 bp was cloned in pBS and sequence verified. A SacI-NcoI fragment from the kidney clone, a NcoI-KpnI fragment from the PCR center clone, and a KpnI-NotI fragment from a clone obtained from the IMAGE consortium (corresponding to Accession No. R43629.1) were ligated together, using methods standard to the art, to create a full-length clone. Each individual clone, and the full-length clone (SEQ ID NO 3), were sequence verified. A number of other EST clones from the IMAGE consortium were also obtained and sequenced. One of these clones (corresponding to Accession No. AI051759.1) contained a two novel splice-variants which result in a truncated, potentially soluble $\alpha_2\delta$-C (SEQ ID NO 44).

Full-length $\alpha_2\delta$-C is 28% identical and 48% similar at the amino acid level to $\alpha_2\delta$-A. The $\alpha_2\delta$-C mRNA sequence (SEQ ID NO 3) is 3770 bp long, and codes for a protein of 1085 amino acids (SEQ ID NO 5). In addition, three splice variants of $\alpha_2\delta$-C were identified. Two of the variants contain deletions of internal exons. The third variant contains a novel 3' end. Two of these splice-variants produce a truncated protein which is devoid of the membrane anchoring delta subunit. These variants may represent a secreted alpha2 protein which could have additional functions beyond regulation of voltage-sensitive calcium channels.

In order to identify sequences for $\alpha_2\delta$-C from other species, human and mouse specific primers (SEQ ID NOS 9-10 and 12-13, respectively) were used to amplify $\alpha_2\delta$-C RT-PCR products. RNA from human brain was purchased from Invitrogen, Carlsbad, Calif. (catalog #D6030-15). RNA from rat and mouse brain was isolated using standard in-house protocols. First-strand cDNA synthesis was completed using Superscript Choice System (LTI, Bethesda, Md., catalog #18090-019). Ethanol precipitated cDNA was added to PCR mix containing 1x PCR buffer, 0.2 mM dNTP, 10 pmol/well forward primer, 10 pmol/well reverse primer, and 0.5 units Platinum TAQ High Fidelity (LTI, Bethesda, Md.). Products were amplified at 95° C. for 5 minutes, followed by 35 cycles of 95° C. for 1 minute, 58° C. for 1 min, 68° C. for 2 minutes, and final extension at 72° C. for 10 minutes. PCR products were assayed on 1% agarose (TAE) gels at 100 volts for 45 minutes. Gels were visualized under UV and photographed. Products were purified using Millipore Ultrafree-MC PCR purification filter units (catolog # UFC3LTKOO) prior to DNA sequence analyses. Using this approach, three sets of primers (SEQ ID NO 36, 37; SEQ ID NO 12, 13, SEQ ID NO 38, 39) where used for PCR amplification of rat $\alpha 2\delta$-C. Three partial rat sequences for $\alpha 2\delta$-C were identified (SEQ ID NOS 40, SEQ ID NO 14, SEQ ID NO 41).

RT-PCR analysis of RNA expression levels were performed to analyze the expression pattern of $\alpha_2\delta$-C. cDNA Expression Panels were purchased from OriGene Technologies, Inc. (Rockville, Md.). Human (catalog # HSC-101) and Mouse (catalog # MSCB-101) cDNAs from 24 tissue sources were pre-arrayed in a 96-well PCR format. PCR mix containing 1x PCR buffer, 0.2 mM dNTP, 10 pmol/well forward primer, 10 pmol/well reverse primer, and 0.5 units Platinum TAQ (LTI, Bethesda, Md.) was added to each well. Products were amplified at 95° C. for 5 minutes, followed by 35 cycles of 95° C. for 1 minute, 58° C. for 1 min, 68° C. for 2 minutes, and final extension at 72° C. for 10 minutes. PCR products were assayed on 1% agarose (TAE) gels at 100 volts for 45 minutes. Gels were visualized under UV and photographed. The primers used for this amplification from the human template correspond to SEQ ID NOS 9-10, and from the mouse template correspond to SEQ ID NOS 12-13. By RT-PCR, $\alpha 2\delta$-C was found to be expressed in a wide variety of tissues (Table 2). The highest levels of $\alpha_2\delta$-C were detected in human brain, and also in human testis and kidney. In addition to RT-PCR, the cDNA sequence for this gene has been detected in a human, adult brain library and also libraries from: infant brain, hNT neural cell line, testis, total fetus, alveolar rhabdomyosarcoma, adenocarcinoma, and a pooled germ cell library.

Northern blot analysis was performed using $\alpha 2\delta$-C as a probe. Human total RNA was obtained from Invitrogen (Carlsbad, Calif.) (brain. total RNA (Cat #D6030-01), kidney total RNA (Cat #D6070-01), testis total RNA (Cat #D6121-01), liver total RNA (Cat # D6080-015)) or Ambion Inc (Austin, Tex.)(placenta total RNA Cat#7950, heart total RNA Cat #7966), lung total RNA (Cat #7968)) RNA was electrophoresed in formaldehyde agarose gels then transferred to charged nylon membranes (Ambion Inc. (Austin Tex.) Cat #10104. The EST clone (SEQ ID NO 47) was digested with BamHI and used as template in an RNA synthesis reaction that yielded 32P labeled probe. The nylon membranes containing the RNA were prehybridized for 2 hours in ExpressHyb hybridization solution (Clontech Inc. (Palo Alto, Calif.)(Cat # 8015-1). After the prehybridization $4\times10^6$ cpm of RNA probe labeled with 32P wre added to the solution and the hybridization was performed in the same solution for 2 hours. After hybridization the nylon filter was washed for 1 hour with 4 changes of 2x SSC, 0.5% SDS at room temperature. The nylon filter was transferred to a solution of 0.2x SSC, 0.5% SDS at 68° C. and washed with 4 changes of solution. The nylon filters were then exposed to phosphoroimager screens Molecular Dynamics (Sunnyvale, Calif.) and read on a Storm phosphorimager. Molecular Dynamics (Sunnyvale, Calif.). Results from Northern analysis (FIG. 4) indicate that α2δ-C has highest levels of expression in human brain, kidney, and testis.

Since α₂δ-C has sequence homology to α₂δ-A, and α₂δ-A functions as a subunit of VSCCs, experiments were undertaken to determine if α₂δ-C can replace α₂δ-A and produce functional VSCCs. *Xenopus* oocytes were isolated using standard techniques and injected with cRNA for $\alpha_{1B}$, $\beta_{1C}$ and α₂δ-C subunits of voltage-gated Ca²⁺ channels. Four days to 1 week following injection of cRNA, Ca²⁺ channel currents were measured using two-electrode voltage clamp with 5 mM Ba²⁺ as the charge carrier. Test pulses to +10 mV from a holding membrane potential of −80 mV were applied to evoke Ca²⁺ channel currents. Peak inward currents evoked during the test pulse were measured. The amplitude of inward currents is proportional to the expression level of voltage-gated Ca²⁺ channels.

Expression of $\alpha_{1B}$, $\beta_{1C}$ without α₂δ subunits produced currents with an average amplitude of 105±13 nA (n=20). Co-injection of $\alpha_2\delta_C$, with $\alpha_{1B}$ and $\beta_{1C}$ subunits produced a significant increase in current amplitude to 213±12 nA (n=20, p<0.01 compared to no α₂δ subunits). These data suggest that $\alpha_2\delta_C$ has an effect on Ca²⁺ channels similar to $\alpha_2\delta_A$, enhancing the level of channel expression. However, $\alpha_2\delta_C$ did not produce as large of an effect on channel expression as $\alpha_2\delta_A$, producing a 2-fold increase in current compared to a 20-fold increase observed with the co-injection of $\alpha_2\delta_A$. Overall, these initial functional studies indicate that α₂δ-C can replace α₂δ-A in voltage-sensitive calcium channels after co-injection into *Xenopus* oocytes with the α1 and beta subunits.

TABLE 2

RT-PCR EXPRESSION PROFILE FOR ALPHA2-DELTA C

| Tissue | Human α2d-C | Mouse α2d-C |
|---|---|---|
| Brain | +++ | + |
| Heart | ++++ | − |
| Kidney | ++ | ++ |
| Liver | − | − |
| Colon | + | not assayed |
| Lung | + | ++ |
| Small Intestine | ++ | + |
| Muscle | ++++ | ++ |
| Stomach | ++ | − |
| Testis | +++ | ++ |
| Placenta | ++ | not assayed |
| Salivary Gland | ++ | not assayed |
| Thyroid Gland | ++ | not assayed |
| Adrenal Gland | ++ | − |
| Pancreas | ++ | not assayed |
| Ovary | ++ | − |
| Uterus | ++ | − |
| Prostrate | ++ | ++ |
| Skin | ++ | − |
| PBL | − | not assayed |
| Bone Marrow | − | not assayed |
| Fetal Brain | ++ | not assayed |
| Fetal Liver | ++ | not assayed |

Example 3

The sequence for human α2δ-A, Accession No. M76559.1, was used to perform BLASTP searches against the Genbank non-redundant protein database and TBLASTN searches against the expressed sequence tag database (dbEST). EST sequences were identified (Accession No. T70594.1, T96901.1, AA766033.1, AI160471.1, AA719773.1, AI003601.1, AA442451.1, AA521470.1, AA770076.1, AA001411.1, AA001473.1, W22650.1, H86016.1) corresponding to a new gene, with similarity to α2δ-A, named α2δ-D. Additional searches of the sequence databases led to the identification of other sequences related to α2δ-D. This includes genomic sequence derived from human chromosome 12p13.3 (Accession No. AC005342.1, AC005343.1). Since the initial identification of α2δ-D, additional related sequences have been deposited into the Genbank database. These sequences correspond to Accession Nos. (human ESTs: T96900.1, AI457823.1, AI377638.1, and AI433691.1).

To isolate a full-length α2δ-D clone, a PCR-based cDNA library screen was carried out by Origene using primers (SEQ ID NOS 18-19) based on sequence derived from EST clone Accession No. AA001473.1 which were designed to amplify a 372 bp fragment. A positive clone was identified in a placental library, and was confirmed using a nested internal primer (SEQ ID NO 20). This clone was fully sequenced. The sequence extended 350 bp 5' of the sequence obtained from the EST sequences, but did not include the 5' end.

To obtain the 5' end, two approaches were undertaken. One approach utilized 5' RACE (Rapid Amplification of cDNA Ends). For 5' RACE, placenta poly A+ RNA from Clontech was used to construct a RACE-ready cDNA library using a Marathon cDNA Amplification kit purchased from Clontech. The 5'-end sequence of α2δ-D was obtained by 5' RACE PCR using first set of primers: Marathon cDNA adapter primer 1 (SEQ ID NO 45) and gene specific primer I (SEQ ID NO 21). The PCR product was re-amplified using a set of nested primers: adapter primer 2 (SEQ ID NO 46) and gene specific primer II (SEQ ID NO 22). A resulting 1 kb PCR product was cloned into a TA vector (Invitrogen) and sequenced. Sequence analysis revealed that it contains the 5' sequence of α2δ-D.

A second method undertaken to identify the 5' end of α2δ-D was a PCR-based library screen performed by Edge, using the 5' most sequence known for α2δ-D. Nine clones were PCR amplified by the methods indicated above, for verification using primers with SEQ ID NOS 48 and 49. These nine positive clones were then sequenced for verification by standard methods. All nine clones were identical to each other, and all were short of the 5' end by approximately 500 bp. However, these clones contained novel splice-variants of α2δ-D, with insertions of novel nucleotide sequences (SEQ ID NO 16).

The full-length sequence of α2δ-D is 28% identical and 47% similar at the amino acid level to α2δ-A. The α2δ-D mRNA is 5,073 bp long (SEQ ID NO 4), and codes for a protein of 1120 amino acids (SEQ ID NO 6). In addition, two splice variants of α2δ-D were identified. One of the variants contains a 72 bp deletion of an internal exon (SEQ ID NO 15). The amino acid sequence of this variant can be found in SEQ ID NO 17. The second variant contains two novel insertions, one of 338 bp and one of 305 bp (SEQ ID NO 16). These insertions appear to result in a truncated protein (SEQ ID NO 42), comparable to the truncated protein sequence identified for α2δ-C in Example 2.

RT-PCR analysis of RNA expression levels of human α₂δ-D were performed in order to analyze the tissue distribution of α2δ-D. cDNA Expression Panels were purchased from OriGene Technologies, Inc. (Rockville, Md.). Human (catalog # HSC-101) and Mouse (catalog # MSCB-101) cDNAs from 24 tissue sources were pre-arrayed in a 96-well PCR format. PCR mix containing 1× PCR buffer, 0.2 mM dNTP, 10 pmol/well forward primer, 10 pmol/well reverse primer, and 0.5 units Platinum TAQ (LTI, Bethesda, Md.) was added to each well. Products were amplified at 95° C.

for 5 minutes, followed by 35 cycles of 95° C. for 1 minute, 58° C. for 1 min, 68° C. for 2 minutes, and final extension at 72° C. for 10 minutes. PCR products were assayed on 1% agarose (TAE) gels at 100 volts for 45 minutes. Gels were visualized under UV and photographed. In the case of the α2δ-D human panels two separate sets of primers were used to distinguish splice variants and wild type species (SEQ ID NOS 18 & 20, SEQ ID NOS 23 & 19, respectively).

Analysis of the results from RT-PCR of $α_2δ$-D (see Table 3) indicate that $α_2δ$-D is expressed in a wide variety of tissues, with highest levels in placenta, adrenal gland and pancreas, but also detected in all tissues other than colon. Of note, α2δ-D was detected in human brain, consistent with a potential role in neurological disease. In addition, based on the tissue distribution of EST sequences, the cDNA sequence for $α_2δ$-D has been detected in human libraries from: adult brain, retina, fetal liver/spleen, fetal heart, pineal gland, and testis.

TABLE 3

RT-PCR EXPRESSION PROFILE FOR ALPHA2-DELTA D

| Tissue | Human α2δ-D ** | Human α2δ-D |
|---|---|---|
| Brain | +++ | +++ |
| Heart | +++ | – |
| Kidney | +++* | – |
| Liver | ++ | – |
| Colon | – | – |
| Lung | ++ | – |
| Small Intestine | +* | – |
| Muscle | ++ | – |
| Stomach | ++ | – |
| Testis | +++ | – |
| Placenta | ++++* | – |
| Salivary Gland | ++ | ++++ |
| Thyroid Gland | +++ | ++++ |
| Adrenal Gland | ++++ | +++ |
| Pancreas | ++++* | ++ |
| Ovary | ++* | ++ |
| Uterus | +* | ++ |
| Prostate | ++* | + |
| Skin | + | – |
| PBL | +++ | – |
| Bone Marrow | +++ | – |
| Fetal Brain | +++ | – |
| Fetal Liver | ++ | – |

*2 products: wt and splice variant
** Primers d2 + dhD-2 detects splice region

Example 4

Knockout of α2δ-B

In order to create a mouse knockout of α2δ-B, Genome Systems (Catalog: BAC 4922 Mouse ES 129Svj PCR based Library Screen) performed a PCR-based screen of a mouse BAC library using primers SEQ ID NOS 25-26, which were predicted to amplify an 650 bp cDNA or genomic fragment. One positive BAC clone (Genome Systems DNA control number: BAC-22401) from this screen was received. The same primers were used to generate a human DNA probe. This probe was used on a Southern blot to identify a ~10 kb HindIII mouse genomic fragment from the BAC, which was subcloned into the HindIII site of plasmid vector pRS416 (Stratagene). Two separate subclones were sequenced by standard techniques, using the T3 and T7 primers and SEQ ID NOS (25-32). Two 500 bp regions of sequence from the 5' and 3' ends of the 10 kb genomic fragment (SEQ ID NOS 33 and 34, respectively), plus a 1.8 kb sequence contig (SEQ ID NO 35) were identified. This genomic sequence can be used to identify the intron/exon structure of a portion of mouse α2δ-B gene, and may contain regulatory elements important for α2δ-B gene expression.

Example 5

Identification of Amino Acids Encoded by α2δ Gene

The amino acid sequences of α2δ-C and α2δ-D, indicated in SEQ ID NOS 5 and 6, were determined by translating the nucleotide sequences described in SEQ ID NOS 3 and 4, and aligning the amino acid sequences of α2δ-A, α2δ-B, α2δ-C, and α2δ-D. The correct open reading frame for each amino acid sequence was determined based on homology of the amino acid sequences to other α2δ-A homologs. At the amino acid level, α2δ-C is 28% identical and 48% similar to α2δ-A and is 28% identical and 47% similar to α2δ-B, and α2δ-D is 28% identical and 47% similar to α2δ-A and is 28% identical and 46% similar to α2δ-B. Although α2δ-C and α2δ-D are related to α2δ-A, they are distinctly new and different genes.

Example 6

Proposed Method of Detecting the α2δ-C and α2δ-D Proteins by Using an α2δ-C and α2δ-D Antibody Antibodies could be developed which specifically detect epitopes unique to α2δ-C and α2δ-D, or which detect all α2δ proteins. These antibodies could be developed by either synthesizing a peptide which is identical to α2δ-C and/or α2δ-D, or by bacterially-expressing a fusion protein containing either α2δ-C or α2δ-D, and then injecting these peptides into a research animal in order to stimulate an immunogenic response. Antibodies generated in such a manner could be used to detect levels of α2δ-C and/or α2δ-D protein in cells. This could be done by immunocytochemistry, where whole cells are fixed and then the antibody is used on the whole cells to detect expression of α2δ-C or α2δ-D, and to detect the subcellular localization of α2δ-C or α2δ-D. Or, cells may be lysed and protein extracts generated and analyzed for α2δ-C and/or α2δ-D expression.

Example 7

Isolation of RNA for cDNA Library

In order to isolate α2δ-C or α2δ-D from cells, RNA could be isolated by lysing cells from any tissue of interest using standard methods known in the field. After isolation, RNA is reverse-transcribed into cDNA using the enzyme reverse transcriptase and a poly(T) primer or a mix of random primers. A mix of cDNA is produced, representing a large number of the genes which are expressed in the beginning cell population at a particular point in time. Once the cDNA pool has been created, it can be restricted and then ligated into a cloning vector using methods standard in the field. This results in a cDNA library.

Example 8 cDNA Cloning Procedure

A2δ-C or α2δ-D could be cloned from a cDNA library, created as above, by using primers specific for α2δ-C or α2δ-D nucleotide sequences in a polymerase chain reaction, with the cDNA used as a template. Alternatively, α2δ-C or α2δ-D sequences could be used as a probe in order to screen the cDNA library by hybridization. Using either technique, single clones are ulimately isolated from the library and sequenced using standard techniques. By sequencing multiple clones from a library, one could look for the existence of alternatively-spliced variants of α2δ-C or α2δ-D, or for the existence of single nucleotide polymorphisms, or for mutations/alterations in α2δ-C or α2δ-D.

Example 9

Screening cDNA Library with Antibody

A cDNA library could also be screened by using an antibody to α2δ-C or α2δ-D. The cDNA library is cloned into a vector which allows induction of protein expression of the cloned inserts. The complete cDNA library is induced to express a protein representing the cloned insert, then single clones which contain an insert that codes for α2δ-C or α2δ-D are identified if they hybridize to an antibody generated against α2δ-C or α2δ-D. Positive clones are isolated, and then sequenced using standard methods.

It is to be understood that the invention is not to be limited to the exact details of operation, or to the exact compounds, compositions, methods, procedures or embodiments shown and described, as obvious modifications and equivalents will be apparent to one skilled in the art, and the invention is therefore to be limited only by the full scope of the appended claims.

We claim:

1. An isolated and purified DNA sequence that hybridizes to the full complement of the DNA sequence shown in SEQ ID NO: 3 under high stringency hybridization conditions, wherein said isolated and purified DNA sequence encodes a polypeptide that is a voltage activated calcium channel α2δ-C subunit, and wherein said high stringency hybridization conditions comprises hybridization on a filter support at 65° C. in 7% SDS and 0.125 M sodium phosphate followed, by washing in 1% SDS, 20 mM phosphate buffer and 1 mM EDTA at 65° C. for between about 30 minutes to 4 hours.

2. An isolated and purified DNA sequence that consists essentially of the DNA sequence shown in SEQ ID NO: 3.

3. An isolated and purified DNA sequence that is fully complementary to the DNA sequence shown in SEQ ID NO: 3.

4. A recombinant DNA molecule comprising the isolated and purified DNA sequence shown in SEQ ID NO: 3, wherein said isolated and purified DNA sequence encodes a polypeptide that is a voltage activated calcium channel α2δ-C subunit.

5. A isolated recombinant host cell comprising a host cell transfected with the recombinant DNA molecule of claim 1.

6. A method for purifying α2δ-C protein from cells, comprising:
   a) transfecting a host cell with a vector comprising the isolated and purified DNA sequence of claim 1 or 2 operatively linked to a promoter which directs gene expression in a host cell;
   b) inducing expression of the isolated and purified DNA sequence in the cells to produce protein;
   c) lysing the cells;
   d) isolating α2δ-C protein from the cells; and purifying α2δ-C protein from the isolate.

7. An isolated and pied DNA sequence consisting of a sequence which encodes the polypeptide of SEQ ID NO: 5.

8. An isolated and purified DNA sequence, which comprises a polynucleotide sequence encoding the polypeptide of SEQ ID NO: 5.

9. An isolated and purified DNA sequence fiat consists of the DNA sequence shown in SEQ ID NO: 3.

* * * * *